(12) United States Patent
Greenhalgh et al.

(10) Patent No.: US 8,709,042 B2
(45) Date of Patent: Apr. 29, 2014

(54) EXPANDABLE SUPPORT DEVICE AND METHOD OF USE

(75) Inventors: E. Skott Greenhalgh, Wyndmoor, PA (US); John Paul Romano, Chalfont, PA (US); Michael P. Igoe, Perkasie, PA (US)

(73) Assignee: Stout Medical Group, LP, Perkasie, PA (US)

( * ) Notice: Subject to any disclaimer, the term of this patent is extended or adjusted under 35 U.S.C. 154(b) by 864 days.

(21) Appl. No.: 11/689,471

(22) Filed: Mar. 21, 2007

(65) Prior Publication Data
US 2007/0219634 A1 Sep. 20, 2007

Related U.S. Application Data

(63) Continuation-in-part of application No. PCT/US2005/037126, filed on Oct. 12, 2005, and a continuation-in-part of application No. PCT/US2005/034115, filed on Sep. 21, 2005, and a continuation-in-part of application No. PCT/US2005/034742, filed on Sep. 26, 2005.

(60) Provisional application No. 60/617,810, filed on Oct. 12, 2004, provisional application No. 60/612,001, filed on Sep. 21, 2004, provisional application No. 60/612,723, filed on Sep. 24, 2004, provisional application No. 60/612,724, filed on Sep. 24, 2004.

(51) Int. Cl.
*A61B 17/70* (2006.01)

(52) U.S. Cl.
USPC .................. 606/246; 623/17.11; 623/17.16; 606/279

(58) Field of Classification Search
USPC .................. 606/246–279; 623/17.11–17.16
See application file for complete search history.

(56) References Cited

U.S. PATENT DOCUMENTS

| 646,119 A | 3/1900 | Clamer et al. |
| 3,659,587 A | 5/1972 | Baldwin |
| 4,204,531 A | 5/1980 | Aginsky |
| 4,569,338 A | 2/1986 | Edwards |
| 4,636,217 A | 1/1987 | Ogilvie et al. |
| 4,653,489 A | 3/1987 | Tronzo |

(Continued)

FOREIGN PATENT DOCUMENTS

| EP | 0734702 | 10/1996 |
| EP | 0758541 | 2/1997 |

(Continued)

OTHER PUBLICATIONS

Franklin, I.J. et al., "Uptake of Tetracycline by Aortic Anerysm Wall and Its Effect on Inflammation and Proteolysis," *Brit. J. Surger*, 83(6):771-775, 1999.

(Continued)

*Primary Examiner* — Jerry Cumberledge
(74) *Attorney, Agent, or Firm* — Levine Bagade Han LLP

(57) ABSTRACT

An expandable support device for tissue repair is disclosed. The device can be used to repair hard or soft tissue, such as bone or vertebral discs. A method of repairing tissue is also disclosed. The device and method can be used to treat compression fractures. The compression fractures can be in the spine. The device can be deployed by compressing the device longitudinally resulting in radial expansion.

5 Claims, 57 Drawing Sheets

(56) References Cited

U.S. PATENT DOCUMENTS

| | | | |
|---|---|---|---|
| 4,716,839 | A | 1/1988 | Catena |
| 4,716,893 | A | 1/1988 | Fischer et al. |
| 4,733,665 | A | 3/1988 | Palmaz |
| 4,759,769 | A | 7/1988 | Hedman et al. |
| 4,763,644 | A | 8/1988 | Webb |
| 4,863,476 | A | 9/1989 | Shepperd |
| 4,886,062 | A | 12/1989 | Wiktor |
| 4,911,718 | A | 3/1990 | Lee et al. |
| 4,932,975 | A | 6/1990 | Main et al. |
| 4,941,466 | A | 7/1990 | Romano |
| 4,969,888 | A | 11/1990 | Scholten et al. |
| 4,978,341 | A | 12/1990 | Niederhauser |
| 5,007,909 | A | 4/1991 | Rogozinski |
| 5,015,247 | A | 5/1991 | Michelson |
| 5,026,373 | A | 6/1991 | Ray et al. |
| 5,059,193 | A * | 10/1991 | Kuslich .................. 606/247 |
| 5,108,404 | A | 4/1992 | Scholten et al. |
| 5,123,926 | A * | 6/1992 | Pisharodi .................. 623/17.13 |
| 5,139,480 | A | 8/1992 | Hickle et al. |
| 5,171,278 | A | 12/1992 | Pisharodi |
| 5,217,483 | A | 6/1993 | Tower |
| 5,258,031 | A | 11/1993 | Salib et al. |
| 5,273,533 | A | 12/1993 | Bonaldo |
| 5,306,278 | A | 4/1994 | Dahl et al. |
| 5,342,348 | A | 8/1994 | Kaplan |
| 5,345,927 | A | 9/1994 | Bonutti |
| 5,360,417 | A | 11/1994 | Gravener et al. |
| 5,390,683 | A | 2/1995 | Pisharodi |
| 5,390,898 | A | 2/1995 | Haber et al. |
| 5,391,154 | A | 2/1995 | Young |
| 5,397,364 | A * | 3/1995 | Kozak et al. .................. 623/17.11 |
| 5,425,773 | A | 6/1995 | Boyd et al. |
| 5,458,643 | A | 10/1995 | Oka et al. |
| 5,480,442 | A | 1/1996 | Bertagnoli |
| 5,484,384 | A | 1/1996 | Fearnot |
| 5,496,365 | A | 3/1996 | Sgro |
| 5,522,899 | A | 6/1996 | Michelson |
| 5,534,002 | A | 7/1996 | Brumfield et al. |
| 5,540,690 | A | 7/1996 | Miller et al. |
| 5,549,679 | A | 8/1996 | Kuslich |
| 5,554,191 | A | 9/1996 | Lahille et al. |
| 5,556,413 | A | 9/1996 | Lam |
| 5,562,736 | A | 10/1996 | Ray et al. |
| 5,562,738 | A | 10/1996 | Boyd et al. |
| 5,571,189 | A * | 11/1996 | Kuslich .................. 623/17.12 |
| 5,571,192 | A | 11/1996 | Schonhoffer |
| 5,584,831 | A | 12/1996 | McKay |
| 5,591,197 | A | 1/1997 | Orth et al. |
| 5,593,409 | A | 1/1997 | Michelson |
| 5,609,356 | A | 3/1997 | Mossi |
| 5,609,635 | A | 3/1997 | Michelson |
| 5,634,937 | A | 6/1997 | Mollenauer et al. |
| 5,643,264 | A | 7/1997 | Sherman et al. |
| 5,643,312 | A | 7/1997 | Fischell et al. |
| 5,653,763 | A | 8/1997 | Errico et al. |
| 5,658,335 | A | 8/1997 | Allen |
| 5,662,615 | A | 9/1997 | Blake, III |
| 5,665,122 | A * | 9/1997 | Kambin .................. 623/17.16 |
| 5,669,909 | A | 9/1997 | Zdeblick et al. |
| 5,674,295 | A | 10/1997 | Ray et al. |
| 5,683,394 | A | 11/1997 | Rinner |
| 5,693,100 | A | 12/1997 | Pisharodi |
| 5,702,449 | A | 12/1997 | McKay |
| 5,702,453 | A | 12/1997 | Rabbe et al. |
| 5,741,253 | A | 4/1998 | Michelson |
| 5,749,916 | A * | 5/1998 | Richelsoph .................. 623/17.16 |
| 5,772,661 | A | 6/1998 | Michelson |
| 5,776,181 | A | 7/1998 | Lee et al. |
| 5,776,197 | A | 7/1998 | Rabbe et al. |
| 5,776,198 | A | 7/1998 | Rabbe et al. |
| 5,776,199 | A | 7/1998 | Michelson |
| 5,782,832 | A * | 7/1998 | Larsen et al. .................. 623/17.11 |
| 5,782,903 | A | 7/1998 | Wiktor |
| 5,785,710 | A | 7/1998 | Michelson |
| 5,800,520 | A | 9/1998 | Fogarty et al. |
| 5,824,054 | A | 10/1998 | Khosravi et al. |
| 5,824,093 | A | 10/1998 | Ray et al. |
| 5,827,289 | A | 10/1998 | Reiley et al. |
| 5,827,321 | A | 10/1998 | Roubin et al. |
| 5,853,419 | A | 12/1998 | Imran |
| 5,861,025 | A | 1/1999 | Boudghene et al. |
| 5,863,284 | A | 1/1999 | Klein |
| 5,865,848 | A | 2/1999 | Baker |
| 5,895,387 | A | 4/1999 | Guerrero et al. |
| 5,916,198 | A | 6/1999 | Dillow |
| 5,972,015 | A | 10/1999 | Scribner et al. |
| 5,980,522 | A | 11/1999 | Koros et al. |
| 5,980,550 | A | 11/1999 | Eder et al. |
| 5,984,957 | A | 11/1999 | Laptewicz et al. |
| 6,001,130 | A | 12/1999 | Bryan et al. |
| 6,019,792 | A | 2/2000 | Cauthen |
| 6,022,376 | A | 2/2000 | Assell et al. |
| 6,025,104 | A | 2/2000 | Fuller et al. |
| 6,027,527 | A | 2/2000 | Asano et al. |
| 6,036,719 | A | 3/2000 | Meilus |
| 6,039,761 | A | 3/2000 | Li et al. |
| 6,045,579 | A | 4/2000 | Hochshuler et al. |
| 6,053,916 | A | 4/2000 | Moore |
| 6,066,154 | A | 5/2000 | Reiley et al. |
| 6,077,246 | A | 6/2000 | Kullas et al. |
| 6,080,193 | A | 6/2000 | Hochshuler et al. |
| 6,083,522 | A | 7/2000 | Chu et al. |
| 6,086,610 | A | 7/2000 | Duerig et al. |
| 6,090,143 | A | 7/2000 | Meriwether et al. |
| 6,102,950 | A | 8/2000 | Vaccaro |
| 6,111,639 | A | 8/2000 | Reduto |
| 6,126,689 | A | 10/2000 | Brett |
| 6,127,597 | A | 10/2000 | Beyar et al. |
| 6,129,763 | A | 10/2000 | Chauvin et al. |
| 6,132,465 | A | 10/2000 | Ray et al. |
| 6,140,452 | A | 10/2000 | Felt et al. |
| 6,146,417 | A | 11/2000 | Ischinger |
| 6,159,244 | A | 12/2000 | Suddaby |
| 6,159,245 | A | 12/2000 | Meriwether et al. |
| 6,168,616 | B1 | 1/2001 | Brown, III |
| 6,171,312 | B1 | 1/2001 | Beaty |
| 6,176,882 | B1 | 1/2001 | Biedermann et al. |
| 6,179,874 | B1 | 1/2001 | Cauthen |
| 6,183,506 | B1 | 2/2001 | Penn et al. |
| 6,183,517 | B1 | 2/2001 | Suddaby |
| 6,193,757 | B1 * | 2/2001 | Foley et al. .................. 623/17.16 |
| 6,206,910 | B1 | 3/2001 | Berry et al. |
| 6,206,924 | B1 | 3/2001 | Timm |
| 6,224,595 | B1 | 5/2001 | Michelson |
| 6,224,603 | B1 | 5/2001 | Marino |
| 6,224,604 | B1 | 5/2001 | Suddaby |
| 6,224,607 | B1 | 5/2001 | Michelson |
| 6,228,060 | B1 | 5/2001 | Howell |
| 6,245,101 | B1 | 6/2001 | Drasler et al. |
| 6,245,107 | B1 | 6/2001 | Ferree |
| 6,280,456 | B1 | 8/2001 | Scribner et al. |
| 6,287,332 | B1 | 9/2001 | Bolz et al. |
| 6,293,967 | B1 | 9/2001 | Shanley |
| 6,302,914 | B1 | 10/2001 | Michelson |
| 6,332,895 | B1 * | 12/2001 | Suddaby .................. 623/17.11 |
| 6,371,989 | B1 | 4/2002 | Chauvin et al. |
| 6,395,031 | B1 | 5/2002 | Foley et al. |
| 6,402,750 | B1 | 6/2002 | Atkinson et al. |
| 6,402,785 | B1 | 6/2002 | Zdeblick et al. |
| 6,409,765 | B1 | 6/2002 | Bianchi et al. |
| 6,419,704 | B1 | 7/2002 | Ferree |
| 6,419,705 | B1 | 7/2002 | Erickson |
| 6,423,083 | B2 | 7/2002 | Reiley et al. |
| 6,425,916 | B1 | 7/2002 | Garrison et al. |
| 6,425,919 | B1 | 7/2002 | Lambrecht |
| 6,428,569 | B1 | 8/2002 | Brown |
| 6,432,107 | B1 | 8/2002 | Ferree |
| 6,436,098 | B1 | 8/2002 | Michelson |
| 6,436,140 | B1 | 8/2002 | Liu et al. |
| 6,440,168 | B1 | 8/2002 | Cauthen |
| 6,447,544 | B1 | 9/2002 | Michelson |
| 6,447,546 | B1 | 9/2002 | Bramlet et al. |
| 6,447,547 | B1 | 9/2002 | Michelson |
| 6,451,025 | B1 | 9/2002 | Jervis |

(56) References Cited

U.S. PATENT DOCUMENTS

| | | |
|---|---|---|
| 6,454,804 B1 | 9/2002 | Ferree |
| 6,468,301 B1 | 10/2002 | Amplatz et al. |
| 6,468,302 B2 | 10/2002 | Cox et al. |
| 6,478,823 B1 | 11/2002 | Michelson |
| 6,482,235 B1 | 11/2002 | Lambrecht et al. |
| 6,488,710 B2 * | 12/2002 | Besselink .................. 623/17.15 |
| 6,491,724 B1 | 12/2002 | Ferree |
| 6,494,883 B1 | 12/2002 | Ferree |
| 6,508,839 B1 | 1/2003 | Lambrecht et al. |
| 6,514,255 B1 | 2/2003 | Ferree |
| 6,520,991 B2 | 2/2003 | Huene |
| 6,533,817 B1 | 3/2003 | Norton et al. |
| 6,554,833 B2 | 4/2003 | Levy et al. |
| 6,562,074 B2 | 5/2003 | Gerbec et al. |
| 6,582,431 B1 | 6/2003 | Ray |
| 6,582,467 B1 | 6/2003 | Teitelbaum et al. |
| 6,585,770 B1 | 7/2003 | White et al. |
| 6,592,589 B2 | 7/2003 | Hajianpour |
| 6,592,625 B2 | 7/2003 | Cauthen |
| 6,595,998 B2 | 7/2003 | Johnson et al. |
| 6,602,291 B1 | 8/2003 | Ray et al. |
| 6,607,530 B1 | 8/2003 | Carl et al. |
| 6,607,544 B1 | 8/2003 | Boucher et al. |
| 6,613,054 B2 | 9/2003 | Scribner et al. |
| 6,623,505 B2 | 9/2003 | Scribner et al. |
| 6,641,587 B2 | 11/2003 | Scribner et al. |
| 6,641,614 B1 | 11/2003 | Wagner et al. |
| 6,645,213 B2 | 11/2003 | Sand et al. |
| 6,645,247 B2 | 11/2003 | Ferree |
| 6,648,917 B2 | 11/2003 | Gerbec et al. |
| 6,648,918 B2 | 11/2003 | Ferree |
| 6,648,920 B2 | 11/2003 | Ferree |
| 6,652,584 B2 | 11/2003 | Michelson |
| 6,656,178 B1 | 12/2003 | Veldhuizen et al. |
| 6,663,647 B2 | 12/2003 | Reiley et al. |
| 6,666,891 B2 | 12/2003 | Boehm, Jr. et al. |
| 6,679,915 B1 | 1/2004 | Cauthen |
| 6,685,695 B2 | 2/2004 | Ferree |
| 6,695,760 B1 | 2/2004 | Winkler et al. |
| 6,706,068 B2 | 3/2004 | Ferree |
| 6,706,070 B1 | 3/2004 | Wagner et al. |
| 6,709,458 B2 | 3/2004 | Michelson |
| 6,712,853 B2 | 3/2004 | Kuslich |
| 6,716,216 B1 | 4/2004 | Boucher et al. |
| 6,716,247 B2 | 4/2004 | Michelson |
| 6,719,773 B1 | 4/2004 | Boucher et al. |
| 6,723,126 B1 | 4/2004 | Berry |
| 6,726,691 B2 | 4/2004 | Osorio et al. |
| 6,733,535 B2 | 5/2004 | Michelson |
| 6,743,255 B2 | 6/2004 | Ferree |
| 6,746,451 B2 | 6/2004 | Middleton et al. |
| 6,758,863 B2 | 7/2004 | Estes et al. |
| 6,793,656 B1 | 9/2004 | Mathews |
| 6,793,679 B2 | 9/2004 | Michelson |
| 6,808,537 B2 | 10/2004 | Michelson |
| 6,814,756 B1 | 11/2004 | Michelson |
| 6,830,589 B2 * | 12/2004 | Erickson .................. 623/17.15 |
| 6,852,115 B2 | 2/2005 | Kinnett |
| 6,852,123 B2 | 2/2005 | Brown |
| 6,852,129 B2 | 2/2005 | Gerbec et al. |
| 6,863,673 B2 | 3/2005 | Gerbec et al. |
| 6,893,464 B2 | 5/2005 | Kiester |
| 6,899,716 B2 | 5/2005 | Baldwin |
| 6,923,830 B2 | 8/2005 | Michelson |
| 6,936,070 B1 | 8/2005 | Muhanna |
| 6,953,477 B2 | 10/2005 | Berry |
| 6,955,691 B2 | 10/2005 | Chae et al. |
| 6,960,215 B2 | 11/2005 | Olson et al. |
| 6,962,606 B2 | 11/2005 | Michelson |
| 7,008,453 B1 | 3/2006 | Michelson |
| 7,018,415 B1 | 3/2006 | McKay |
| 7,018,416 B2 | 3/2006 | Hanson et al. |
| 7,056,321 B2 | 6/2006 | Pagliuca et al. |
| 7,060,073 B2 | 6/2006 | Frey et al. |
| 7,066,961 B2 | 6/2006 | Michelson |
| 7,077,864 B2 | 7/2006 | Byrd et al. |
| 7,087,055 B2 | 8/2006 | Lim et al. |
| 7,094,257 B2 | 8/2006 | Mujwid et al. |
| 7,097,648 B1 * | 8/2006 | Globerman et al. ............ 606/99 |
| 7,112,206 B2 | 9/2006 | Michelson |
| 7,118,598 B2 | 10/2006 | Michelson |
| 7,135,043 B2 | 11/2006 | Nakahara et al. |
| 7,166,110 B2 | 1/2007 | Yundt |
| 7,201,751 B2 | 4/2007 | Zucherman et al. |
| 7,201,775 B2 | 4/2007 | Gorensek et al. |
| 7,204,853 B2 | 4/2007 | Gordon et al. |
| 7,211,112 B2 | 5/2007 | Baynham et al. |
| 7,212,480 B2 | 5/2007 | Shoji et al. |
| 7,223,292 B2 | 5/2007 | Messerli et al. |
| 7,226,475 B2 | 6/2007 | Lenz et al. |
| 7,226,481 B2 | 6/2007 | Kuslich |
| 7,226,483 B2 | 6/2007 | Gerber et al. |
| 7,238,186 B2 | 7/2007 | Zdeblick et al. |
| 7,241,276 B2 | 7/2007 | Argentine et al. |
| 7,241,297 B2 | 7/2007 | Shaolian et al. |
| 7,241,303 B2 | 7/2007 | Reiss et al. |
| 7,300,440 B2 | 11/2007 | Zdeblick et al. |
| 7,309,338 B2 | 12/2007 | Cragg |
| 7,311,713 B2 | 12/2007 | Johnson et al. |
| 7,316,714 B2 | 1/2008 | Gordon et al. |
| 7,318,826 B2 | 1/2008 | Teitelbaum et al. |
| 7,396,360 B2 | 7/2008 | Lieberman |
| 7,431,735 B2 | 10/2008 | Liu et al. |
| 7,503,933 B2 | 3/2009 | Michelson |
| 7,507,241 B2 | 3/2009 | Levy et al. |
| 7,582,106 B2 * | 9/2009 | Teitelbaum et al. .......... 606/250 |
| 7,601,172 B2 | 10/2009 | Segal et al. |
| 7,618,457 B2 * | 11/2009 | Hudgins .................... 623/17.12 |
| 7,621,950 B1 | 11/2009 | Globerman et al. |
| 7,722,674 B1 | 5/2010 | Grotz |
| 7,749,228 B2 | 7/2010 | Lieberman |
| 7,828,849 B2 | 11/2010 | Lim |
| 7,837,734 B2 | 11/2010 | Zucherman et al. |
| 7,879,036 B2 | 2/2011 | Biedermann et al. |
| 7,879,082 B2 | 2/2011 | Brown |
| 8,105,382 B2 | 1/2012 | Olmos et al. |
| 8,162,943 B2 | 4/2012 | Justin et al. |
| 8,262,737 B2 | 9/2012 | Bagga et al. |
| 2001/0007956 A1 | 7/2001 | Letac et al. |
| 2001/0034552 A1 | 10/2001 | Young et al. |
| 2002/0007218 A1 | 1/2002 | Cauthen |
| 2002/0010511 A1 | 1/2002 | Michelson |
| 2002/0022887 A1 | 2/2002 | Huene |
| 2002/0032444 A1 | 3/2002 | Mische |
| 2002/0052656 A1 | 5/2002 | Michelson |
| 2002/0068911 A1 | 6/2002 | Chan |
| 2002/0068939 A1 | 6/2002 | Levy et al. |
| 2002/0068975 A1 | 6/2002 | Teitelbaum et al. |
| 2002/0068976 A1 | 6/2002 | Jackson |
| 2002/0068977 A1 | 6/2002 | Jackson |
| 2002/0082598 A1 | 6/2002 | Teitelbaum |
| 2002/0082600 A1 | 6/2002 | Shaolian et al. |
| 2002/0091390 A1 | 7/2002 | Michelson |
| 2002/0095155 A1 | 7/2002 | Michelson |
| 2002/0099378 A1 | 7/2002 | Michelson |
| 2002/0111688 A1 | 8/2002 | Cauthen |
| 2002/0120337 A1 | 8/2002 | Cauthen |
| 2002/0123807 A1 | 9/2002 | Cauthen |
| 2002/0128713 A1 | 9/2002 | Ferree |
| 2002/0138077 A1 | 9/2002 | Ferree |
| 2002/0138133 A1 | 9/2002 | Lenz et al. |
| 2002/0138144 A1 | 9/2002 | Michelson |
| 2002/0143401 A1 | 10/2002 | Michelson |
| 2002/0151896 A1 | 10/2002 | Ferree |
| 2002/0151980 A1 | 10/2002 | Cauthen |
| 2002/0156530 A1 | 10/2002 | Lambrecht et al. |
| 2002/0161367 A1 | 10/2002 | Ferree |
| 2002/0161373 A1 | 10/2002 | Osorio et al. |
| 2002/0165542 A1 | 11/2002 | Ferree |
| 2002/0189622 A1 | 12/2002 | Cauthen et al. |
| 2002/0198526 A1 | 12/2002 | Shaolian et al. |
| 2003/0004511 A1 | 1/2003 | Ferree |
| 2003/0004574 A1 | 1/2003 | Ferree |
| 2003/0009227 A1 | 1/2003 | Lambrecht et al. |

(56) References Cited

U.S. PATENT DOCUMENTS

| | | |
|---|---|---|
| 2003/0014118 A1 | 1/2003 | Lambrecht et al. |
| 2003/0026788 A1 | 2/2003 | Ferree |
| 2003/0032963 A1 | 2/2003 | Reiss et al. |
| 2003/0040796 A1 | 2/2003 | Ferree |
| 2003/0040798 A1 | 2/2003 | Michelson |
| 2003/0050701 A1 | 3/2003 | Michelson |
| 2003/0065394 A1 | 4/2003 | Michelson |
| 2003/0065396 A1 | 4/2003 | Michelson |
| 2003/0074076 A1 | 4/2003 | Ferree et al. |
| 2003/0078579 A1 | 4/2003 | Ferree |
| 2003/0088249 A1 | 5/2003 | Furderer |
| 2003/0120345 A1 | 6/2003 | Cauthen |
| 2003/0125748 A1 | 7/2003 | Li et al. |
| 2003/0125807 A1 | 7/2003 | Lambrecht et al. |
| 2003/0135220 A1 | 7/2003 | Cauthen |
| 2003/0135279 A1 | 7/2003 | Michelson |
| 2003/0149482 A1 | 8/2003 | Michelson |
| 2003/0153976 A1 | 8/2003 | Cauthen et al. |
| 2003/0158553 A1 | 8/2003 | Michelson |
| 2003/0158604 A1 | 8/2003 | Cauthen et al. |
| 2003/0163200 A1 | 8/2003 | Cauthen |
| 2003/0181979 A1 | 9/2003 | Ferree |
| 2003/0181980 A1 | 9/2003 | Berry et al. |
| 2003/0181983 A1 | 9/2003 | Cauthen |
| 2003/0187507 A1 | 10/2003 | Cauthen |
| 2003/0187508 A1 | 10/2003 | Cauthen |
| 2003/0191536 A1 | 10/2003 | Ferree |
| 2003/0195514 A1 | 10/2003 | Trieu et al. |
| 2003/0195630 A1 | 10/2003 | Ferree |
| 2003/0195631 A1 | 10/2003 | Ferree |
| 2003/0199979 A1 | 10/2003 | McGuckin |
| 2003/0199981 A1 | 10/2003 | Ferree |
| 2003/0204260 A1 | 10/2003 | Ferree |
| 2003/0208270 A9 | 11/2003 | Michelson |
| 2003/0220643 A1 | 11/2003 | Ferree |
| 2003/0220650 A1 | 11/2003 | Major et al. |
| 2003/0220690 A1 | 11/2003 | Cauthen |
| 2003/0220693 A1 | 11/2003 | Cauthen |
| 2003/0220694 A1 | 11/2003 | Cauthen |
| 2003/0233097 A1 | 12/2003 | Ferree |
| 2003/0233148 A1 | 12/2003 | Ferree |
| 2003/0233188 A1 | 12/2003 | Jones |
| 2003/0236520 A1 | 12/2003 | Lim et al. |
| 2004/0002759 A1 | 1/2004 | Ferree |
| 2004/0002760 A1 | 1/2004 | Boyd et al. |
| 2004/0002769 A1 | 1/2004 | Ferree |
| 2004/0006341 A1 | 1/2004 | Shaolian et al. |
| 2004/0006344 A1 | 1/2004 | Nguyen et al. |
| 2004/0010315 A1* | 1/2004 | Song ............ 623/17.16 |
| 2004/0010318 A1 | 1/2004 | Ferree |
| 2004/0019386 A1 | 1/2004 | Ferree |
| 2004/0024400 A1 | 2/2004 | Michelson |
| 2004/0024459 A1 | 2/2004 | Ferree |
| 2004/0024460 A1 | 2/2004 | Ferree |
| 2004/0024461 A1 | 2/2004 | Ferree |
| 2004/0024462 A1 | 2/2004 | Ferree et al. |
| 2004/0024469 A1 | 2/2004 | Ferree |
| 2004/0024471 A1 | 2/2004 | Ferree |
| 2004/0028718 A1 | 2/2004 | Ferree |
| 2004/0030387 A1 | 2/2004 | Landry et al. |
| 2004/0030389 A1 | 2/2004 | Ferree |
| 2004/0030390 A1 | 2/2004 | Ferree |
| 2004/0030391 A1 | 2/2004 | Ferree |
| 2004/0030398 A1 | 2/2004 | Ferree |
| 2004/0034357 A1 | 2/2004 | Beane et al. |
| 2004/0044410 A1 | 3/2004 | Ferree et al. |
| 2004/0049289 A1 | 3/2004 | Tordy et al. |
| 2004/0059418 A1 | 3/2004 | McKay et al. |
| 2004/0059419 A1 | 3/2004 | Michelson |
| 2004/0059429 A1 | 3/2004 | Amin et al. |
| 2004/0068259 A1 | 4/2004 | Michelson |
| 2004/0082954 A1 | 4/2004 | Teitelbaum et al. |
| 2004/0082961 A1 | 4/2004 | Teitelbaum |
| 2004/0087950 A1 | 5/2004 | Teitelbaum |
| 2004/0092933 A1 | 5/2004 | Shaolian et al. |
| 2004/0092988 A1 | 5/2004 | Shaolian et al. |
| 2004/0097927 A1 | 5/2004 | Yeung et al. |
| 2004/0111108 A1 | 6/2004 | Farnan |
| 2004/0133229 A1 | 7/2004 | Lambrecht et al. |
| 2004/0133280 A1 | 7/2004 | Trieu |
| 2004/0138673 A1 | 7/2004 | Lambrecht et al. |
| 2004/0153064 A1 | 8/2004 | Foley et al. |
| 2004/0153065 A1 | 8/2004 | Lim |
| 2004/0153146 A1 | 8/2004 | Lashinski et al. |
| 2004/0167625 A1 | 8/2004 | Beyar et al. |
| 2005/0010292 A1 | 1/2005 | Carrasco |
| 2005/0015152 A1 | 1/2005 | Sweeney |
| 2005/0033431 A1 | 2/2005 | Gordon et al. |
| 2005/0038512 A1 | 2/2005 | Michelson |
| 2005/0043796 A1* | 2/2005 | Grant et al. ............ 623/17.11 |
| 2005/0070911 A1 | 3/2005 | Carrison et al. |
| 2005/0080422 A1 | 4/2005 | Otte et al. |
| 2005/0085910 A1 | 4/2005 | Sweeney |
| 2005/0107863 A1 | 5/2005 | Brown |
| 2005/0113919 A1 | 5/2005 | Cragg et al. |
| 2005/0113928 A1 | 5/2005 | Cragg et al. |
| 2005/0143827 A1 | 6/2005 | Globerman et al. |
| 2005/0182463 A1 | 8/2005 | Hunter et al. |
| 2005/0187558 A1 | 8/2005 | Johnson et al. |
| 2005/0209698 A1 | 9/2005 | Gordon et al. |
| 2005/0228391 A1 | 10/2005 | Levy et al. |
| 2005/0240188 A1 | 10/2005 | Chow et al. |
| 2005/0249776 A1 | 11/2005 | Chen et al. |
| 2005/0261768 A1 | 11/2005 | Trieu |
| 2005/0278023 A1 | 12/2005 | Zwirkoski |
| 2005/0278026 A1 | 12/2005 | Gordon et al. |
| 2005/0278036 A1 | 12/2005 | Leonard et al. |
| 2006/0004455 A1 | 1/2006 | Leonard et al. |
| 2006/0015184 A1 | 1/2006 | Winterbottom et al. |
| 2006/0052788 A1 | 3/2006 | Thelen et al. |
| 2006/0052870 A1 | 3/2006 | Ferree |
| 2006/0058807 A1 | 3/2006 | Landry et al. |
| 2006/0058876 A1 | 3/2006 | McKinley |
| 2006/0058880 A1 | 3/2006 | Wysocki et al. |
| 2006/0085069 A1 | 4/2006 | Kim |
| 2006/0089715 A1 | 4/2006 | Truckai et al. |
| 2006/0100706 A1 | 5/2006 | Shadduck et al. |
| 2006/0106460 A1 | 5/2006 | Messerli et al. |
| 2006/0122701 A1 | 6/2006 | Kiester |
| 2006/0129244 A1 | 6/2006 | Ensign |
| 2006/0142859 A1 | 6/2006 | McLuen |
| 2006/0149349 A1 | 7/2006 | Garbe |
| 2006/0149385 A1 | 7/2006 | McKay |
| 2006/0161261 A1 | 7/2006 | Brown et al. |
| 2006/0178694 A1 | 8/2006 | Greenhalgh et al. |
| 2006/0184188 A1 | 8/2006 | Li et al. |
| 2006/0200166 A1 | 9/2006 | Hanson et al. |
| 2006/0206207 A1 | 9/2006 | Dryer et al. |
| 2006/0235423 A1 | 10/2006 | Cantu |
| 2006/0241764 A1 | 10/2006 | Michelson |
| 2006/0253201 A1 | 11/2006 | McLuen |
| 2006/0264968 A1 | 11/2006 | Frey et al. |
| 2006/0271061 A1 | 11/2006 | Beyar et al. |
| 2006/0287725 A1 | 12/2006 | Miller |
| 2006/0287726 A1 | 12/2006 | Segal et al. |
| 2006/0287727 A1 | 12/2006 | Segal et al. |
| 2006/0287729 A1 | 12/2006 | Segal et al. |
| 2006/0287730 A1 | 12/2006 | Segal et al. |
| 2007/0027363 A1 | 2/2007 | Gannoe et al. |
| 2007/0032791 A1 | 2/2007 | Greenhalgh |
| 2007/0043440 A1 | 2/2007 | William et al. |
| 2007/0055375 A1 | 3/2007 | Ferree |
| 2007/0055377 A1 | 3/2007 | Hanson et al. |
| 2007/0067034 A1 | 3/2007 | Chirico et al. |
| 2007/0093897 A1 | 4/2007 | Gerbec et al. |
| 2007/0093899 A1 | 4/2007 | Dutoit et al. |
| 2007/0112428 A1 | 5/2007 | Lancial |
| 2007/0118222 A1 | 5/2007 | Lang |
| 2007/0162044 A1 | 7/2007 | Marino |
| 2007/0162135 A1 | 7/2007 | Segal et al. |
| 2007/0173824 A1 | 7/2007 | Rosen |
| 2007/0173830 A1 | 7/2007 | Rosen |
| 2007/0173939 A1 | 7/2007 | Kim et al. |
| 2007/0173940 A1 | 7/2007 | Hestad et al. |

(56) References Cited

U.S. PATENT DOCUMENTS

| | | |
|---|---|---|
| 2007/0208423 A1 | 9/2007 | Messerli et al. |
| 2007/0213717 A1 | 9/2007 | Trieu et al. |
| 2007/0225703 A1 | 9/2007 | Schmitz et al. |
| 2007/0233260 A1 | 10/2007 | Cragg |
| 2007/0239162 A1 | 10/2007 | Bhatnagar et al. |
| 2007/0244485 A1 | 10/2007 | Greenhalgh et al. |
| 2007/0255408 A1 | 11/2007 | Castleman et al. |
| 2007/0255409 A1 | 11/2007 | Dickson et al. |
| 2007/0260315 A1 | 11/2007 | Foley et al. |
| 2007/0270956 A1 | 11/2007 | Heinz |
| 2007/0270968 A1 | 11/2007 | Baynham et al. |
| 2007/0276377 A1 | 11/2007 | Yundt |
| 2007/0288028 A1 | 12/2007 | Gorensek et al. |
| 2008/0015694 A1 | 1/2008 | Tribus |
| 2008/0021558 A1 | 1/2008 | Thramann |
| 2008/0021559 A1 | 1/2008 | Thramann |
| 2008/0071356 A1 | 3/2008 | Greenhalgh et al. |
| 2008/0077150 A1 | 3/2008 | Nguyen |
| 2008/0140207 A1 | 6/2008 | Olmos et al. |
| 2008/0147193 A1 | 6/2008 | Matthis et al. |
| 2008/0147194 A1 | 6/2008 | Grotz et al. |
| 2008/0183204 A1 | 7/2008 | Greenhalgh et al. |
| 2008/0188941 A1 | 8/2008 | Grotz |
| 2008/0221687 A1 | 9/2008 | Viker |
| 2008/0243254 A1 | 10/2008 | Butler |
| 2008/0249625 A1 | 10/2008 | Waugh et al. |
| 2008/0294205 A1 | 11/2008 | Greenhalgh et al. |
| 2008/0312744 A1 | 12/2008 | Vresilovic et al. |
| 2009/0018524 A1 | 1/2009 | Greenhalgh et al. |
| 2009/0024204 A1 | 1/2009 | Greenhalgh et al. |
| 2009/0024217 A1* | 1/2009 | Levy et al. .................. 623/17.16 |
| 2009/0076511 A1 | 3/2009 | Osman |
| 2009/0149956 A1 | 6/2009 | Greenhalgh et al. |
| 2009/0163918 A1 | 6/2009 | Levy et al. |
| 2009/0182431 A1 | 7/2009 | Butler et al. |
| 2009/0198338 A1 | 8/2009 | Phan |
| 2009/0234398 A1 | 9/2009 | Chirico et al. |
| 2009/0240335 A1 | 9/2009 | Arcenio et al. |
| 2009/0318928 A1 | 12/2009 | Purcell et al. |
| 2010/0004750 A1 | 1/2010 | Segal et al. |
| 2010/0004751 A1 | 1/2010 | Segal et al. |
| 2010/0016905 A1 | 1/2010 | Greenhalgh et al. |
| 2010/0082109 A1 | 4/2010 | Greenhalgh et al. |
| 2010/0125274 A1 | 5/2010 | Greenhalgh et al. |
| 2010/0262147 A1 | 10/2010 | Siegal et al. |
| 2010/0292796 A1 | 11/2010 | Greenhalgh et al. |
| 2011/0029083 A1 | 2/2011 | Hynes et al. |
| 2011/0054621 A1 | 3/2011 | Lim |
| 2013/0053852 A1 | 2/2013 | Greenhalgh et al. |
| 2013/0085535 A1 | 4/2013 | Greenhalgh et al. |
| 2013/0138214 A1 | 5/2013 | Greenhalgh et al. |

FOREIGN PATENT DOCUMENTS

| | | |
|---|---|---|
| EP | 1804733 | 7/2007 |
| FR | 2874814 | 11/2007 |
| JP | 2000-210315 | 8/2000 |
| JP | 2003-512887 | 4/2003 |
| JP | 2004-511297 | 4/2004 |
| JP | 2004/531355 | 10/2004 |
| JP | 2004-321348 | 11/2004 |
| SU | 662082 | 5/1979 |
| WO | WO 88/03781 | 6/1988 |
| WO | WO 92/14423 | 9/1992 |
| WO | WO 95/31945 | 11/1995 |
| WO | WO 96/03092 | 2/1996 |
| WO | WO 97/30054 | 1/1997 |
| WO | WO 00/30523 | 6/2000 |
| WO | WO 00/44319 | 8/2000 |
| WO | WO 00/44321 | 8/2000 |
| WO | WO 01/32099 | 5/2001 |
| WO | WO 01/78625 | 10/2001 |
| WO | WO 01/95838 | 12/2001 |
| WO | WO 02/13700 | 2/2002 |
| WO | WO 02/32347 | 4/2002 |
| WO | WO 03/003943 | 1/2003 |
| WO | WO 03/003951 | 1/2003 |
| WO | WO 2005/062900 | 7/2005 |
| WO | WO 2005/096975 | 10/2005 |
| WO | WO 2005/120400 | 12/2005 |
| WO | WO 2006/023514 | 3/2006 |
| WO | WO 2006/023671 | 3/2006 |
| WO | WO 2006/026425 | 3/2006 |
| WO | WO 2006/028971 | 3/2006 |
| WO | WO 2006/034396 | 3/2006 |
| WO | WO 2006/034436 | 3/2006 |
| WO | WO 2006/037013 | 4/2006 |
| WO | WO 2006/042334 | 4/2006 |
| WO | WO 2006/050500 | 5/2006 |
| WO | WO 2006/060420 | 6/2006 |
| WO | WO 2006/076712 | 7/2006 |
| WO | WO 2006/086241 | 8/2006 |
| WO | WO 2006/096167 | 9/2006 |
| WO | WO 2006/116761 | 11/2006 |
| WO | WO 2006/132945 | 12/2006 |
| WO | WO 2007/009107 | 1/2007 |
| WO | WO 2007/009123 | 1/2007 |
| WO | WO 2007/016368 | 2/2007 |
| WO | WO 2007/038611 | 4/2007 |
| WO | WO 2007/041698 | 4/2007 |
| WO | WO 2007/047098 | 4/2007 |
| WO | WO 2007/050322 | 5/2007 |
| WO | WO 2007/056433 | 5/2007 |
| WO | WO 2007/062080 | 5/2007 |
| WO | WO 2007/075411 | 7/2007 |
| WO | WO 2007/079021 | 7/2007 |
| WO | WO 2007/084257 | 7/2007 |
| WO | WO 2007/084268 | 7/2007 |
| WO | WO 2007/084810 | 7/2007 |
| WO | WO 2007/100591 | 9/2007 |
| WO | WO 2007/123920 | 11/2007 |
| WO | WO 2007/124130 | 11/2007 |
| WO | WO 2007/126622 | 11/2007 |
| WO | WO 2007/130699 | 11/2007 |
| WO | WO 2007/131026 | 11/2007 |
| WO | WO 2007/133608 | 11/2007 |
| WO | WO 2007/140382 | 12/2007 |
| WO | WO 2008/005627 | 1/2008 |
| WO | WO 2008/070863 | 6/2008 |
| WO | WO 2009/114381 | 9/2009 |
| WO | WO 2012/027490 | 3/2012 |
| WO | WO 2013/028808 | 2/2013 |
| WO | WO 2013/119332 | 8/2013 |

OTHER PUBLICATIONS

Pyo, R. et al., "Targeted Gene Disruption of Matrix Metalloproteinase-9 (Gelatinase B) Suppresses Development of Experimental Abdominal Aortic Aneurysms," *J. Clinical Investigation*, 105(11):1641-1649, Jun. 2000.

Tambiah, J. et al., "Provocation of Experimental Aortic Inflammation Mediators and *Chlamydia pneumoniae*," *Brit., J. Surgery*, 88(7).935-940, Feb. 2001.

Walton, L.J. et al., "Inhibition of Prostoglandin E2 Synthesis in Abdonminal Aortic Aneurysms," *Circulation*, 48-54, Jul. 6, 1999.

Xu, Q. et al "Sp1 Increases Expression of Cyclooxygenase-2 in Hypoxic Vascular Endothelium," *J. Biological Chemistr*, 275(32):24583-24589, Aug. 2000.

European Patent Application No. 05799664.7 filed Sep. 26, 2005 in the name of Greenhalgh et al., Office Action mailed Mar. 30, 2010.

Japanese Patent Application No. 2008-509225 filed Apr. 27, 2006, Office Action mailed Feb. 12, 2010.

Japanese Patent Application no. 2008-509225 filed Apr. 27, 2006, Office Action mailed Dec. 27, 2010.

PCT International Patent Application No. PCT/US2005/034115 filed Sep. 21, 2005 in the name of Greenhalgh et al., International Search Report and Written Opinion mailed Aug. 29, 2006.

PCT International Patent Application No. PCT/US2005/034115 filed Sep. 21, 2005 in the name of Greenhalgh et al., International Preliminary Report on Patentability mailed Apr. 5, 2007.

(56) References Cited

OTHER PUBLICATIONS

PCT International Patent Application No. PCT/US2009/064249 filed Nov. 12, 2009 in the name of Greenhalgh et al., International Search Report and Written Opinion mailed Feb. 3, 2010.

PCT International Patent Application No. PCT/US2010/034788 filed May 13, 2010 in the name of Greenhalgh et al., International Search Report mailed Jul. 8, 2010.

PCT International Patent Application No. PCT/US2010/035009 filed May 14, 2010 in the name of Greenhalgh et al., International Search Report mailed Jul. 16, 2010.

U.S. Appl. No. 11/689,465, filed Mar. 21, 2007 in the name of Greenhalgh et al., Final Office Action mailed Jan. 19, 2011.

U.S. Appl. No. 11/689,465, filed Mar. 21, 2007 in the name of Greenhalgh et al., Non-Final Office Action mailed Aug. 10, 2010.

U.S. Appl. No. 11/877,610, filed Oct. 23, 2007 in the name of Greenhalgh et al., Final Office Action mailed Dec. 20, 2010.

U.S. Appl. No. 11/877,610 filed Oct. 23, 2007 in the name of Greenhalgh et al., Non-Final Office Action mailed Jul. 9, 2010.

U.S. Appl. No. 12/014,006, filed Jan. 14, 2008 in the name of Greenhalgh et al., Non-final Office Action mailed Mar. 23, 2011.

U.S. Appl. No. 12/139,367, filed Jun. 13, 2008 in the name of Greenhalgh et al., Non-Final Office Action mailed Aug. 4, 2010.

U.S. Appl. No. 12/139,367, filed Jun. 13, 2008 in the name of Greenhalgh et al., Non-Final Office Action mailed Mar. 31, 2009.

U.S. Appl. No. 12/139,396, filed Jun. 13, 2008 in the name of Greenhalgh et al., Non-Final Office Action mailed Sep. 2, 2010.

U.S. Appl. No. 12/693,382, filed Jan. 25, 2010 in the name of Greenhalgh et al., Final Office Action mailed Mar. 21, 2011.

U.S. Appl. No. 12/693,382, filed Jan. 25, 2010 in the name of Greenhalgh et al., Non-Final Office Action mailed Sep. 2, 2010.

Databae WPI, Week 198004, Thomas Scientific, London,GB: AN 1980-A8866C, XP002690114, -& SU 662 082 A1 (Tartus Univ) May 15, 1979, abstract, figures 1,2.

* cited by examiner

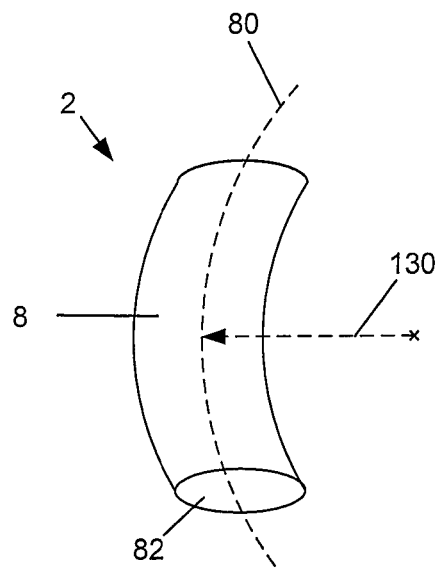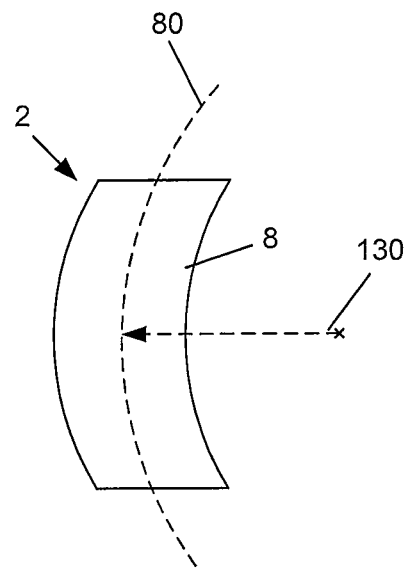
Fig. 48    Fig. 49
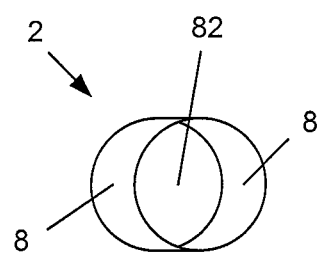
Fig. 50

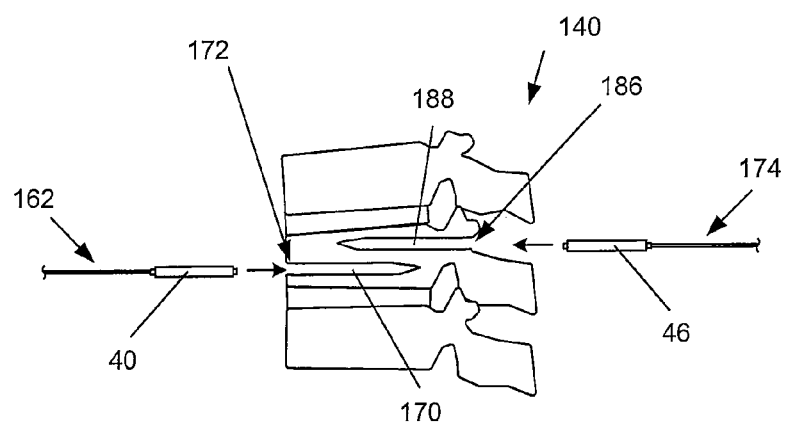
Fig. 63
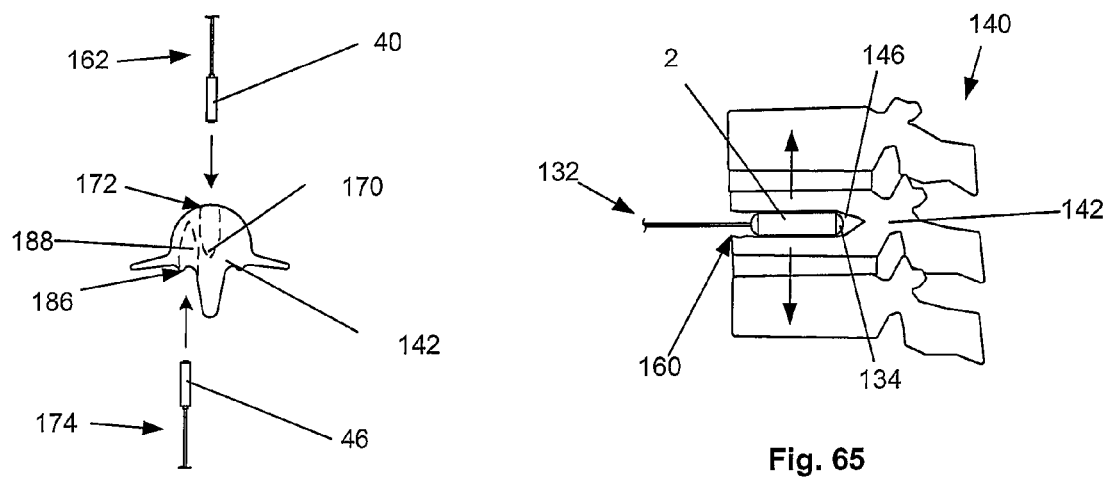
Fig. 64
Fig. 65

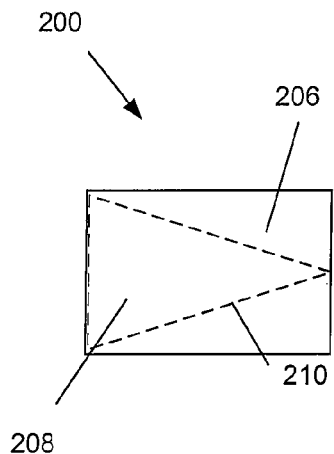
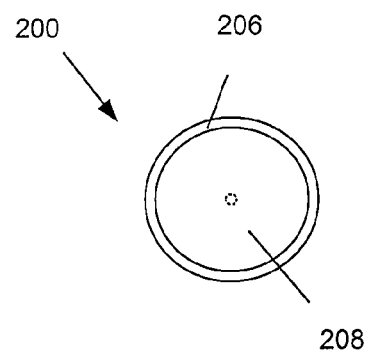
Fig. 92
Fig. 93
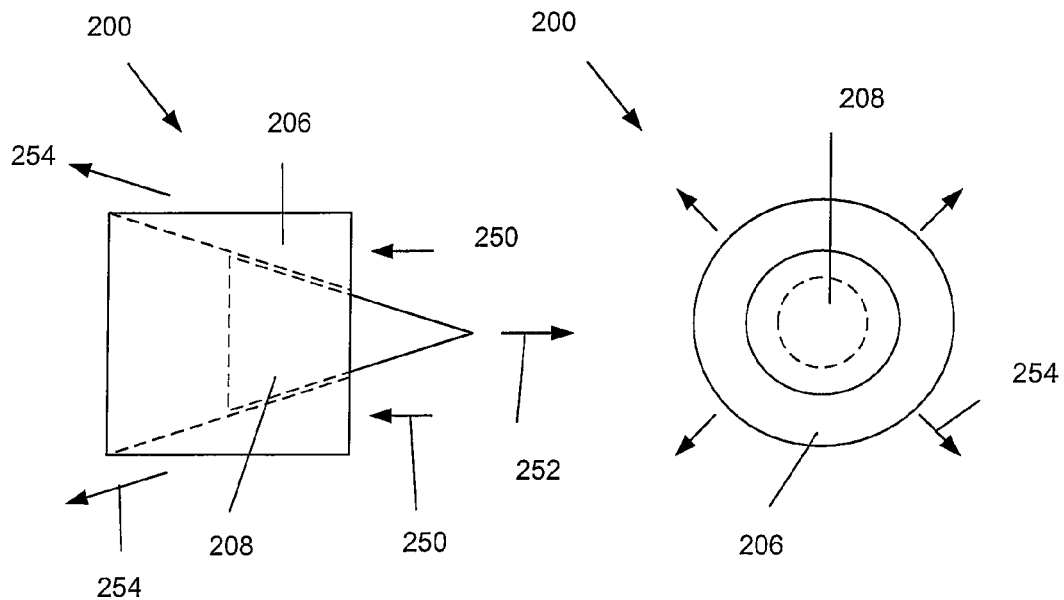
Fig. 94
Fig. 95

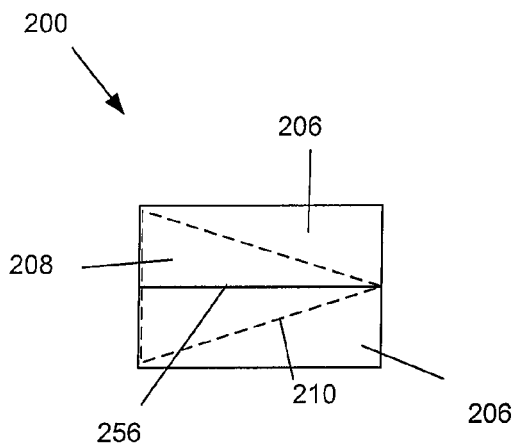
Fig. 96
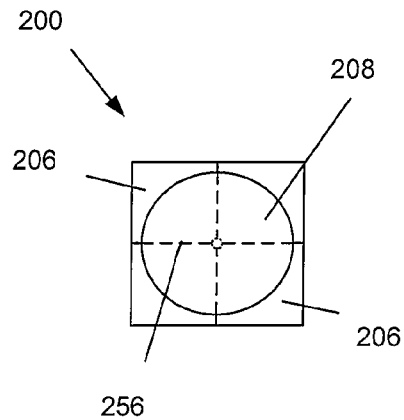
Fig. 97
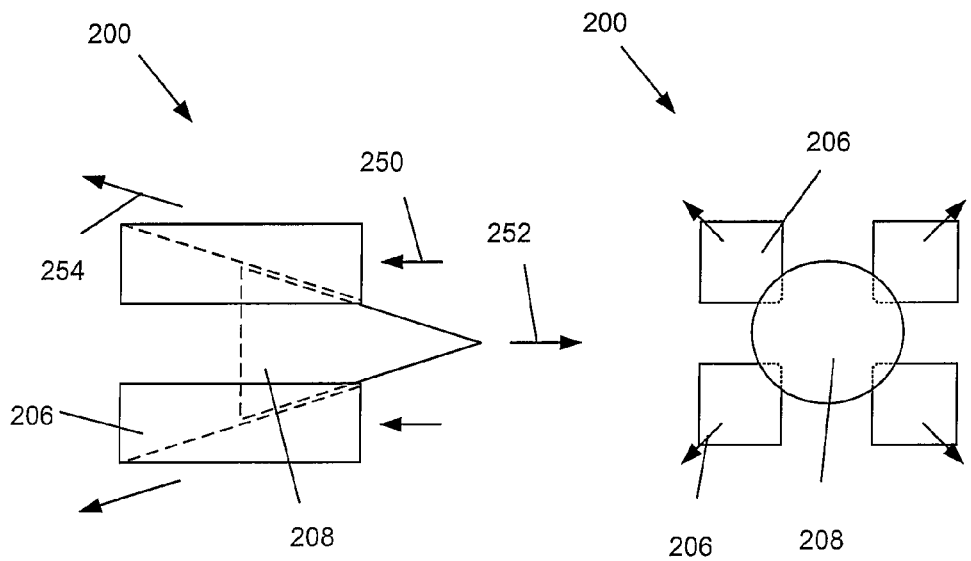
Fig. 98
Fig. 99

EXPANDABLE SUPPORT DEVICE AND METHOD OF USE

CROSS-REFERENCE TO RELATED APPLICATIONS

This application is a continuation-in-part of PCT Application No. PCT/US2005/037126, filed Oct. 12, 2005 which claims priority to U.S. Provisional Application No. 60/617,810, filed Oct. 12, 2004; a continuation-in-part of PCT Application No. PCT/US2005/034115, filed Sep. 21, 2005, which claims priority to U.S. Provisional Application No. 60/612,001, filed Sep. 21, 2004; and a continuation-in-part of PCT Application No. PCT/US2005/034742, filed Sep. 26, 2005, which claims priority to U.S. Provisional Application No. 60/612,723, filed Sep. 24, 2004, and U.S. Provisional Application No. 60/612,724, filed Sep. 24, 2004, all of which are incorporated by reference herein in their entirety. This application also claims the benefit of all of the above-referenced U.S. Provisional applications.

BACKGROUND OF THE INVENTION

1. Field of the Invention

This invention relates to devices for providing support for biological tissue, for example to fuse vertebral bodies, repair herniated discs, and/or repair spinal compression fractures, and methods of using the same.

2. Description of Related Art

Some conditions of the spine result from degradation or injury to the bone structures of the spine, typically the vertebral body. These can be the result of bone degeneration such as through osteoporosis or trauma, such as compression fractures. breakdown or injury to the boney structures in the spine can result in pain and spinal deformity with comorbidities.

Vertebroplasty is an image-guided, minimally invasive, nonsurgical therapy used to strengthen a broken vertebra that has been weakened by disease, such as osteoporosis or cancer. Vertebroplasty is often used to treat compression fractures, such as those caused by osteoporosis, cancer, or stress.

Vertebroplasty is often performed on patients too elderly or frail to tolerate open spinal surgery, or with bones too weak for surgical spinal repair. Patients with vertebral damage due to a malignant tumor may sometimes benefit from vertebroplasty. The procedure can also be used in younger patients whose osteoporosis is caused by long-term steroid treatment or a metabolic disorder.

Vertebroplasty can increase the patient's functional abilities, allow a return to the previous level of activity, and prevent further vertebral collapse. Vertebroplasty attempts to also alleviate the pain caused by a compression fracture.

Vertebroplasty is often accomplished by injecting an orthopedic cement mixture through a needle into the fractured bone. The cement mixture can leak from the bone, potentially entering a dangerous location such as the spinal canal. The cement mixture, which is naturally viscous, is difficult to inject through small diameter needles, and thus many practitioners choose to "thin out" the cement mixture to improve cement injection, which ultimately exacerbates the leakage problems. The flow of the cement liquid also naturally follows the path of least resistance once it enters the bone—naturally along the cracks formed during the compression fracture. This further exacerbates the leakage.

The mixture also fills or substantially fills the cavity of the compression fracture and is limited to certain chemical composition, thereby limiting the amount of otherwise beneficial compounds that can be added to the fracture zone to improve healing. In an alternative procedure known as kyphoplasty, a balloon is first inserted in the compression fracture and the vertebra and is expanded to create a void before the cement is injected into the newly formed space.

A vertebroplasty device and method that eliminates or reduces the risks and complexity of the existing art is desired. A vertebroplasty device and method that may reduce or eliminate the need to inject a liquid directly into the compression fracture zone is also desired.

Other ailments of the spine result in degeneration of the spinal disc in the intervertebral space between the vertebral bodies. These include degenerative disc disease and traumatic injuries. In either case, disc degeneration can cause pain and other complications. Conservative treatment can include non-operative treatment requiring patients to adjust their lifestyles and submit to pain relievers and a level of underlying pain. Operative treatment options include disc removal. This can relieve pain in the short term, but also often increases the risk of long-term problems and can result in motor and sensory deficiencies resulting from the surgery. Disc removal and more generally disc degeneration disease are likely to lead to a need for surgical treatment in subsequent years. The fusion or fixation will minimize or substantially eliminate relative motion between the fixed or fused vertebrae. In surgical treatments, adjacent vertebra can be fixated or fused to each other using devices or bone grafts. These may include, for example, screw and rod systems, interbody spacers (e.g., PEEK spacers or allograft bone grafts) threaded fusion cages and the like.

Some fixation or fusion devices are attached to the vertebra from the posterior side. The device will protrude and result in additional length (i.e., needed to overlap the vertebrae) and additional hardware to separately attach to each vertebrae. Fusion cages and allografts are contained within the intervertebral space, but must be inserted into the intervertebral space in the same dimensions as desired to occupy the intervertebral space. This requires that an opening sufficient to allow the cage or graft must be created through surrounding tissue to permit the cage or graft to be inserted into the intervertebral space.

A spinal fixation or fusion device that can be implanted with or without the need for additional hardware is desired. Also desired is a fixation or fusion device that can be deployed in a configuration where overlapping the fixated or fused vertebrae is not required.

Also desired is an intervertebral device the may be inserted in to the intervertebral space at a first smaller dimension and deployed to a second, larger dimension to occupy the intervertebral space. The ability to insert an intervertebral spacer at a dimension smaller than the deployed dimension would permit less disruption of soft and boney tissue in order to access the intervertebral space.

An effective therapy for following up a discectomy is desired. A vertebral fusion technique that can be used subsequent to a discectomy is desired.

SUMMARY OF THE INVENTION

An expandable support device that can be used to repair fractures and stabilize hard tissue, such as via intravertebral or intervertebral deployment, is disclosed. The expandable support device can have a longitudinal axis and a radial axis. The expandable support device can be configured, for example by design of the cells, voids or holes in the wall, to expand radially when compressed longitudinally. The expandable support device can be made from an integral piece of metal.

An expandable support device for performing completely implantable spinal repair is disclosed. The device has a first strut and a second strut attached to, and/or integral with, the first strut. The first strut is substantially deformable. The second strut can be substantially inflexible.

The device can be configured to expand in a single direction. The device can be configured to expand in two directions.

The device can have a buttress. The buttress can have, for example, a coil, a wedge, and/or a hoop.

The device can have a locking pin. The locking pin can be interference fit with the device, for example with the first strut, and/or with a longitudinal port of the device.

Methods for deploying an expandable support device in the spine are disclosed. The expandable support device can be deployed, for example, by longitudinal compression. The longitudinal compression can result in radial expansion of the expandable support device. The expandable support device can be deployed in an intravertebral site. The expandable support device can be deployed in an intervertebral site.

Methods for repairing a damaged section of a spine are also disclosed. The methods include expanding an expandable support device in the damaged section. The expandable support device is loaded on a balloon during the expanding. Expanding includes inflating a balloon. Inflating the balloon includes inflating the balloon equal to or greater than about 5,000 kPa of internal pressure, or equal to or greater than about 10,000 kPa of internal pressure.

Tools for deploying an expandable support device are disclosed. The tools can be configured to apply a compressive force on the expandable support device along the expandable support device's longitudinal axis. The tools can be configured to securely engage the expandable support device. The tools can be configured to removably attach to opposing points at or near opposing longitudinal ends of the expandable support device. Actuation of the tool to apply a compressive force may include squeezing two handles together or rotating a knob or handle.

In all configurations and contemplated uses, the expandable device may be filled with a material suitable for the contemplated use. By way of example, when used to treat compression fractures, it is contemplated that a suitable material such bone cement, tissue or bone growth factors, bone morphogenic proteins, stem cells, carriers for any of the foregoing, or mixtures thereof may be inserted within the expandable device to provide support, fixation and/or improved bone structure. In the case of growth factors or stem cells, it is contemplated these may be obtained autologously, such as from the patient's own blood or bone marrow aspirate. By way of further example, when the device is used as an intervertebral spacer for fusion, it is contemplated that the expandable device may be filled with autograft, allograft, bone extenders (e.g., calcium phosphate or tricalcium phosphate or mixtures thereof or other similar materials), bone growth factors, bone morphogenic proteins, stem cells, carriers for any of the foregoing, and mixtures thereof. As contemplated above, growth factors and stem cells may be commercially available or may be extracted from the patient's own blood or bone marrow aspirate.

In addition, it is contemplated that the ratio of the expansion for the expandable devices (the ratio of the unexpanded height or diameter, depending on configuration, to the expanded height or diameter) may be from 1:2 to 1:5 or greater. For intravertebral and intervertebral applications applicants have found that expansion ratios of from about 1:3 to about 1:4 are acceptable. For vertebroplasty or interbody applications it is contemplated that a device having an initial height or diameter from about 4 mm (0.16 in.) to about 8 mm (0.31 in.) and an expanded height or diameter from about 7 mm (0.28 in.) to about 18 mm (0.71 in.) may be desirable.

BRIEF DESCRIPTION OF THE DRAWINGS

FIG. 48 is a top perspective view of a variation of the expandable support device.

FIG. 49 is top view of the variation of the expandable support device of FIG. 48.

FIG. 50 is a front view of the variation of the expandable support device of FIG. 48.

FIGS. 63 and 64 illustrate a variation of a method for deploying one or more expandable support devices into one or more damage sites in the vertebra.

FIG. 65 illustrates a variation of a method for deploying the expandable support device into the damage site in the vertebra.

FIGS. 92 and 93 show side and front views, respectively, of a variation of the expansion component.

FIGS. 94 and 95 show side and front views, respectively, of a variation of a method for using the variation of the expansion component of FIGS. 92 and 93.

FIGS. 96 and 97 show side and front views, respectively, of a variation of the expansion component.

FIGS. 98 and 99 show side and front views, respectively, of a variation of a method for using the variation of the expansion component of FIGS. 96 and 97.

DETAILED DESCRIPTION

Figure 1:
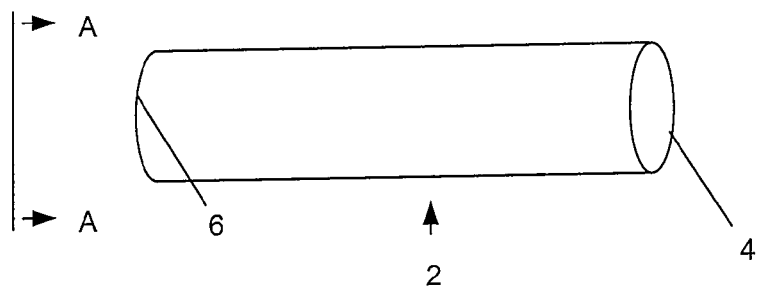
FIGS. 1 through 3 are side perspective views of various variations of the expandable support device.

FIG. 1 illustrates an expandable support device 2, such as a stent, that can be implanted in a bone, such as a compression fracture in a vertebra, in the intervertebral space between two vertebrae, or in soft tissue, such as a herniated intervertebral disc. The expandable support device 2 should be biocompatible. The expandable support device 2 can have one of many configurations, and can be used, for example, for methods of repairing vertebral bone fractures or supporting adjacent vertebral bodies for fusion. The expandable support device 2 can have a first end 4 and a second end 6.

Figure 2:
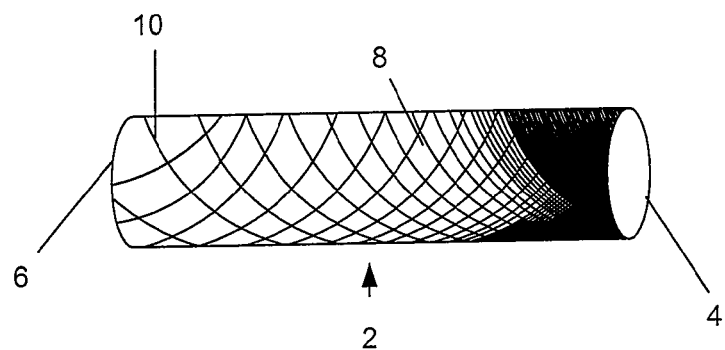

FIG. 2 illustrates that the expandable support device 2 can have a wall 8. The wall 8 can have struts 10. The struts 10 can vary in density along the length of the expandable support device 2 from the first end 4 to the second end 6. The density of the struts 10 can be higher near the first end 4 than near the second end 6 (as shown). The density of the struts 10 can be higher near the second end 6 than near the first end 4. The density of the struts 10 can be higher near the first end 4 and the second end 6 than the middle between the first 4 and second ends 6. Controlling the density, thickness and arrangement of the struts results in controlled deployment and shape of the implant.

Figure 3:
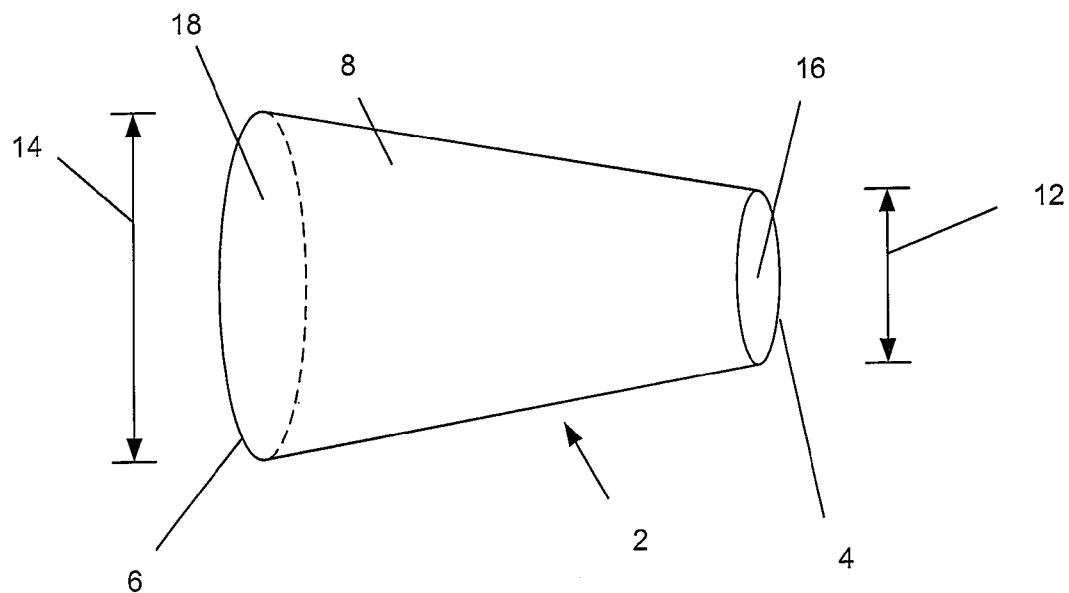

FIG. 3 illustrates that the expandable support device 2 can have a tapered configuration before or after deployment. The first end 4 can have a first diameter 12. The second end 6 can have a second diameter 14. The second diameter 14 can be greater than the first diameter 12 (as shown). The first diameter 12 can be greater than the second diameter 14. The first diameter 12 and second diameters 14 can both be greater than a diameter in the middle of the expandable support device 2 between the first end 4 and second end 6. The tapered configuration can be a result of a greater strength of the expandable support device 2 at or near the tapered section or end of the expandable support device 2. A greater density of struts 10 can be at the first end 4 to achieve this result. The struts 10 at the first end 4 can have a greater strut diameter than the struts 10 at the second end 6. The expandable support device 2 can have a first port 16 at the first end 4. The expandable support device 2 can have a second port 18 at the second end 6.

Figure 4:
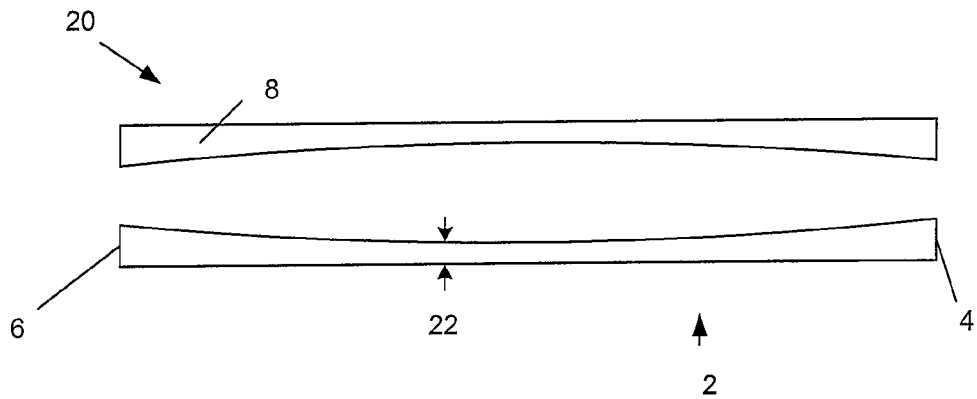
FIGS. 4 through 6 illustrate various variations of cross-section A-A of the expandable support device.

FIG. 4 illustrates that the device in cross-section A-A can have a varying wall thickness 20 along a longitudinal length of the expandable support device 2 from the first end 4 to the second end 6. The wall thickness 20 can be greater at the first 4 and second ends 6 than in the middle of the expandable support device 2 between the first 4 and second ends 6.

Figure 5:
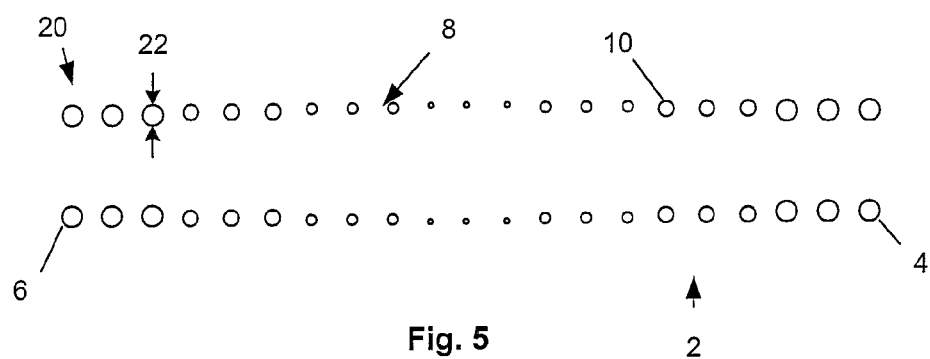
Figure 6:
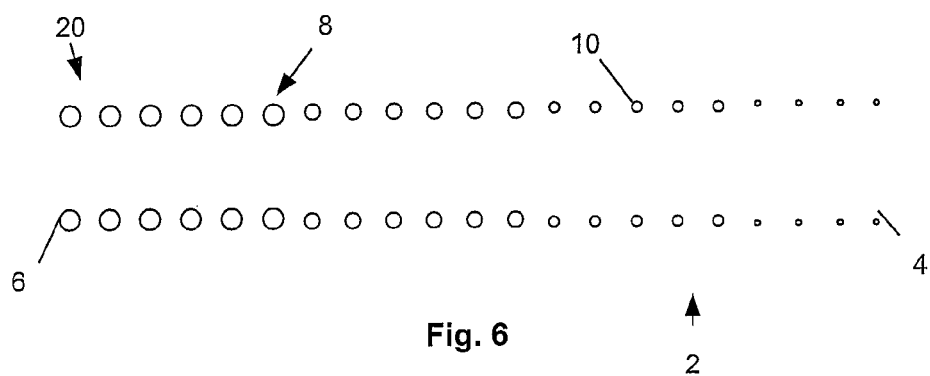

FIG. 5 illustrates that the wall 8 can be made from struts 10. The strut diameters 22 can vary along the length of the expandable support device 2. FIG. 5 illustrates the strut diameters 22 can be greater at the first 4 and second ends 6 than the strut diameters 22 between the first 4 and second ends 6. FIG. 6 illustrates that the strut diameters 22 can be greater at the second end 6 than the strut diameters 22 at the first end 4. The strength of the wall 8 can be adjusted along the length of the expandable support device 2 by designing varying, for example, strut diameters 22, strut cross-sectional areas, strut densities (i.e., strut spacing, number of struts), strut cross-sectional geometries, and combinations thereof.

Figure 7:
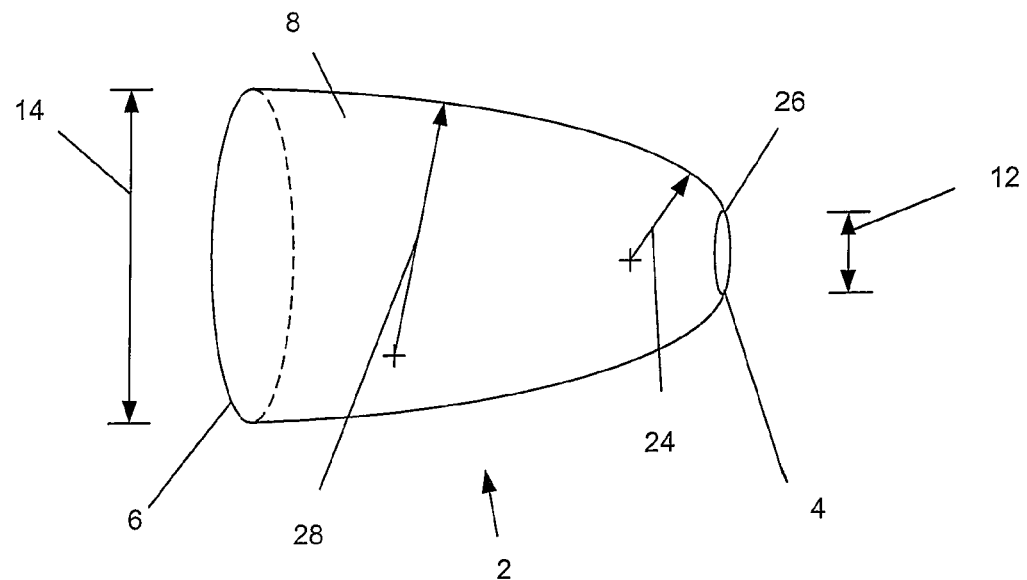
FIG. 7 through 10 are side perspective views of various variations of the expandable support device.

FIG. 7 illustrates that the expandable support device 2 can have a bullet shape. The wall 8 can have a first radius of curvature 24 near or at the first end 4. The first end 4 can have a first rim 26 circumferentially around the first end 4. The wall 8 can have a second radius of curvature 28 near or at the second end 6. The first radius of curvature 24 can be less than the second radius of curvature 28 (as shown). The first radius of curvature 24 can be greater than the second radius of curvature 28. The first and second radii of curvature can be greater than a radius of curvature between the first 4 and second ends 6.

Figure 8:
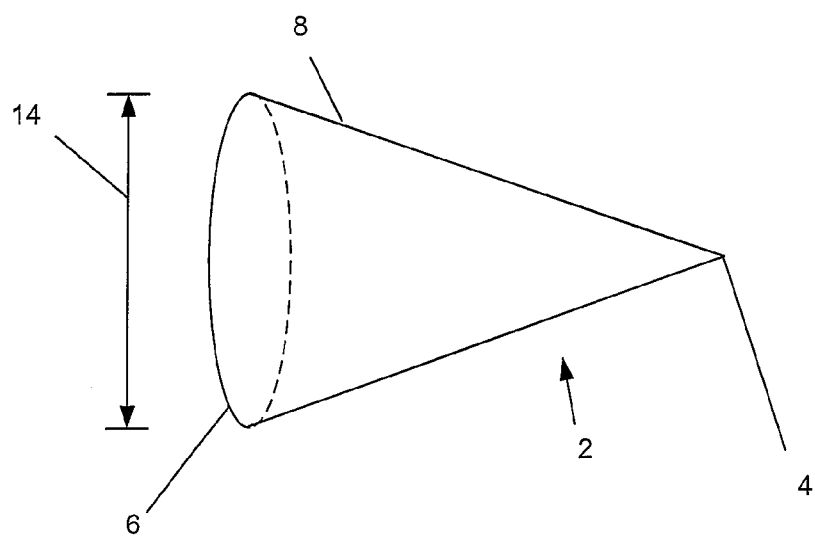

FIG. 8 illustrates that the expandable support device 2 can be sharply pointed at the first end 4 (as shown), and/or second end 6. The first end 4 can have a smaller first port 16 than the second port 18, or no first port 16 (as shown). The first end 4 can be made from, for example, a plastic and/or dense mesh of thick wires.

Figure 9:
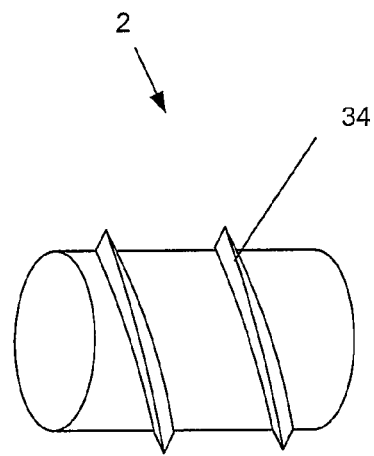

FIG. 9 illustrates that the expandable support device 2 can have a thread 34. The expandable support device 2 can be rotated during implantation to screw into an implant site, such as a vertebra.

Figure 10:
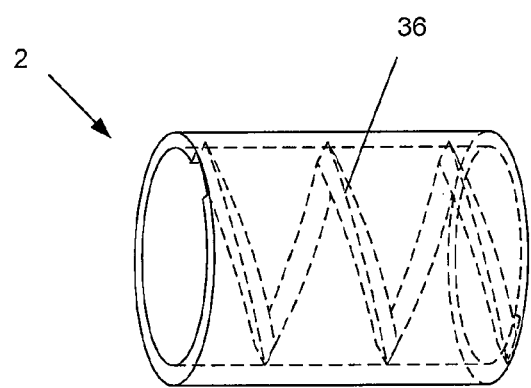

FIG. 10 illustrates an expandable support device 2 that can have an engagement groove 36. The engagement groove 36 can be on the inner diameter of the expandable support device 2. The engagement groove 36 can be configured to engage the external engagement thread on the expansion component.

Figure 11:
FIG. 11 is a side perspective view of a variation of the expandable support device in a contracted configuration.

FIG. 11 illustrates a twistable coil variation of the expandable support device 2 in an untwisted configuration. The untwisted expandable support device 2 can have a contracted diameter 38. The contracted diameter 38 can be less than the expanded diameter of the twistable coil variation of the expandable support device 2. The coils can be resiliently or deformably altered in configuration during untwisting. The coils can resiliently expand when released from the untwisted configuration.

Figure 12:
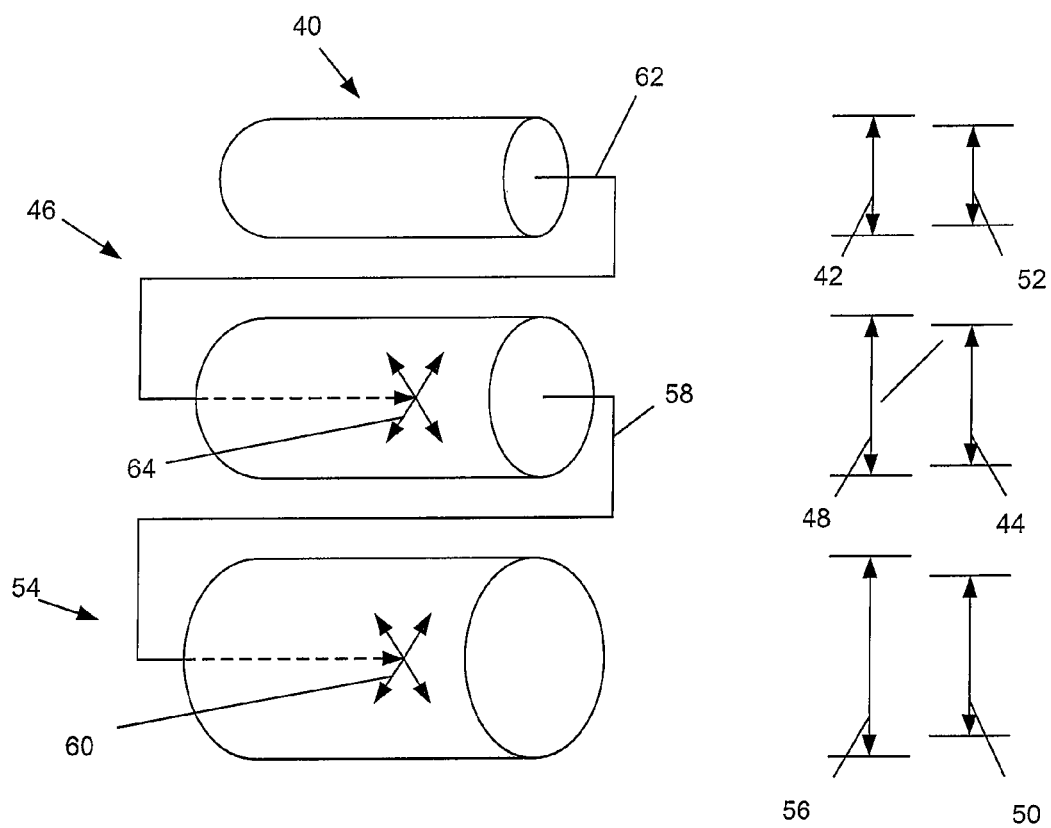
FIGS. 12 through 14 illustrate a variation of a method of deploying multiple expandable support devices.

FIG. 12 illustrates that multiple expandable support devices 2 can each have an outer diameter and an inner diameter in a relaxed configuration. The first expandable support device 40 can have a first device outer diameter 42 that can be equal to or greater, for example by a substantially small amount, than a second device inner diameter 44. The second expandable support device 46 can have a second device outer diameter 48 that can be equal to or greater, for example by a substantially small amount, than a third device inner diameter 50. The first device 40 can have a first device inner diameter 52 and the third device 54 can have a third device outer diameter 56.

Figure 13:
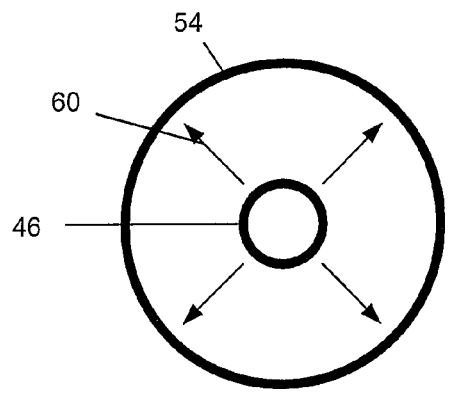

As shown in FIGS. 12 and 13, the third expandable support device 54 can be deployed. The second expandable support device 46 can then be inserted 58 into the third expandable support device 54. The second expandable support device 46 can then be expanded 60 in the third expandable support device 54.

Figure 14:
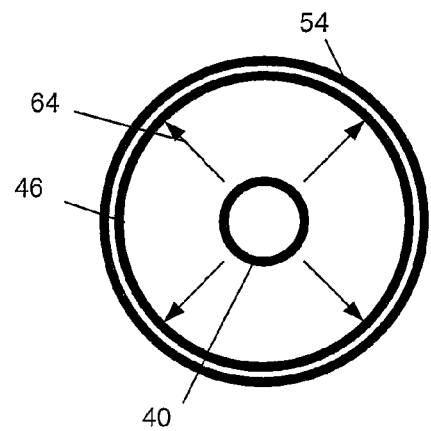

As shown in FIGS. 12 and 14, the first expandable support device 40 can then be inserted 62 into the second expandable support device 46. The first expandable support device 40 can then be expanded 64 into the second expandable support device 46. The concentrically smaller expandable support devices 2 can butt against the next larger expandable support devices 2 (the gap shown in FIG. 14 between the third and second expandable support devices 54 and 46, respectively, is for illustrative purposes). As shown in greater detail below, each expandable support device 2 can support, and/or substantially lock into place, the next larger, abutting, expandable support device 2.

Figure 15:
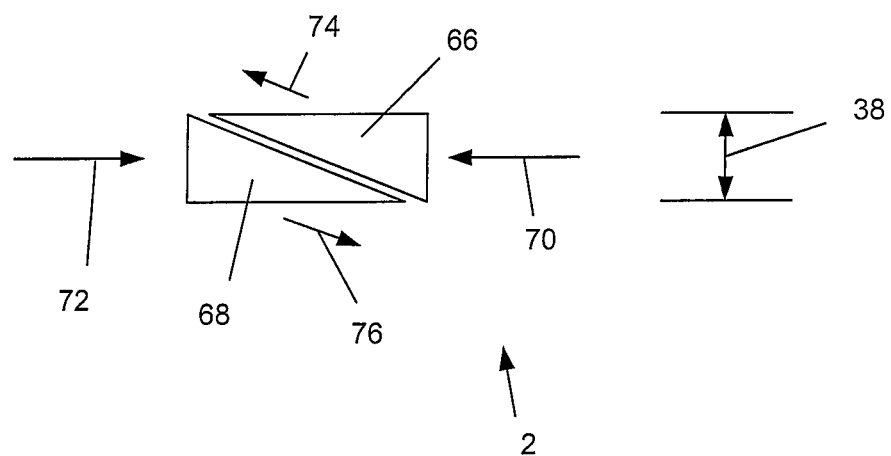
FIG. 15 is a schematic figure of a variation of the expandable support device in a contracted configuration.
Figure 16:
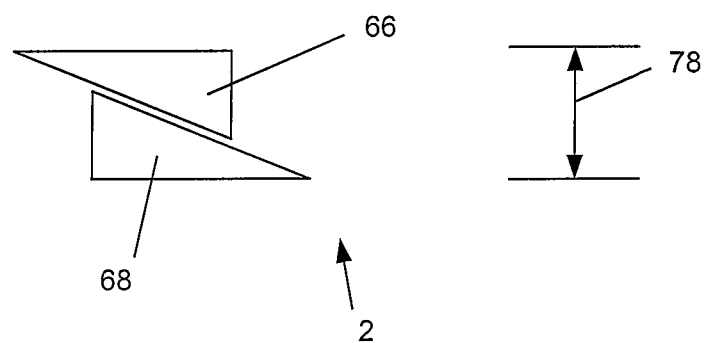
FIG. 16 is a schematic figure of a variation of the expandable support device of FIG. 15 in an expanded configuration.
Figures 17, 18:
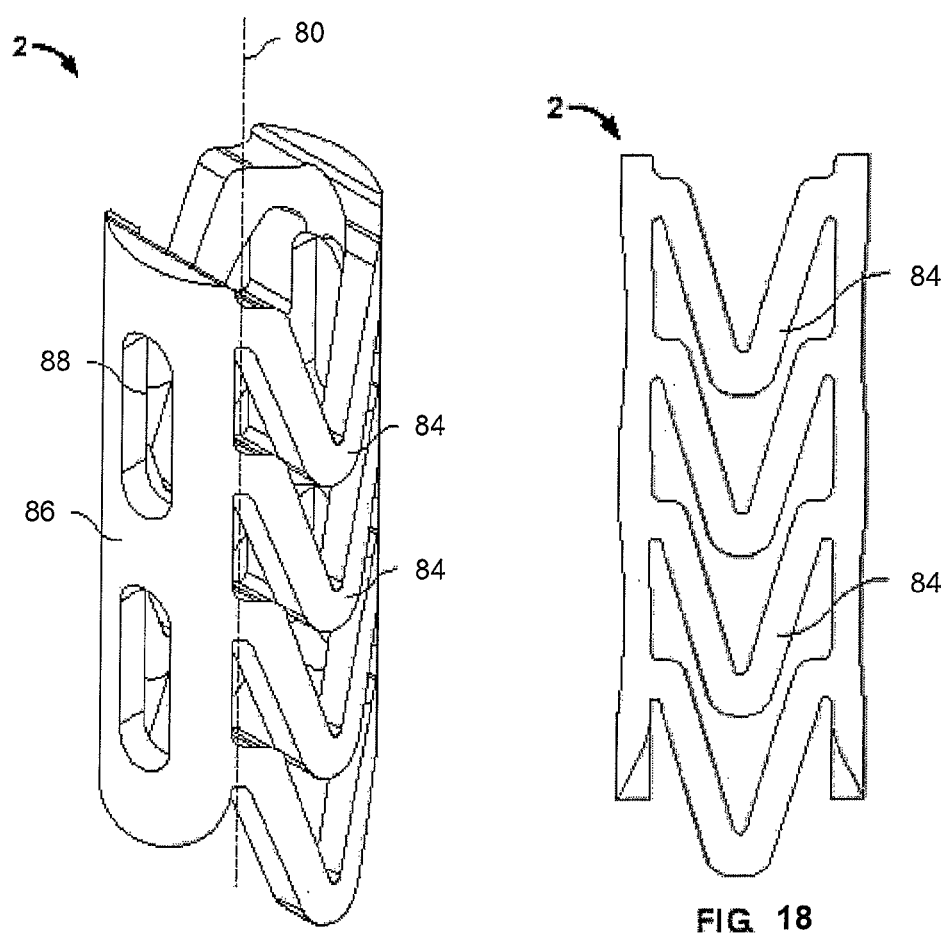
FIG. 17 is a perspective view of a variation of the expandable support device.
FIG. 18 is a side view of the variation of the expandable support device of FIG. 17.
Figure 19:
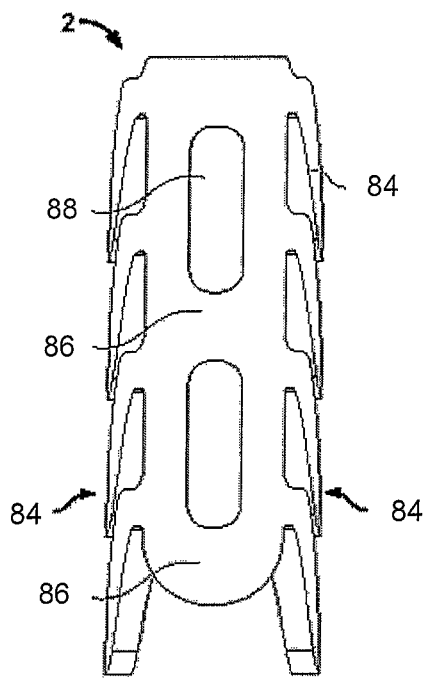
FIG. 19 is a top view of the variation of the expandable support device of FIG. 17.
Figure 20:
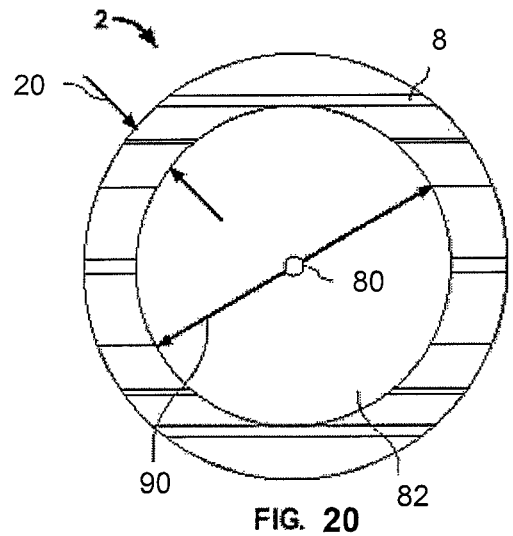
FIG. 20 is a front view of the variation of the expandable support device of FIG. 17.
Figure 133:
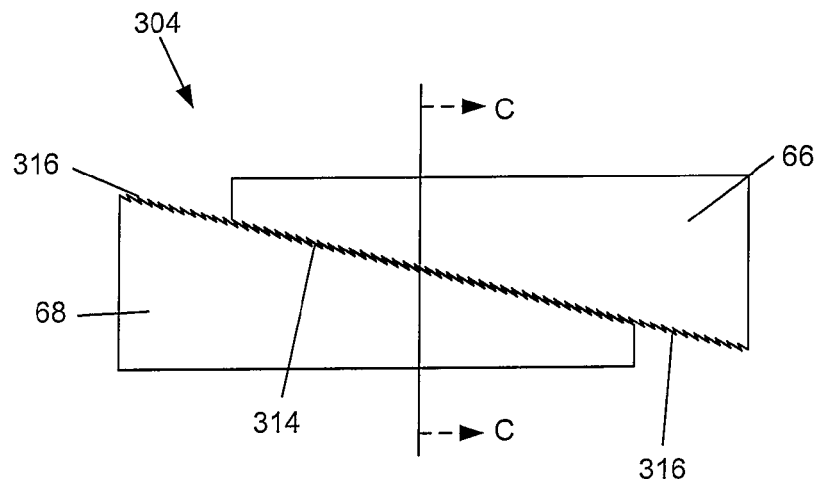
FIG. 133 illustrates a variation of a buttress.
Figure 134:
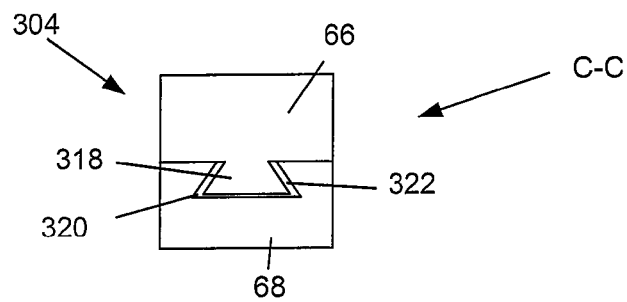
FIG. 134 illustrates a variation of section C-C of the buttress of FIG. 133.
Figure 135:
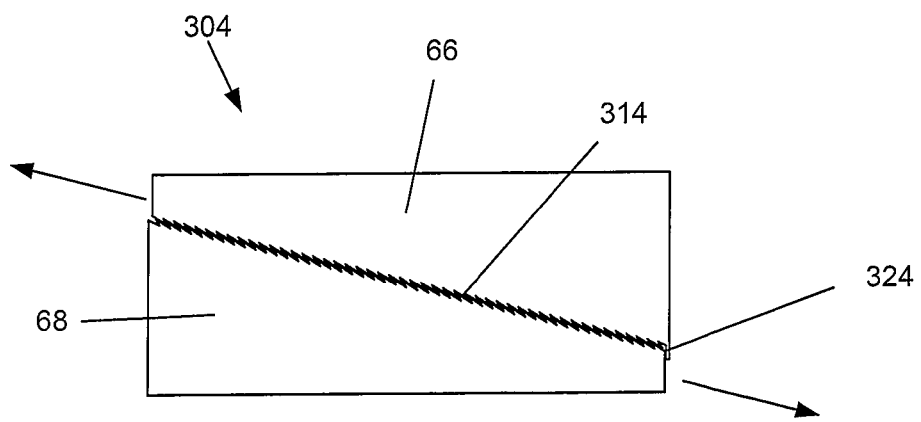
FIG. 135 illustrates a variation of a method for deploying a buttress.
Figure 136:
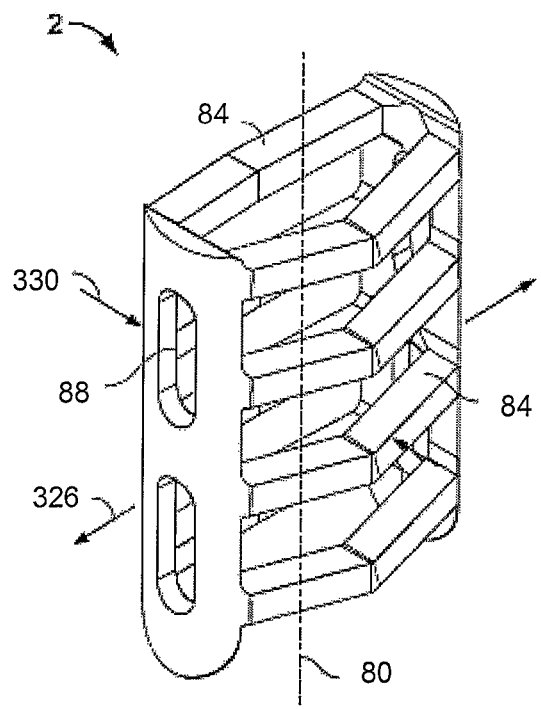
FIGS. 136 through 139 illustrate a method for deploying the expandable support device of FIGS. 17 through 20.
Figure 137:
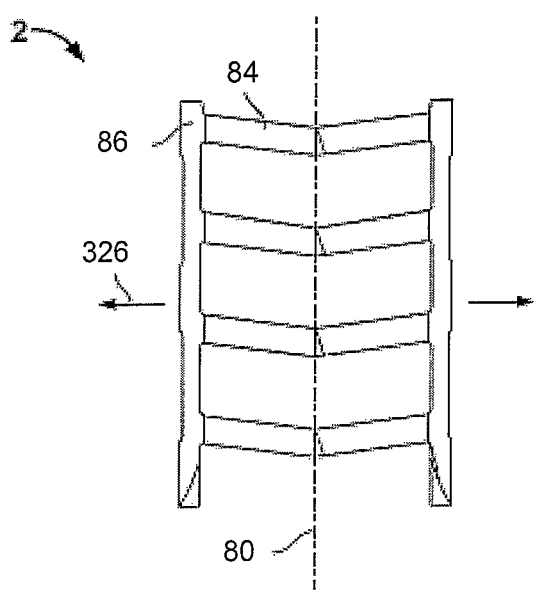
Figure 138:
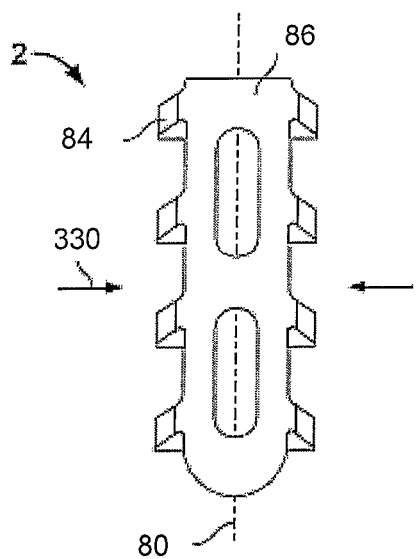
Figure 139:
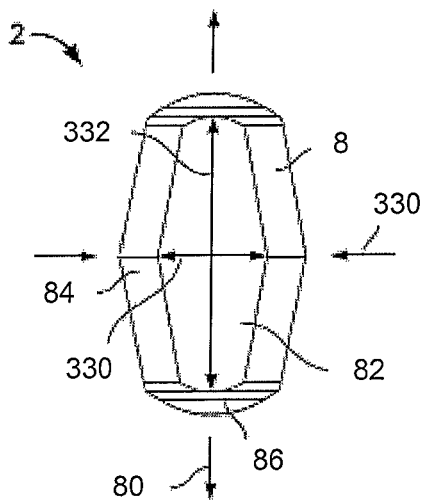

FIGS. 15 and 16 illustrate an expandable support device 2 that can have a first wedge 66 and a second wedge 68, such as the buttress of FIGS. 133 through 135, supra, of which any characteristic, feature, or functionality can be used for the expandable support device 2 described herein. A first wedge force 70 can be applied to the first wedge 66. A second wedge force 72 can be applied to the second wedge 68. The first wedge 66 can translate in the direction of arrow 74, as shown. The second wedge 68 can translate in the direction of arrow 76, as shown. FIG. 16 illustrates that the expandable support device 2 can have a larger, expanded diameter 78 after the first 70 and second wedge forces 72 have been applied.

FIGS. 17 through 20 illustrate a variation of a biocompatible implant that can be used for tissue repair, for example for repair bone fractures such as spinal compression fractures, and/or repairing soft tissue damage, such as herniated vertebral discs and/or an intervertebral/interspinous spacer or fusion device. The implant can be an expandable support device 2, for example a stent. The expandable support device 2 can have a longitudinal axis 80. The expandable support device 2 can have an elongated wall 8 around the longitudinal axis 80. The expandable support device 2 can have a substantially and/or completely hollow longitudinal port 82 along the longitudinal axis 80.

The wall 8 can have one or more first struts 84. The first struts 84 can be configured to be deformable and/or expandable. The wall 8 can have can have one or more second struts 86. The second struts 86 can be substantially undeformable and substantially inflexible. The first struts 84 can be flexibly (e.g., deformably rotatably) attached to the second struts 86.

The wall 8 can be configured to expand radially away from the longitudinal axis 80, for example in two opposite radial directions. A first set of first struts 84 can be aligned parallel to each other with respect to the longitudinal axis 80. A second set of first struts 80 can be aligned parallel to each other with respect to the longitudinal axis 80. The second set of first struts 84 can be on the opposite side of the longitudinal axis 80 from the first set of first struts 84. The second struts 86 can attach any or all sets of first struts 84 to other sets of first struts 84.

The second struts 86 can have one or more ingrowth ports 88. The ingrowth ports 88 can be configured to encourage biological tissue ingrowth therethrough during use in order to aid in fixing the expandable support device in place and/or promote fusion of adjacent bone structures, either within the same bone (e.g., for vertebroplasty or kyphoplasty) or between adjacent bone structures (e.g., between adjacent vertebral bodies to promote fusion). The ingrowth ports 88 can be configured to releasably and/or fixedly attach to a deployment tool or other tool. The ingrowth ports 88 can be configured to increase, and/or decrease, and/or focus pressure against the surrounding biological tissue during use. The ingrowth ports 88 can be configured to increase and/or decrease the stiffness of the second struts 86. The ingrowth ports 88 can be configured to receive and/or attach to a buttress.

The first struts 84 can be configured to have a "V" shape. The space between adjacent first struts 84 can be configured to receive and/or attach to a locking pin during use.

The wall 8 can have a wall thickness 20. The wall thickness 20 can be from about 0.25 mm (0.098 in.) to about 5 mm (0.2 in.), for example about 1 mm (0.04 in.). The wall 8 can have an inner diameter 90. The inner diameter 90 can be from about 1 mm (0.04 in.) to about 30 mm (1.2 in.), for example about 6 mm (0.2 in.). The wall thickness 20 and/or the inner diameter 90 can vary with respect to the length along the longitudinal axis 80. The wall thickness 20 and/or the inner diameter 90 can vary with respect to the angle formed with a plane parallel to the longitudinal axis 80. The expandable support device may have an expansion ratio (i.e., the ratio of the unexpanded diameter to the expanded diameter) of from about 1:2 to about 1:5 or greater, depending upon the application. For vertebroplasty and intervertebral spacing the expansion ratio is preferably about 1:3 to about 1:4.

Figure 21:
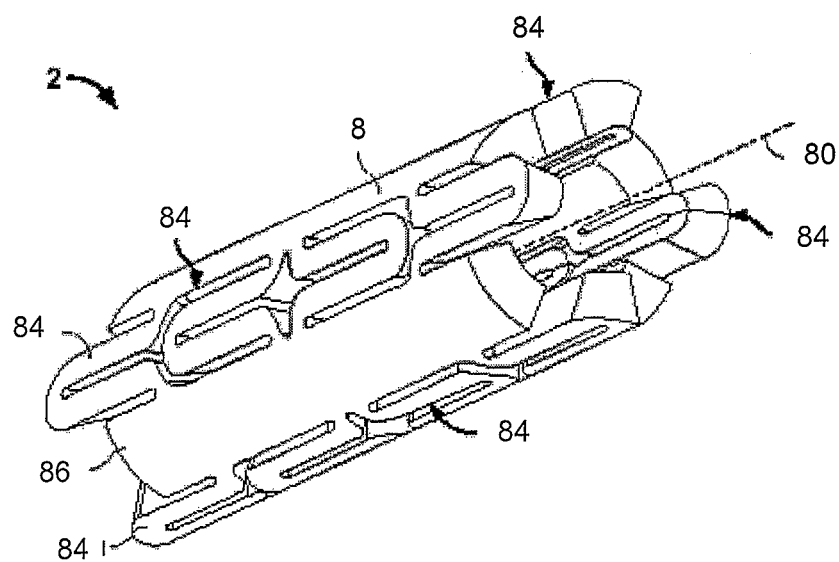
FIG. 21 is a perspective view of a variation of the expandable support device.
Figure 22:
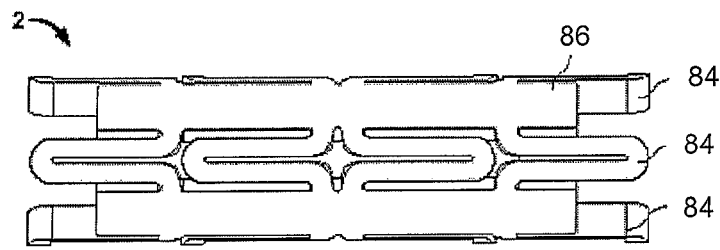
FIG. 22 is a side view of the variation of the expandable support device of FIG. 21.
Figure 23:
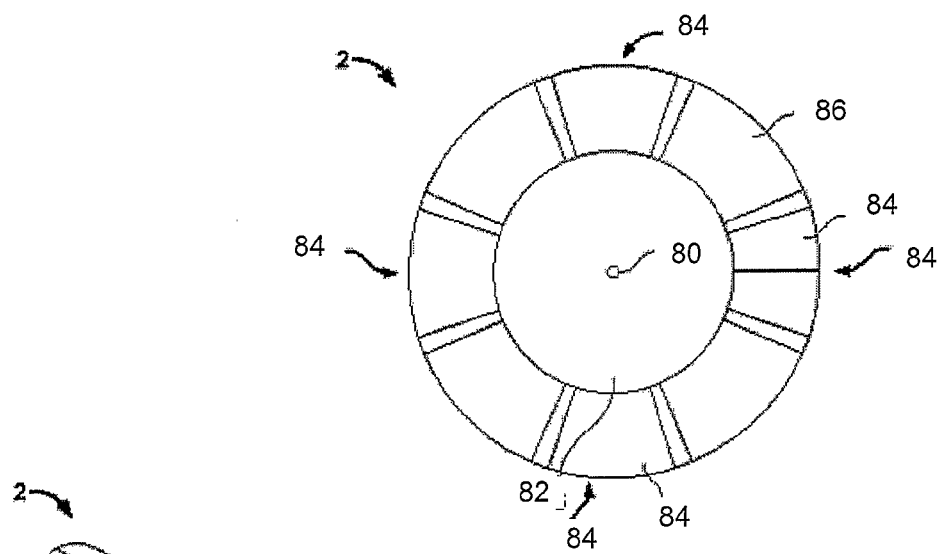
FIG. 23 is a front view of the variation of the expandable support device of FIG. 21.

FIGS. 21 through 23 illustrate another variation of an expandable support device 2 that can be configured to expand away from the longitudinal axis 80 in more than two opposite directions, for example in two sets of opposite radial directions. The wall 8 can have four sets of first struts 84. Each set of first struts 84 can be opposite to another set of first struts 84. Each of four sets of second struts 86 can attach each set of first struts 84. Providing four orthogonally oriented sets of first struts 10 permits expansion in two orthogonal planes, which advantageously may be considered height and width directions. In the case of an intervertebral implant, for example, such expansion in two directions permits height expansion to engage and support adjacent vertebral bodies and width expansion to increase the width of the surface contact area or "footprint" of engagement between the implant and the adjacent vertebrae. The implant may be filled with bone growth promoting substances (e.g., autologous bone, allograft bone, bone extenders, bone growth factors, bone morphogenic proteins, stem cells, carriers for any of them, and mixtures of any of them or with other suitable substances) to promote bone growth into and through the space.

The first struts 84 on a first longitudinal half of the expandable support device 2 can be oriented (e.g., the direction of the pointed end of the "V" shape) in the opposite direction as the first struts 84 on a second longitudinal half of the expandable support device 2. See FIGS. 21-22. Orienting the first struts 84 in opposite directions permits controlled expansion of the expandable support device 2 such that the overall length of the expandable support device 2 can be conserved during and after expansion, with minimal longitudinal displacement of radially opposed sides of the expandable support device 2.

Figure 24:
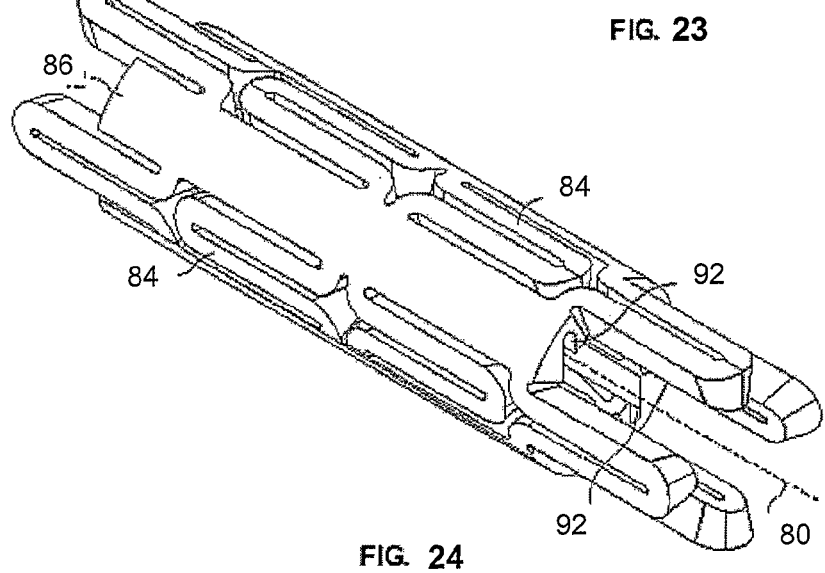
FIG. 24 is a perspective view of a variation of the expandable support device.
Figure 25:
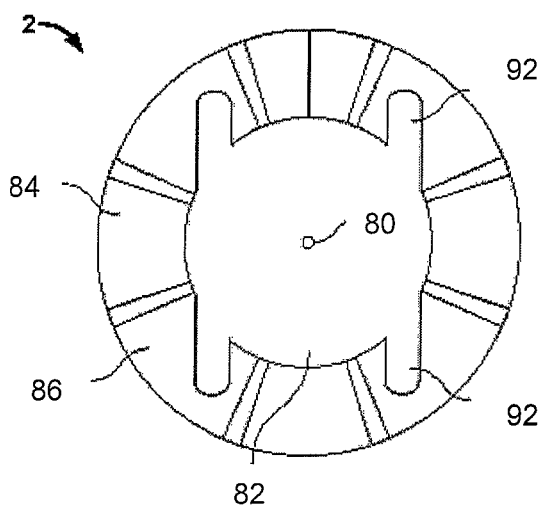
FIG. 25 is a front view of the variation of the expandable support device of FIG. 24.

FIGS. 24 and 25 illustrate that the longitudinal port 82 can have one or more lock grooves 92. The lock grooves 92 can be configured to receive and/or slidably and fixedly or releasably attach to a locking pin or buttress. As explained in greater detail below, the locking pin or buttress may be an insertable structure separate from the expandable support device 2 or may be preassembled to the expandable support device 2 or may be integrally formed with the expandable support device 2.

Figure 26:
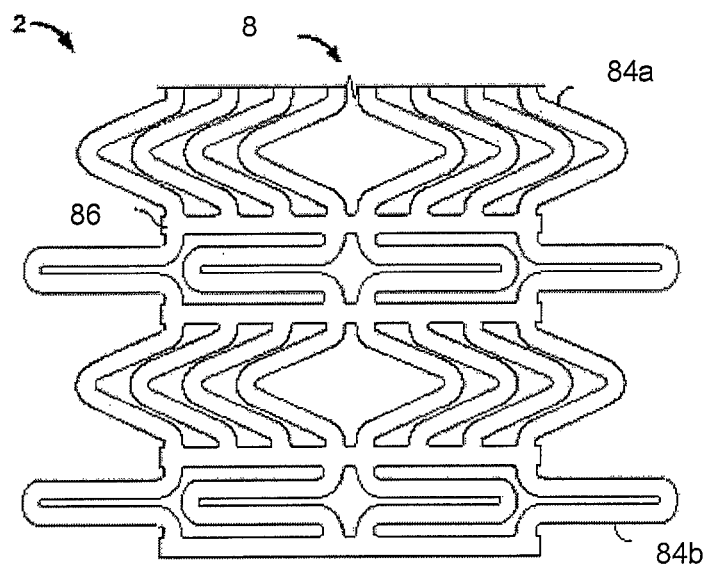
FIG. 26 illustrates a flattened pattern for a variation of the expandable support device.

FIG. 26 illustrates a visually flattened pattern of the wall 8 for another variation of the expandable support device 2. (The pattern of the wall 8 can be flattened for illustrative purposes only, or the wall 8 can be cut in a flattened state and welded or otherwise secured into a three dimensional shape during the manufacturing process.) The pattern can have multiple configurations for the first and/or second struts 84 and/or 86. For example, first struts 84 can have a first configuration 84*a* (e.g., a "V" shape in oppositely oriented sets) and first struts 84 can have a second configuration 84*b* (e.g., a "U" shape in oppositely oriented sets. In FIG. 26, second struts 12 are relatively narrow between the sets of first struts).

Figure 27:
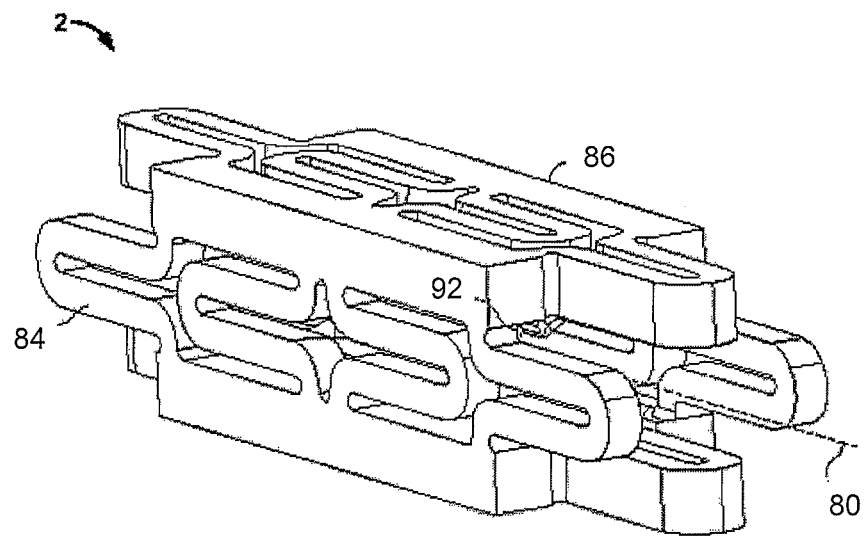
FIG. 27 is a perspective view of a variation of the expandable support device.
Figure 28:
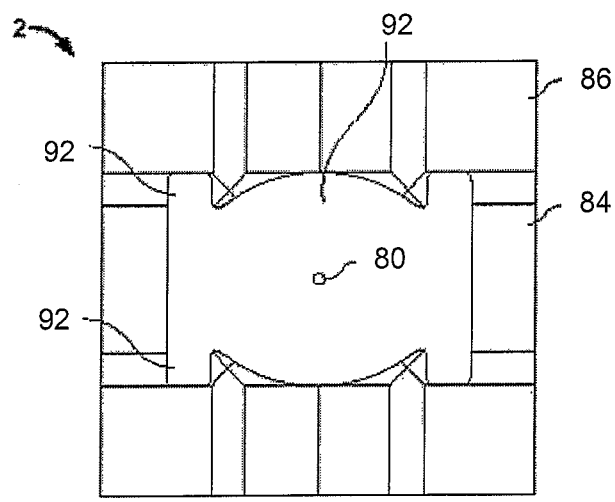
FIG. 28 is a front view of the variation of the expandable support device of FIG. 27.

FIGS. 27 and 28 illustrate that that rather than the generally circular or oval cross sectional shape of prior variations, the expandable support device 2 can have a square or, rectangular cross-sectional configuration. As shown, the square or rectangular configuration can include features such as grooves 20 to receive one or more locking pins or buttresses, as contemplated herein.

Figure 29:
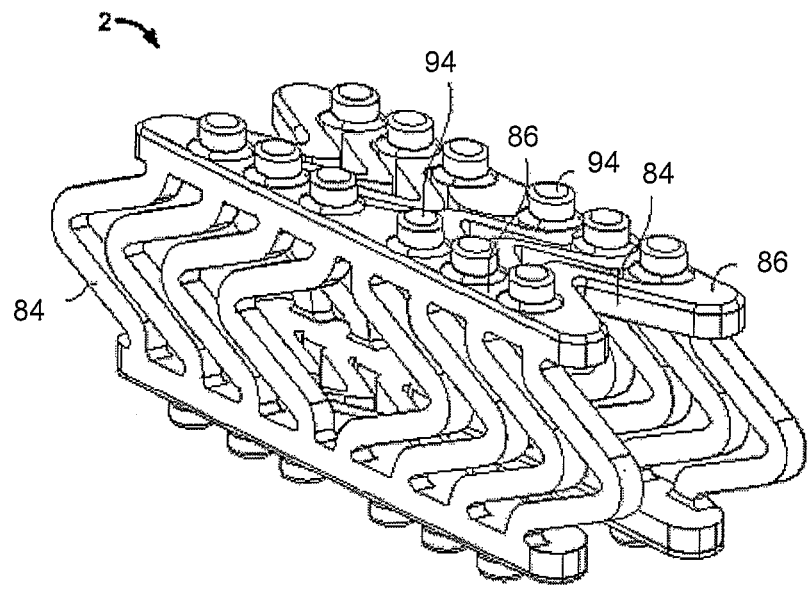
FIG. 29 is a perspective view of a variation of the expandable support device.
Figure 30:
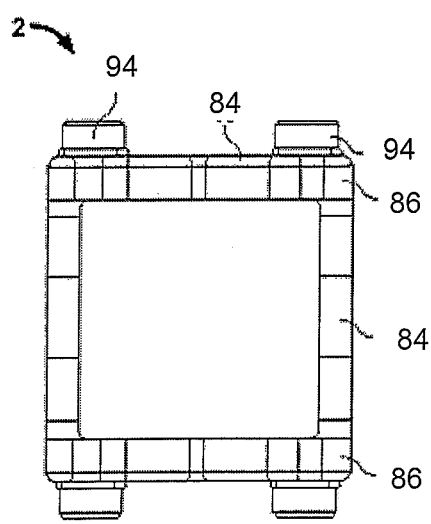
FIG. 30 is a front view of the variation of the expandable support device of FIG. 29.
Figure 31:
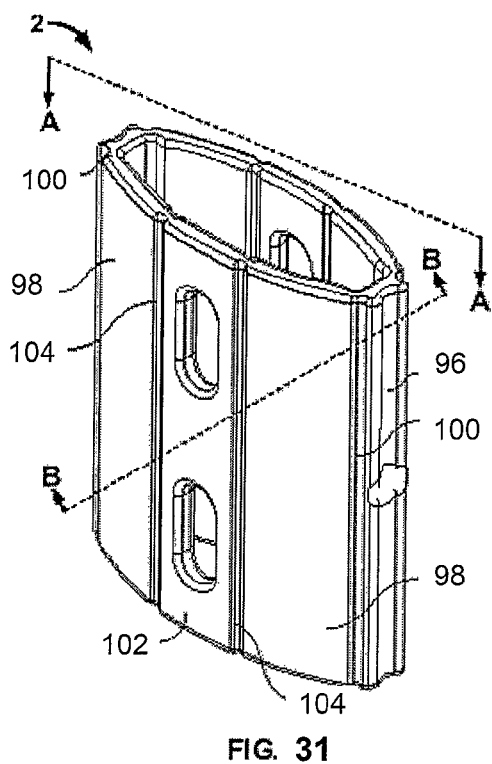
FIG. 31 is a perspective view of a variation of the expandable support device.
Figure 32:
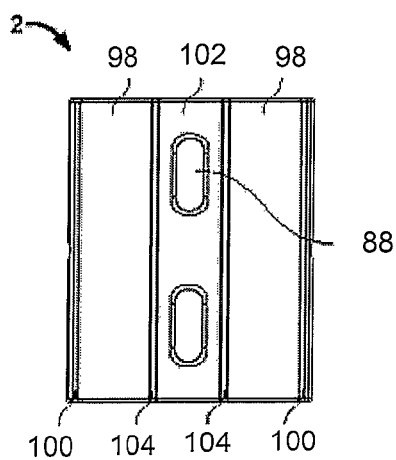
FIG. 32 is top view of the variation of the expandable support device of FIG. 31.
Figure 33:
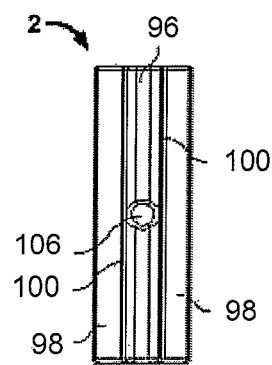
FIG. 33 is a side view of the variation of the expandable support device of FIG. 31.
Figure 34:
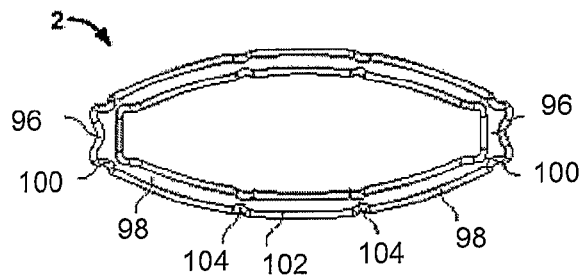
FIG. 34 is a front view of the variation of the expandable support device of FIG. 31.

FIGS. 29 and 30 illustrate that the expandable support device 2 can have protruding tissue engagement elements, such as tissue hooks, and/or barbs, and/or cleats 94 (referred to herein as cleats 94). The cleats 94 can be integral with and/or fixedly or removably attached to the first and/or second struts 86. The cleats 94 can be on substantially opposite sides of the expandable support device 2. As will be appreciated, as the expandable support device 2 can be expanded the tissue engagement elements will engage adjacent tissue, e.g., adjacent vertebral bodies in the case of an intervertebral spacer, to help secure the device in place relative to adjacent structures.

FIGS. 31 through 34 illustrate that the expandable support device 2 can have panels attached to other panels at flexible joints. The expandable support device 2 can have first panels 96 attached to and/or integral with second panels 98 at first joints 100. The second panels 98 can be attached to and/or integral with third panels 102 at second joints 104. The expandable support device 2 can have one or more tool engagement ports 106, for example on the first panels 96. The expandable support device 2 can have one or more ingrowth ports 88, for example, on the third panels 102. The outside of the first panel 96 can be concave.

Figure 35:
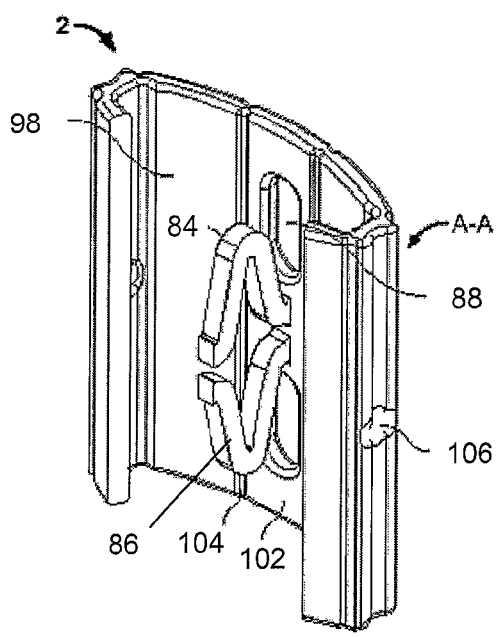
FIG. 35 illustrates a variation of section A-A of the variation of the expandable support device of FIG. 31.
Figure 36:
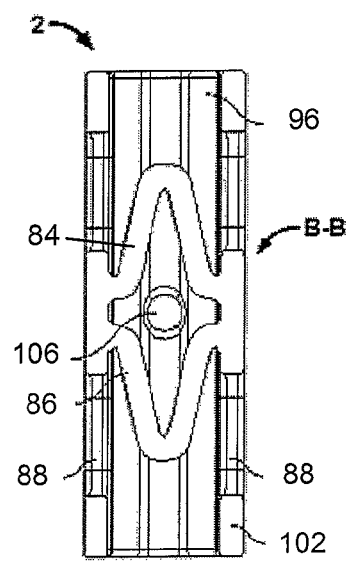
FIG. 36 illustrates a variation of section B-B of the variation of the expandable support device of FIG. 31.
Figure 37:
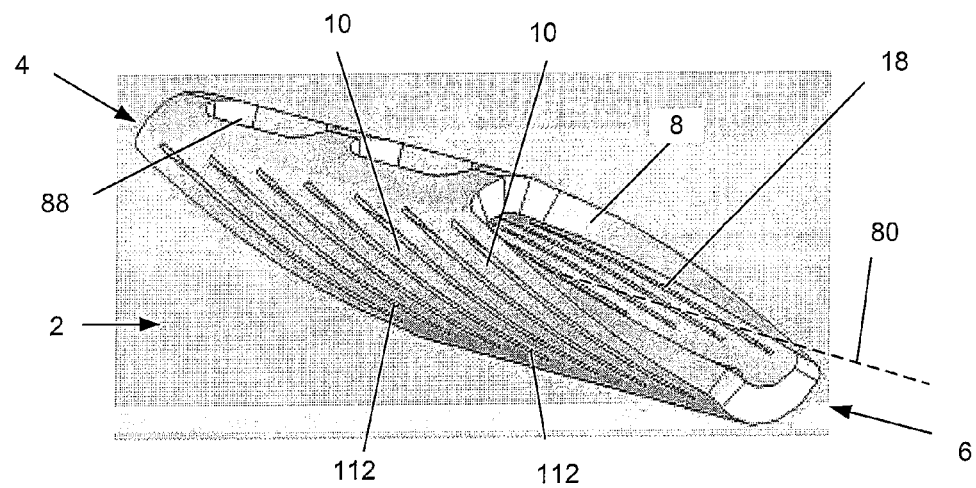
FIG. 37 is a side perspective view of a variation of the expandable support device.
Figure 38:
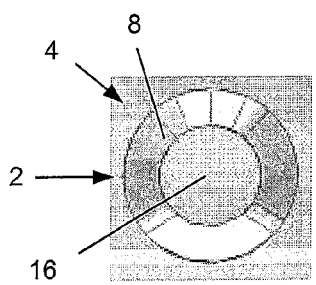
FIG. 38 is a front view of the variation of the expandable support device of FIG. 37.
Figure 39:
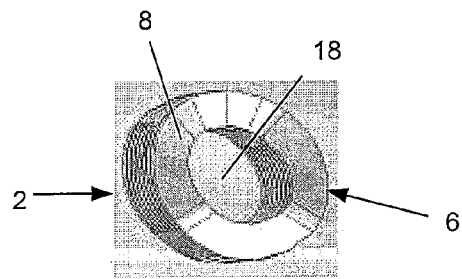
FIG. 39 is a rear perspective view of the variation of the expandable support device of FIG. 37.
Figure 40:
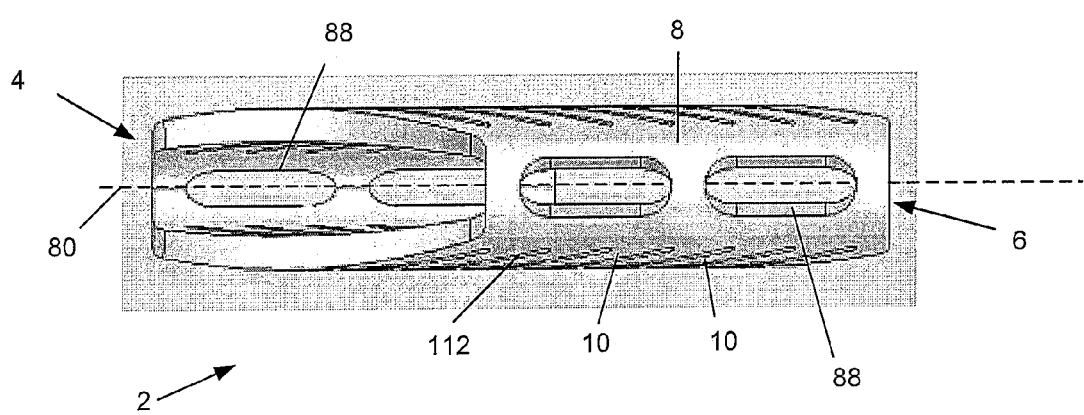
FIG. 40 is a bottom view of the variation of the expandable support device of FIG. 37.
Figure 41:
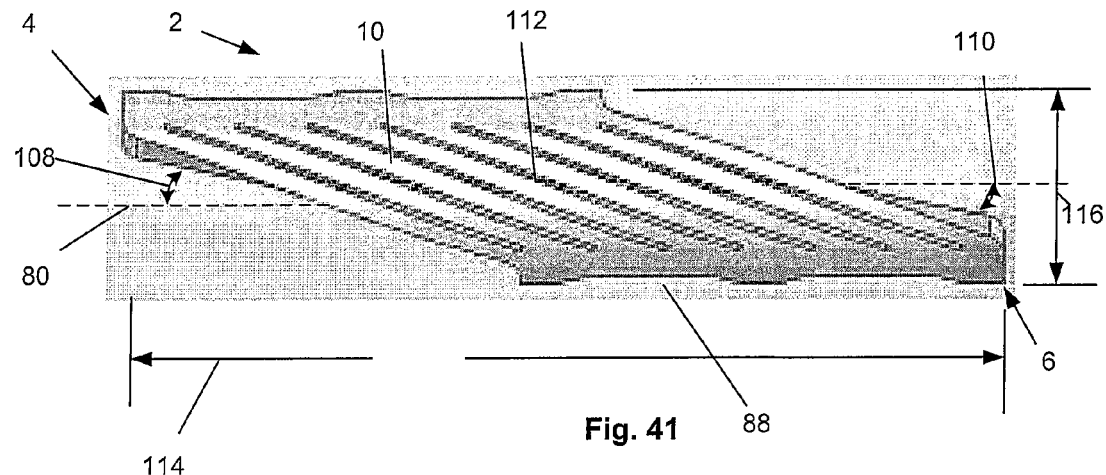
FIG. 41 is a side view of the variation of the expandable support device of FIG. 37.

FIGS. 35 and 36 illustrate that the expandable support device 2 can have first and/or second struts 84, 86 and/or and panels 96, 98. The first and/or second struts 84, 86 can be internal to the panels 96, 98. The first struts 84 can be attached to the third panels 102.

The expandable support device 2 can have a radius of curvature along the longitudinal axis 80. The radius of curvature can be from about 1 mm (0.04 in.) to about 250 mm (10 in.), for example about 50 mm (2 in.). (The wall 8 is shown sans panels or struts for illustrative purposes.) The expandable support device 2 can have at least one flat side, for example two flat sides. The two flat sides can be on opposite sides of the expandable support device 2 from each other. In the variation shown in FIGS. 35-36, the internal first strut 84 can help provide controlled expansion of the device and internal support to the expanded device.

FIGS. 37 through 41 illustrate an expandable support device 2, that can be implanted in a bone, such as a compression fracture in a vertebra, or in soft tissue, such as a herniated intervertebral disc, or interspinous ligament. The expandable support device 2 should be biocompatible. The expandable support device 2 can be used for tissue repair, for example for repair bone fractures such as spinal compression fractures, and/or repairing soft tissue damage, such as herniated vertebral discs of fusion or fixation.

The expandable support device 2 can have a longitudinal axis 80. The expandable support device 2 can have a first end 4 and a second end 6. The first end 4 can be substantially parallel with the second end 6. The first end 4 may be displaced from the longitudinal axis 80 by a first angle 108 and the second end may be displaced from the longitudinal axis 80 by a second angle 110 when the expandable support device 2 is in a contracted configuration (as shown). The expandable support device 2 can be hollow, for example along the longitudinal axis 80. The first end 4 can have a first port 16. The second end 6 can have a second port 18. The first angle 108 can be substantially equal to the second angle 110. The angles 108, 110 can be from about 0° to about 90°, more narrowly from about 5° to about 45°, yet more narrowly from about 10° to about 30°, for example about 20 °.

The expandable support device 2 can have a wall 8. The outer and/or inner surfaces of the wall 8 can be configured to increase friction or be capable of an interference fit with another object, such as a second expandable support device 46. The configurations to increase friction or be capable of an interference fit include teeth, knurling, coating, or combinations thereof.

The wall 8 can have struts 10. By way of example only, the wall 8 can have about 8 struts 10 on each side of the expandable support device 2. The struts 10 can be substantially parallel to the slanted configuration of the angled first end 4 and/or second end 6. The struts 10 can be separated from the other struts 10 by wall openings 112. The expandable support device 2 can have about 7 wall openings 112 on each side. The wall openings 112 can be substantially parallel to the first end 4 and/or second end 6, for example when the expandable support device 2 is in a contracted configuration. The expandable support device 2 can have ingrowth ports 88.

The expandable support device 2 can have a first port 16 and/or a second port 18. A hollow of the expandable support device 2 can be completely or partially coated and/or filled with agents and/or a matrix as listed below.

The leading end of the expandable support device 2 can be sharpened. The leading end can be used to help move tissue aside during implantation and deployment. The leading end can be self-penetrating.

When in a contracted configuration, the expandable support device 2 can have a contracted length 114 (i.e., the length when the expandable support device is in a radially contracted configuration) and a contracted height 116. By way of example only, the contracted length 114 can be from about 0.318 cm (0.125 in.) to about 10 cm (4 in.), for example about 3.8 cm (1.5 in). The contracted height 116 can be from about 0.1 cm (0.05 in.) to about 3 cm (1 in.), for example about 0.8 cm (0.3 in.).

Figure 42:
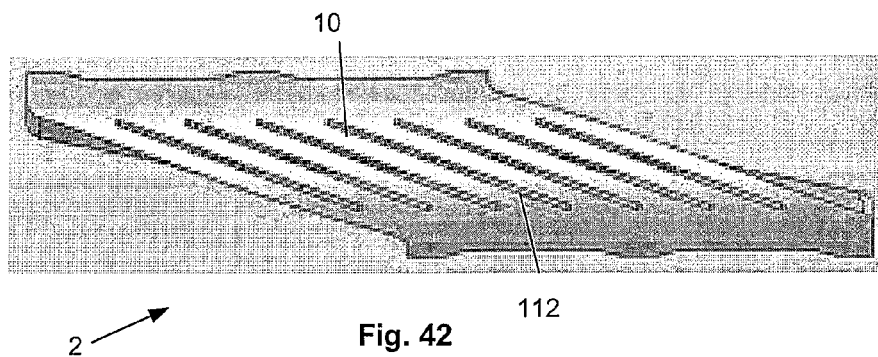
FIGS. 42 and 43 are side views of various variations of the expandable support device.

FIG. 42 illustrates that the expandable support device 2 can have shorter struts 10 than the struts shown in FIGS. 37 through 41. By the way of example only, the length of the struts 10 can be from about 0.3 cm (0.1 in.) to about 5 cm (2 in.), for example about 2 cm (0.7 in.), also for example about 1 cm (0.5 in.).

Figure 43:
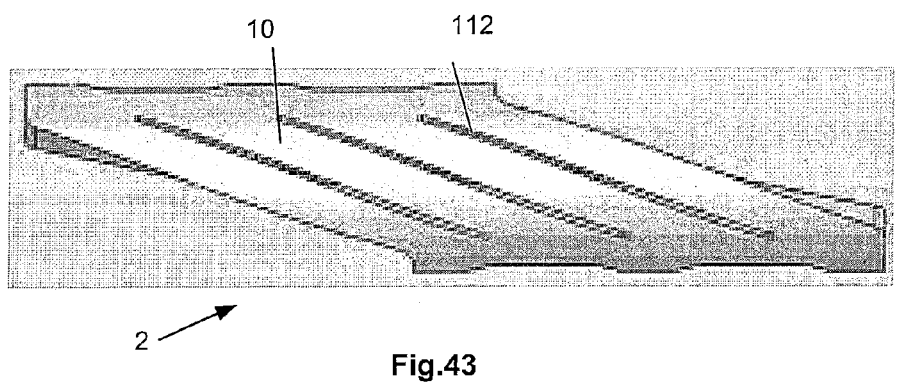

FIG. 43 illustrates that the expandable support device 2 can have from relatively few struts 10. It is contemplated that the expandable support device 2 may have from about 2 struts to about 50 struts 10. About 4 struts 10 to about 8 struts 10 may be suitable for many applications. The expandable support device 2 can have from about 1 wall opening 112 to about 51 wall openings 112, for example about 3 wall openings 112, also for example about 7 wall openings 112.

Figure 44:
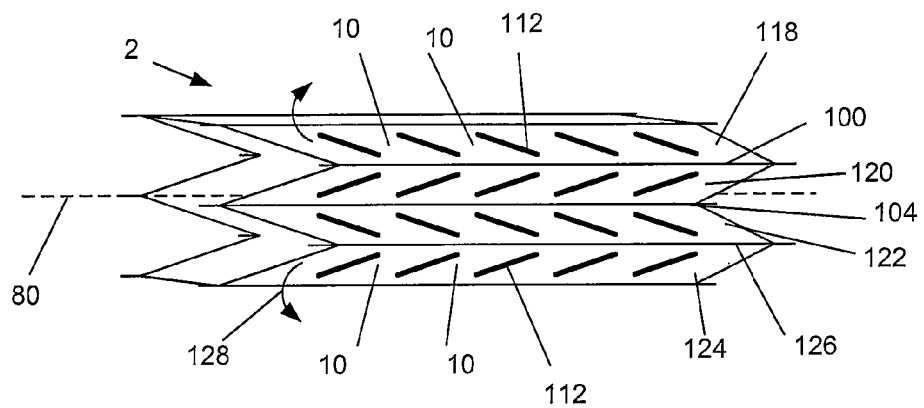
FIG. 44 is a side perspective view of a variation of the expandable support device.

FIG. 44 illustrates that the expandable support device 2 can have a first pane 118, a second pane 120, a third pane 122, and a fourth pane 124. A first joint 100 can attach the first pane 118 to the second pane 120. A second joint 104 can attach the second pane 120 to the third pane 122. A third joint 126 can attach the third pane 122 to the fourth pane 124. The joints can rotatably attach the panes. The joints can be separate from or integral with the panes. Each pane can have struts 10 and wall openings 112. During use, the joints can enable the panes to rotate in-plane, as shown by arrows 128.

Figure 45:
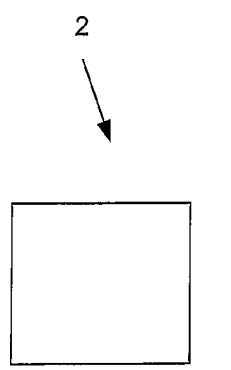
FIGS. 45 through 47 are front views of various variations of the expandable support devices.
Figure 46:
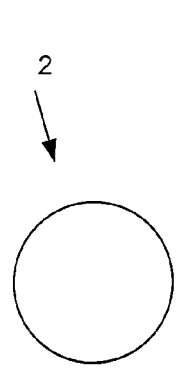
Figure 47:
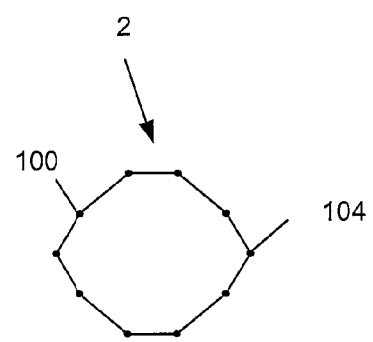

FIGS. 45, 46 and 47 illustrate that the expandable support device 2, can have for example a square or rectangular, circular, or polygonal cross-section, respectively. FIG. 47 shows the joints as contemplated above in the description of FIG. 44 as nodes having a wider section than the wall 8, but the joints can also have the same width or a smaller width than the wall 8.

FIGS. 48 through 50 illustrate that the expandable support device 2 can have a radius of curvature 130 along the longitudinal axis 80. The radius of curvature 130 can be from about 1 mm (0.04 in.) to about 250 mm (10 in.), for example about 50 mm (2 in.). The wall 8 is shown without panels or struts 10 for illustrative purposes, but it will be understood that the initial configuration and deployment force and method can influence the shape of the deployed implant. The expandable support device 2 can have at least one flat side, for example two flat sides. The two flat sides can be on opposite sides of the expandable support device 2 from each other.

The expandable support devices 2 can have textured and/or porous surfaces for example, to increase friction against bone surfaces, and/or promote tissue ingrowth. The expandable support devices 2 can be coated with a bone growth factor, such as a calcium base.

The expandable support device 2 can be covered by a thin metal screen. The thin metal screen can expand and/or open when the expandable support device 2 expands.

Any or all elements of the expandable support device 2 and/or other devices or apparatuses described herein can be made from, for example, a single or multiple stainless steel alloys, nickel titanium alloys (e.g., Nitinol), cobalt-chrome alloys (e.g., ELGILOY® from Elgin Specialty Metals, Elgin, Ill.; CONICHROME® from Carpenter Metals Corp., Wyomissing, Pa.), nickel-cobalt alloys (e.g., MP35N® from Magellan Industrial Trading Company, Inc., Westport, Conn.), molybdenum alloys (e.g., molybdenum TZM alloy, for example as disclosed in International Pub. No. WO 03/082363 A2, published 9 Oct. 2003, which is herein incorporated by reference in its entirety), tungsten-rhenium alloys, for example, as disclosed in International Pub. No. WO 03/082363, polymers such as polyethylene teraphathalate (PET)/polyester (e.g., DACRON® from E. I. Du Pont de Nemours and Company, Wilmington, Del.), polypropylene, (PET), polytetrafluoroethylene (PTFE), expanded PTFE (ePTFE), polyether ketone (PEK), polyether ether ketone (PEEK), poly ether ketone ketone (PEKK) (also poly aryl ether ketone ketone), nylon, polyether-block co-polyamide polymers (e.g., PEBAX® from ATOFINA, Paris, France), aliphatic polyether polyurethanes (e.g., TECOFLEX® from Thermedics Polymer Products, Wilmington, Mass.), polyvinyl chloride (PVC), polyurethane, thermoplastic, fluorinated ethylene propylene (FEP), absorbable or resorbable polymers such as polyglycolic acid (PGA), polylactic acid (PLA), polycaprolactone (PCL), polyethyl acrylate (PEA), polydioxanone (PDS), and pseudo-polyamino tyrosine-based acids, extruded collagen, silicone, zinc, echogenic, radioactive, radiopaque materials, a biomaterial (e.g., cadaver tissue, collagen, allograft, autograft, xenograft, bone cement, morselized bone, osteogenic powder, beads of bone) any of the other materials listed herein or combinations thereof. Examples of radiopaque materials are barium sulfate, zinc oxide, titanium, stainless steel, nickel-titanium alloys, tantalum and gold.

Any or all elements of the expandable support device 2 and/or other devices or apparatuses described herein, can be, have, and/or be completely or partially coated with agents and/or a matrix a matrix for cell ingrowth or used with a fabric, for example a covering (not shown) that acts as a matrix for cell ingrowth. The matrix and/or fabric can be, for example, polyester (e.g., DACRON® from E. I. Du Pont de Nemours and Company, Wilmington, Del.), polypropylene, PTFE, ePTFE, nylon, extruded collagen, silicone or combinations thereof.

The expandable support device 2 and/or elements of the expandable support device 2 and/or other devices or apparatuses described herein and/or the fabric can be filled, coated, layered and/or otherwise made with and/or from cements, fillers, glues, and/or an agent delivery matrix known to one having ordinary skill in the art and/or a therapeutic and/or diagnostic agent. Any of these cements and/or fillers and/or glues can be osteogenic and osteoinductive growth factors.

Examples of such cements and/or fillers includes bone chips, demineralized bone matrix (DBM), calcium sulfate, coralline hydroxyapatite, biocoral, tricalcium phosphate, calcium phosphate, polymethyl methacrylate (PMMA), biodegradable ceramics, bioactive glasses, hyaluronic acid, lactoferrin, bone morphogenic proteins (BMPs) such as recombinant human bone morphogenetic proteins (rhBMPs), other materials described herein, or combinations thereof.

The agents within these matrices can include any agent disclosed herein or combinations thereof, including radioactive materials; radiopaque materials; cytogenic agents; cytotoxic agents; cytostatic agents; thrombogenic agents, for example polyurethane, cellulose acetate polymer mixed with bismuth trioxide, and ethylene vinyl alcohol; lubricious, hydrophilic materials; phosphor cholene; anti-inflammatory agents, for example non-steroidal anti-inflammatories (NSAIDs) such as cyclooxygenase-1 (COX-1) inhibitors (e.g., acetylsalicylic acid, for example ASPIRIN® from Bayer A G, Leverkusen, Germany; ibuprofen, for example ADVIL® from Wyeth, Collegeville, Pa.; indomethacin; mefenamic acid), COX-2 inhibitors (e.g., VIOXX® from Merck & Co., Inc., Whitehouse Station, N.J.; CELEBREX® from Pharmacia Corp., Peapack, N.J.; COX-1 inhibitors); immunosuppressive agents, for example Sirolimus (RAPAMUNE®, from Wyeth, Collegeville, Pa.), or matrix metalloproteinase (MMP) inhibitors (e.g., tetracycline and tetracycline derivatives) that act early within the pathways of an inflammatory response. Examples of other agents are provided in Walton et al, Inhibition of Prostoglandin $E_2$ Synthesis in Abdominal Aortic Aneurysms, *Circulation*, Jul. 6, 1999, 48-54; Tambiah et al, Provocation of Experimental Aortic Inflammation Mediators and Chlamydia Pneumoniae, *Brit. J. Surgery* 88 (7), 935-940; Franklin et al, Uptake of Tetracycline by Aortic Aneurysm Wall and Its Effect on Inflammation and Proteolysis, *Brit. J. Surgery* 86 (6), 771-775; Xu et al, Sp1 Increases Expression of Cyclooxygenase-2 in Hypoxic Vascular Endothelium, *J. Biological Chemistry* 275 (32) 24583-24589; and Pyo et al, Targeted Gene Disruption of Matrix Metalloproteinase-9 (Gelatinase B) Suppresses Development of Experimental Abdominal Aortic Aneurysms, *J. Clinical Investigation* 105 (11), 1641-1649 which are all incorporated by reference in their entireties.

The expandable support devices 2 can be laser cut, machined, cut by wire electrical discharge machining ("EDM") or made by other suitable techniques. The expandable support device 2 can be cut in a fully contracted or unexpanded configuration or may be cut in a partially opened pattern, then loaded (e.g., crimped) onto a deployment tool 132 (e.g., balloon 134). The loaded expandable support device 2 can have a smaller profile while plastically deforming the struts 10 past their limits.

The expandable support device 2 can be longitudinally segmented. Multiple expandable support devices 2 can be attached first end 4 to second end 6, and/or a single expandable support device 2 can be severed longitudinally into multiple expandable support devices 2.

Method of Use

Figure 51:
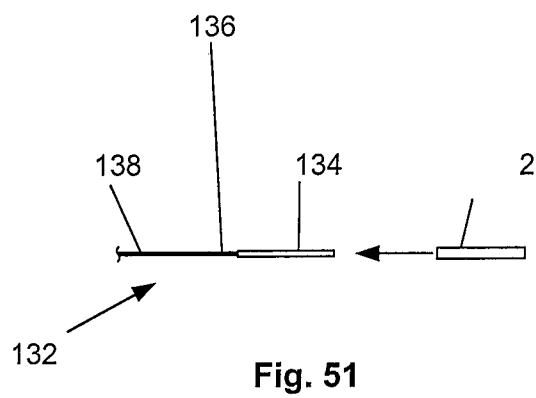
FIGS. 51 and 52 illustrate a variation of a method for using a delivery system for the expandable support element.

FIG. 51 illustrates that the expandable support device 2 can be loaded in a collapsed (i.e., contracted) configuration onto a deployment tool 132. The deployment tool 132 can have an expandable balloon 134 catheter 136 as known to those having an ordinary level of skill in the art. The catheter 136 can have a fluid conduit 138. The fluid conduit 138 can be in fluid communication with balloon 134. The balloon 134 and the deployment tool 132 can be the balloon 134 and deployment tool 132 described in PCT Application No. US2005/033,965, Publication No. WO 2006/034,396, filed 21 Sep. 2005 entitled "Balloon and Methods of Making and Using." The balloon 134 can be configured to receive a fluid pressure of at least about 5,000 kPa (50 atm), more narrowly at least about 10,000 kPa (100 atm), for example at least about 14,000 kPa (140 atm).

Alternatively, the deployment tool 132 can be a pair of wedges, an expandable jack, other expansion tools, or combinations thereof.

Figure 52:
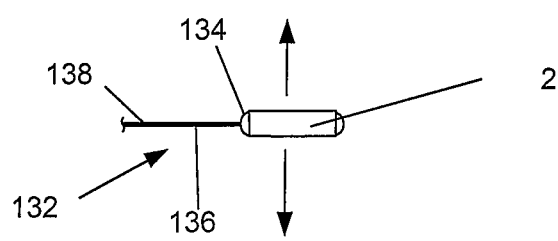

FIG. 52 illustrates that the fluid pressure in the fluid conduit 138 and balloon 134 can increase, thereby inflating the balloon 134, as shown by arrows. The expandable support device 2 can expand, for example, due to pressure from the balloon 134.

Figure 53:
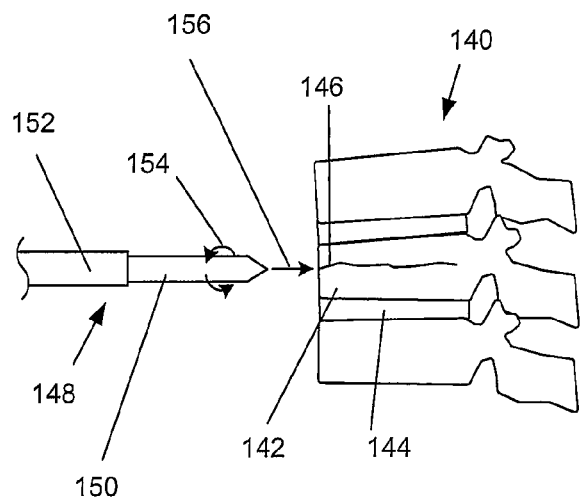
FIGS. 53 through 55 illustrate a variation of a method for accessing a damage site in the vertebra.
Figure 54:
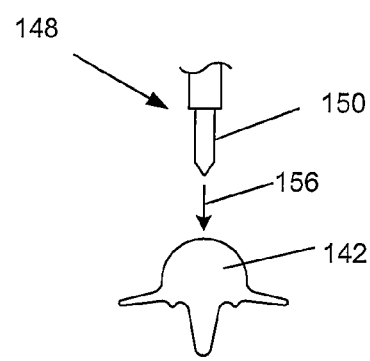

FIGS. 53 (side view) and 54 (top view) illustrate a vertebral column 140 that can have one or more vertebra 142 separated from the other vertebra 142 by discs 144. The vertebra 142 can have a damage site 146, for example a compression fracture.

An access tool 148 can be used to gain access to the damage site 146 and or increase the size of the damage site 146 to allow deployment of the expandable support device 2. The access tool 148 can be a rotating or vibrating drill 150 that can have a handle 152. Optionally, the drill 150 may oscillate, as shown by arrows 154. The drill 150 can then be translated, as shown by arrow 156, toward and into the vertebra 142 so as to pass into the damage site 146.

Figure 55:
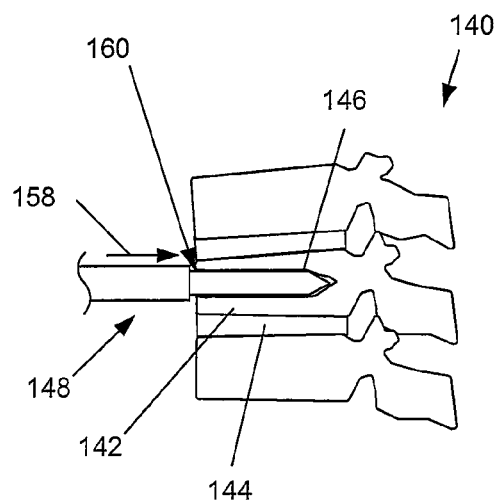

FIG. 55 illustrates that the access tool 148 can be translated, as shown by arrow 158, to remove tissue at the damage site 146. The access tool 148 can create an access port 160 at the surface of the vertebra 142. The access port 160 can open to the damage site 146. The access tool 148 can then be removed from the vertebra 142.

Figure 56:
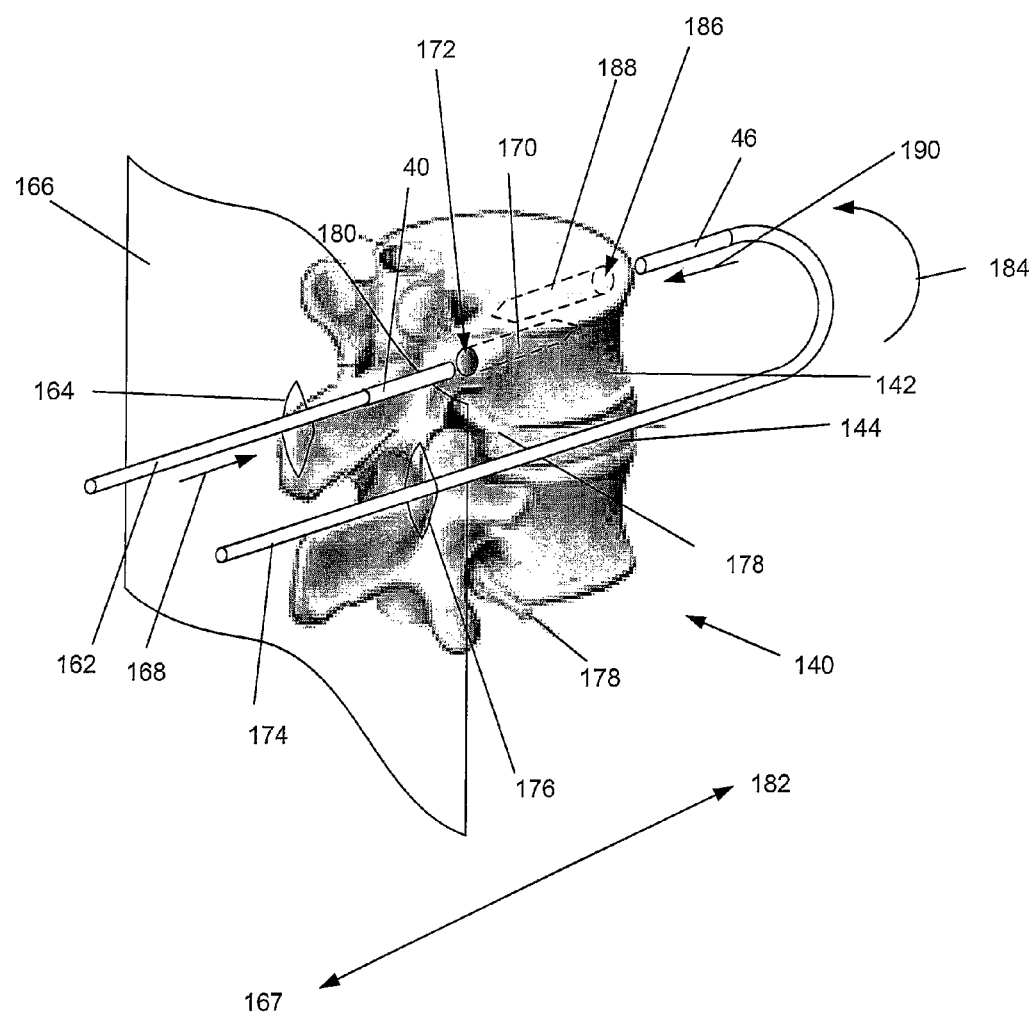
FIG. 56 illustrates two methods for delivering expandable support devices to the vertebral column.

FIG. 56 illustrates that a first deployment tool 162 can enter posteriorly through the subject's back. The first deployment tool 162 can enter through a first incision 164 in the skin 166 on the posterior side 167 of the subject near the vertebral column 140. The first deployment tool 162 can be translated, as shown by arrow 168, to position a first expandable support device 40 into a first damage site 170. The first access port 172 can be on the posterior side 167 of the vertebra 142.

A second deployment tool 174 can enter through a second incision 176 (as shown) in the skin 166. The second incision 176 may be posterior (as shown) or may be anterior, lateral, posterior lateral, or the like. The second deployment tool 174 can be translated through muscle (not shown), around nerves 178, the spinal cord 180, and anterior 182 of the vertebral column 140. The second deployment tool 174 can be steerable. The second deployment tool 174 can be steered, as shown by arrow 184, to align the distal tip of the second expandable support device 46 with a second access port 186 on a second damage site 188. The second access port 186 can face anteriorly 182. The second deployment tool 174 can translate, as shown by arrow 190, to position the second expandable support device 46 in the second damage site 188.

As illustrated, the vertebra 142 can have multiple damage sites and expandable support devices deployed therein. The expandable support devices can be deployed from the anterior 182, posterior 167, both lateral, superior, inferior, any angle, or combinations of the directions thereof. Of course, a single device may be deployed from one direction rather than multiple devices from multiple directions.

Figure 57:
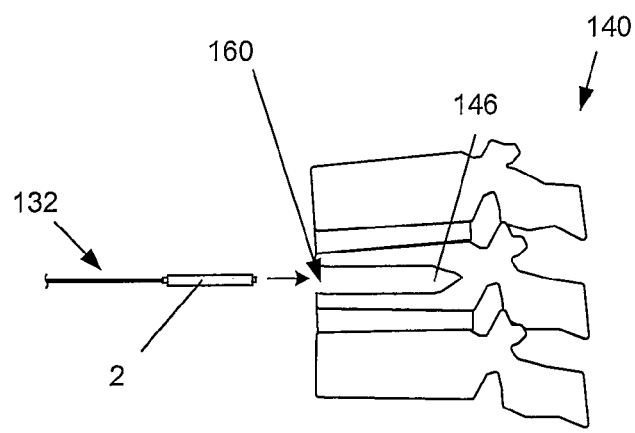
FIGS. 57 through 62 illustrate various methods for deploying the expandable support device into the damage site in the vertebra.
Figure 58:
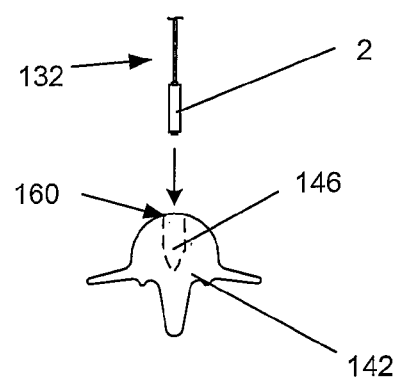
Figure 59:
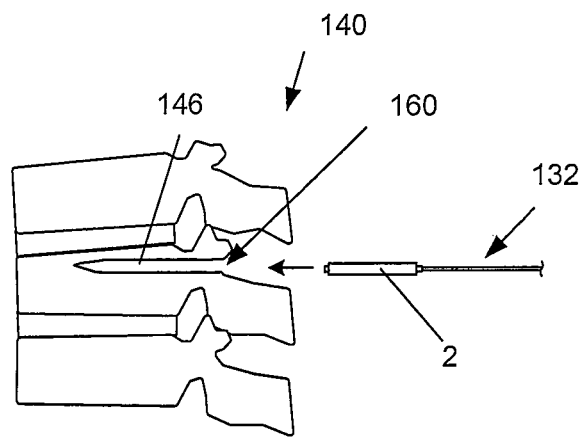
Figure 60:
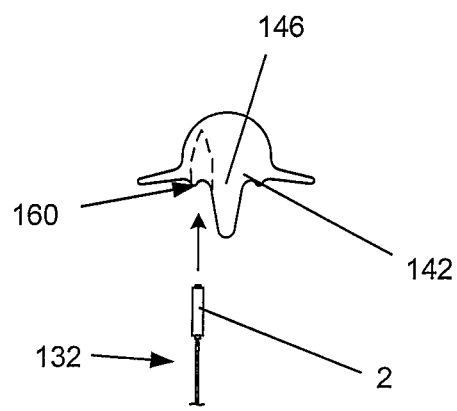

FIGS. 57 and 58 illustrate translating, as shown by arrow, the deployment tool 132 loaded with the expandable support device 2 through the access port 160 from the anterior side 182 of the vertebral column 140. FIGS. 59 and 60 illustrate that the deployment tool 132 can be deployed from the posterior side 167 of the vertebral column 140. The deployment tool 132 can be deployed off-center, for example, when approaching the posterior side 167 of the vertebral column 140.

Figure 61:
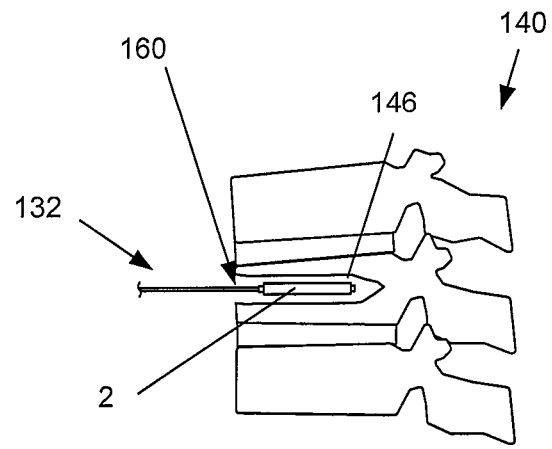

FIG. 61 illustrates that deployment tool 132 can position the expandable support device 2 in the vertebra 142 and into the damage site 146.

Figure 62:
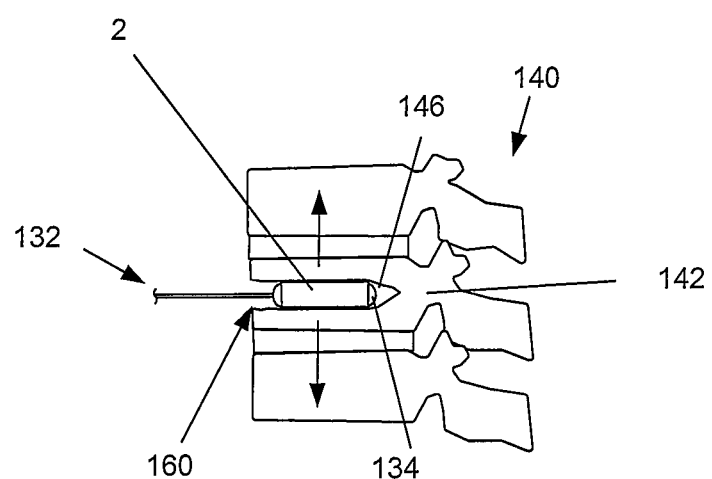

FIG. 62 illustrates that the fluid pressure in the fluid conduit 136 and the balloon 134 can increase, thereby inflating the balloon 134, as shown by arrows. The expandable support device 2 can expand, for example, due to pressure from the balloon 134. The balloon 134 can be expanded until the expandable support device 2 is substantially fixed to the vertebra 142. The balloon 134 and/or the expandable support device 2 can reshape the vertebral column 140 to a more natural configuration during expansion of the device.

FIGS. 63 and 64 illustrate that first and second deployment tools 162 and 174 can position and deploy first and second expandable support devices 40 and 46 simultaneously, and/or in the same vertebra 142 and into the same or different damage sites 170 and 188.

FIG. 65 illustrates that the fluid pressure in the fluid conduit 138 and the balloon 134 can increase, thereby inflating the balloon 134, as shown by arrows. The expandable support device 2 can expand, for example, due to pressure from the balloon 134. The balloon 134 can be expanded until the expandable support device 2 is substantially fixed to the vertebra 142. The balloon 134 and/or the expandable support device 2 can reshape the vertebral column 140 to a more natural configuration during expansion of the balloon 134.

Figure 66:
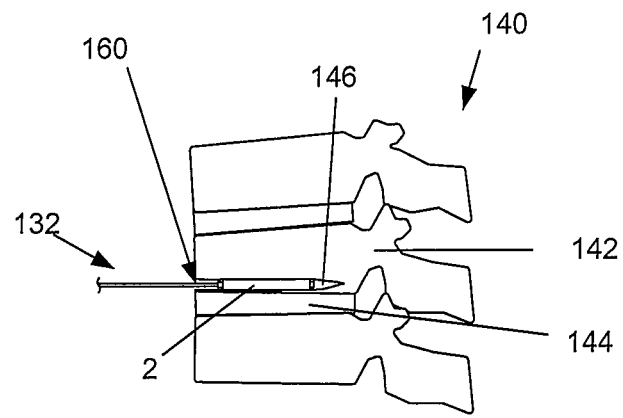
FIG. 66 illustrates a variation of a method for deploying the expandable support device into the damage site in the vertebra.

FIG. 66 illustrates that the access port 160 can be made close to the disc 144, for example when the damage site 146 is close to the disc 144. The deployment tool 132 can be inserted through the access port 160 and the expandable support device 2 can be deployed as described supra.

Figure 67:
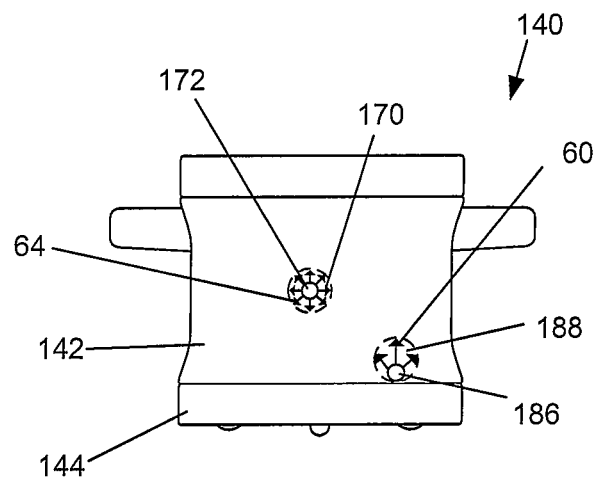
FIG. 67 illustrates variations of methods for deploying the expandable support device into the damage site in the vertebra.

FIG. 67, a front view of the vertebral column 140, illustrates that more than one expandable support device 2 can be deployed into a single vertebra 142. For example, a first expandable support device (not shown) can be inserted through a first access port 172 and deployed in a first damage site 170, and a second expandable support device (not shown) can be inserted through a first access port 172 and deployed in a second damage site 188.

The first access port 172 can be substantially centered with respect to the first damage site 170. The first expandable support device (not shown) can expand, as shown by arrows 64, substantially equidirectionally, aligned with the center of the first access port 172. The second access port 186 can be substantially not centered with respect to the second damage site 188. The second expandable support device (not shown) can substantially anchor to a side of the damage site 146 and/or the surface of the disc 144, and then expand, as shown by arrows 60, substantially directionally away from the disc 144.

Figure 68:
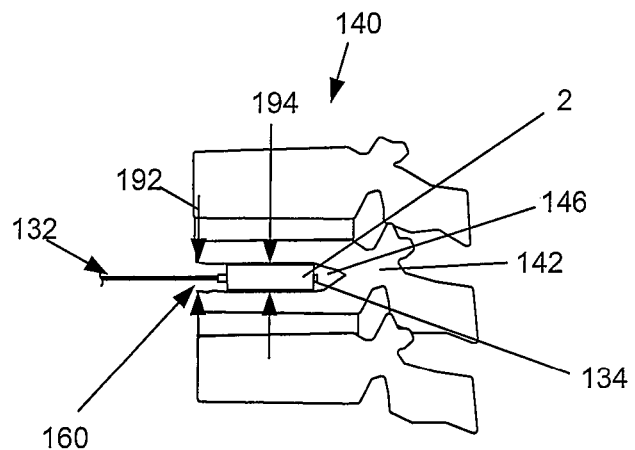
FIGS. 68 and 69 illustrate a variation of a method for deploying the expandable support device into the damage site in the vertebra.

FIG. 68 illustrates that the fluid pressure can be released from the balloon 134, and the balloon 134 can return to a pre-deployment configuration, leaving the expandable support element substantially fixed to the vertebra 142 at the damage site 146.

The access port 160 can have an access port diameter 192. The access port diameter 192 can be from about 1.5 mm (0.060 in.) to about 40 mm (2 in.), for example about 8 mm (0.3 in.). The access port diameter 192 can be a result of the size of the access tool 148 and in the unexpanded expandable support device 2. After the expandable support device 2 is deployed, the damage site 146 can have a deployed diameter 194. The deployed diameter 194 can be from about 1.5 mm (0.060 in.) to about 120 mm (4.7 in.), for example from about 10 mm (0.4 in.) to about 20 mm (0.8 in.), or from about 12 mm (0.47 in.) to about 16 mm (0.63 in.). The deployed diameter 194 can be greater than, equal to, or less than the access port diameter 192.

Figure 69:
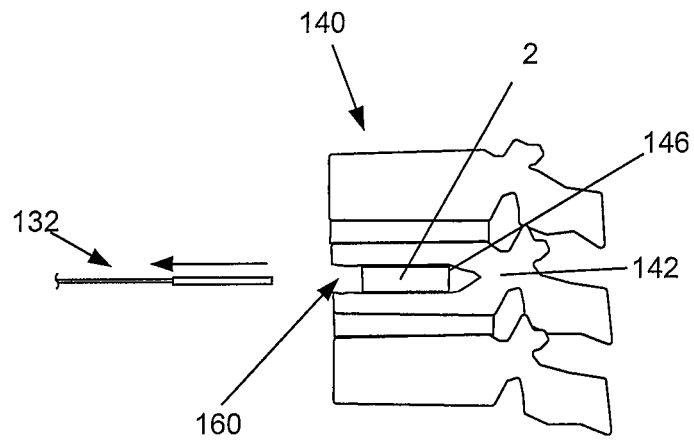

FIG. 69 illustrates that the deployment tool 132 can be removed, as shown, from the vertebra 142 after the expandable support device 2 is deployed.

Figure 70:
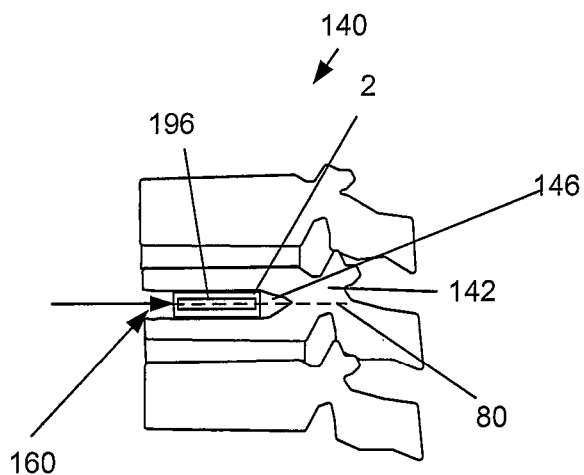
FIGS. 70 and 71 illustrate a variation of a method for deploying a locking pin into the expandable support device in the damage site in the vertebra.
Figure 71:
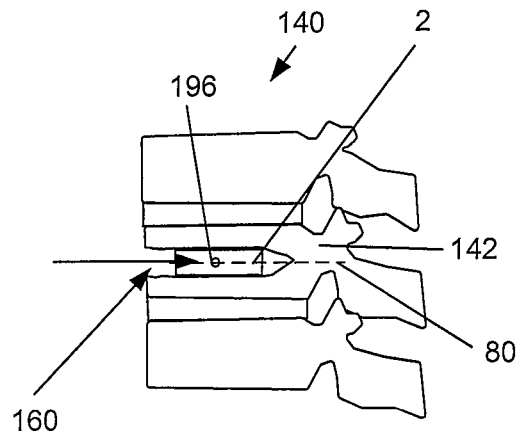

FIGS. 70 and 71 illustrate that a locking pin 196 can be inserted, as shown by arrow, into the deployed expandable support device 2, for example, after the expandable support device 2 is deployed in the vertebra 142. The locking pin 196 can prevent the expandable support device 2 from collapsing after the expandable support device 2 is deployed in the vertebra 142. The locking pin 196 can form an interference fit with the expandable support device 2 or may include features to hold the locking pin in place.

Figure 72:
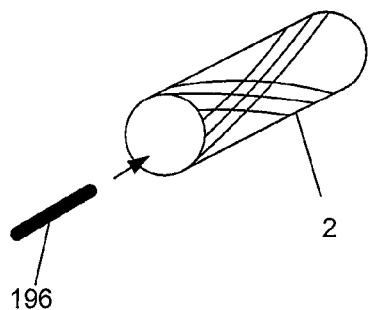
FIGS. 72 through 77 illustrate a variation of a method for deploying a locking pin into the expandable support device.

The locking pin 196 can be parallel with the longitudinal axis 80, as shown in FIG. 72, for example when the locking pin 196 is slidably received by and/or attached to the lock grooves 92 (see for example, FIG. 25). The locking pin 196 can be perpendicular to the longitudinal axis 80, as shown in FIG. 71, for example when the locking pin 196 is slidably received by and/or attached to ports formed between adjacent first struts 84 after the expandable support device 2 is expanded.

Figure 73:
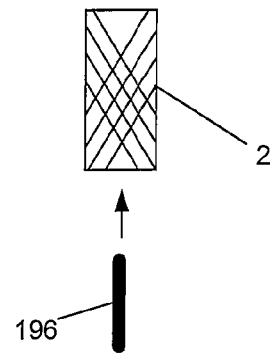
Figure 74:
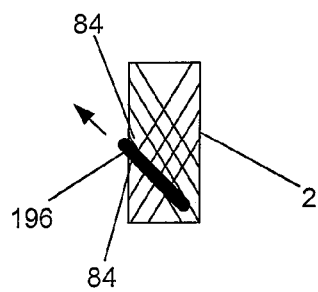
Figure 75:
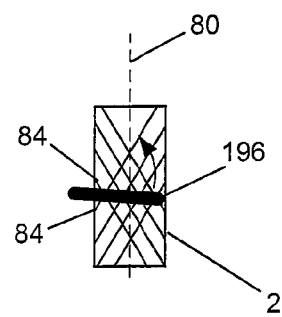
Figure 76:
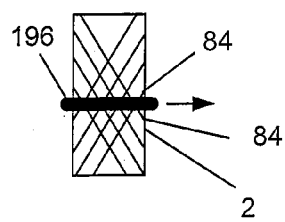
Figure 77:
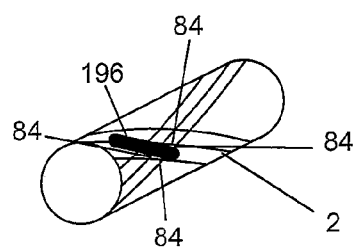

FIGS. 72 through 77 illustrate various methods for deploying the locking pin 196 into the expandable support device 2. As shown in FIGS. 72 and 73, the locking pin 196 can be translated, as shown by arrow, into the expandable support device 2 along the implant longitudinal axis. As shown in FIG. 74, a first end of the locking pin 196 can be translated, as shown by arrow, at an oblique angle, into a first port 16 formed between adjacent first struts 84. As shown by FIG. 75, a second end of the locking pin 196 can be rotated, as shown by arrow. As shown by FIG. 76, the second end of the locking pin 196 can be translated, as shown by arrow, into a second port 18 formed between adjacent first struts 84. FIG. 77 shows the locking pin 196 deployed into, and forming an interference fit with, the expandable support device 2.

Figure 78:
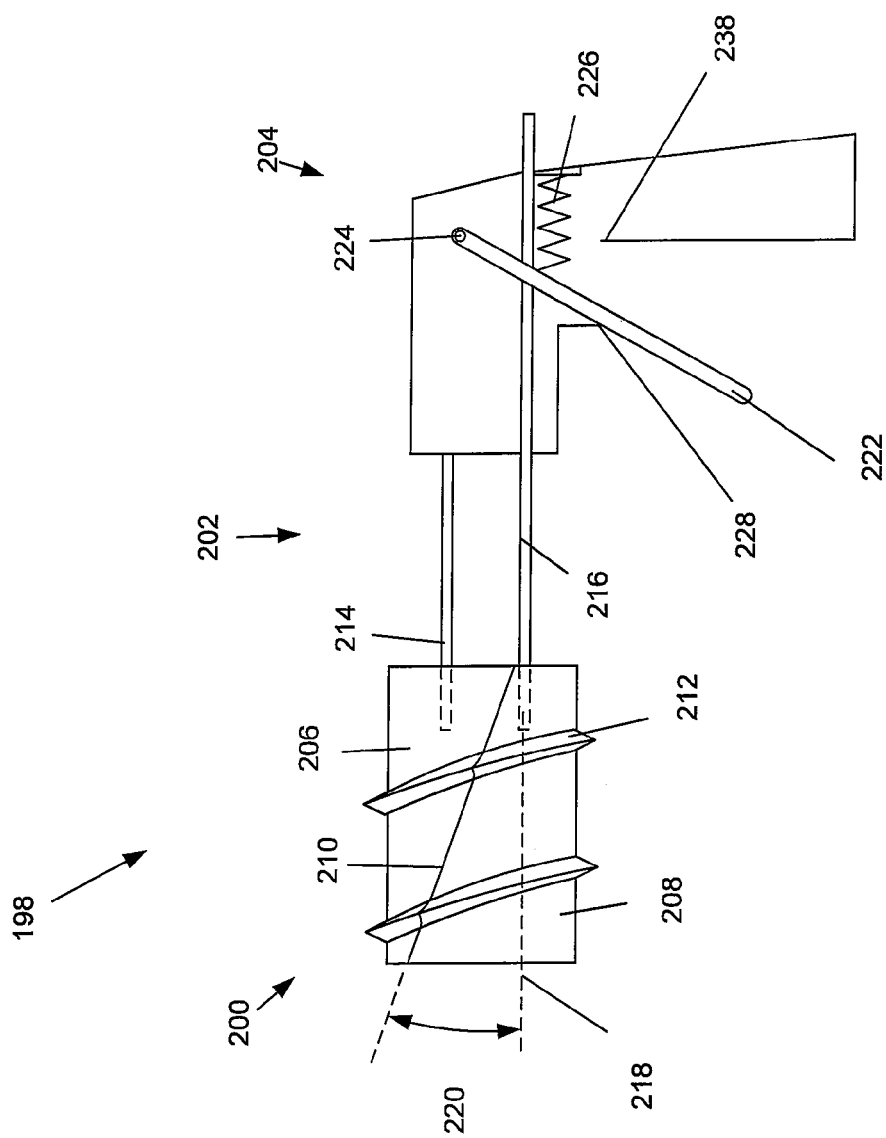
FIG. 78 illustrates a variation of the slidable expansion device.

FIG. 78 illustrates a slidable expansion device 198. The slidable expansion device 198 can have an expansion component 200, a deployment extension 202, a handle 204, or combinations thereof. The expansion component 200 can be configured to radially and/or longitudinally expand. The expansion component 200 can expand directly against tissue and/or expand an implant pre-loaded into the deployment site, and/or loaded onto or into the expansion component 200.

The expansion component 200 can have a first slidable element 206 and a second slidable element 208. The first and second slidable elements 206 and 208 can be configured to slide relative to each other. An interface 210 can be provided between the first slidable element 206 and the second slidable element 208. The expansion component 200 optionally can have an engagement element, such as an external engagement rib or thread 212. The external engagement thread 212 can spiral around the expansion component 200. The interface 210 can intersect the external engagement thread 212.

The deployment extension 202 can have a first extension arm 214 and a second extension arm 216. The first extension arm 214 can be fixedly attached to a third fixed element, such as the handle 204. The first extension arm 214 can be fixedly attached to the expansion component 200. The first extension arm 214 can maintain a substantially constant distance between the handle 204 and the first slidable element 206. The second extension arm 216 can be fixedly attached to the slidable expansion device 198 and slidably attached to the third fixed element, such as the handle 204.

The angle between an extension arm longitudinal axis 218, such as an axis extending along the second extension arm 216, and the interface 210 can form an expansion angle 220. The expansion angle 220 can be from about 0° to about 85°, more narrowly from about 10° to about 45°, for example about 30°.

The handle 204 can have an activation system configured to expand the expansion component 200. For example, the handle 204 can have a lever 222 than can be fixedly or rotatably attached to the second extension arm 216. The lever 222 can be rotatably attached to a lever pivot 224. The lever pivot 224 can be fixedly attached to a case of the handle 204. A return spring 226 can be attached to the lever 222. The return spring 226 can apply a force against the lever 222 sufficient to keep the lever 222 against a first stop 228 when the slidable expansion device 198 is not in use.

Figure 79:
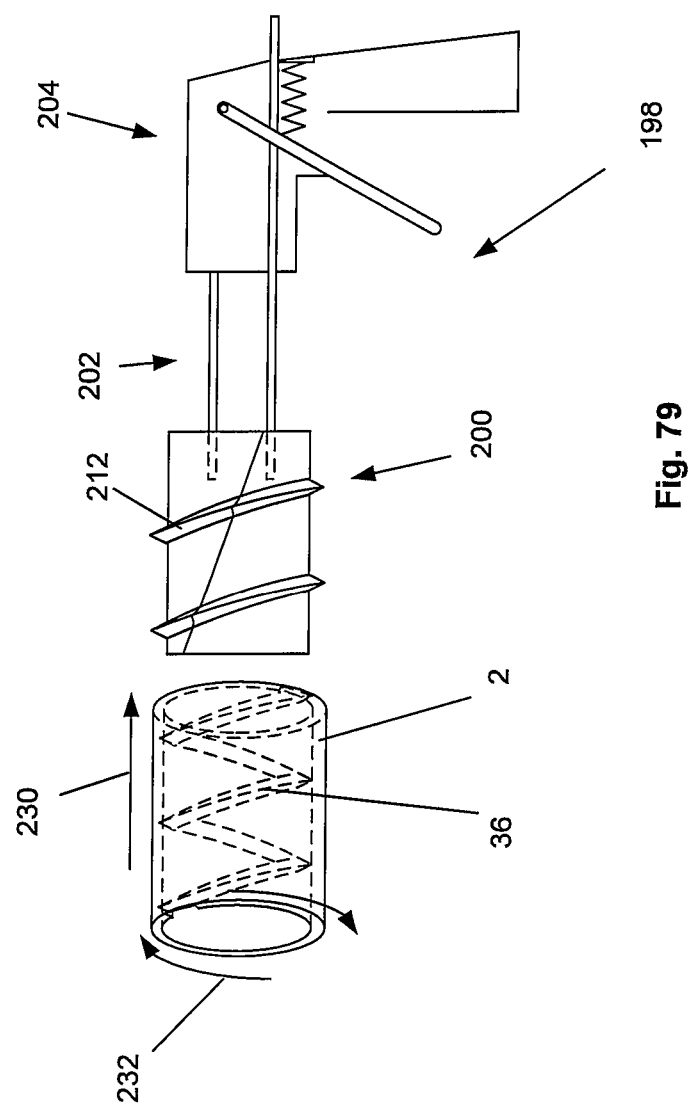
FIG. 79 illustrates a variation of a method for loading the expandable support device of FIG. 10 onto the slidable expansion device of FIG. 78.

FIG. 79 illustrates that the expandable support device 2 can be loaded onto the expansion component 200 of the slidable expansion device 198. The expandable support device 2 can be translated, as shown by arrow 230, to the expansion component 200. The optional engagement groove 36 can be aligned with and engage the optimal external engagement rib or thread 212, such as by rotating the expandable support device 2, to engage thread and load the expandable support device 2 onto the expansion component 200.

Figure 80:
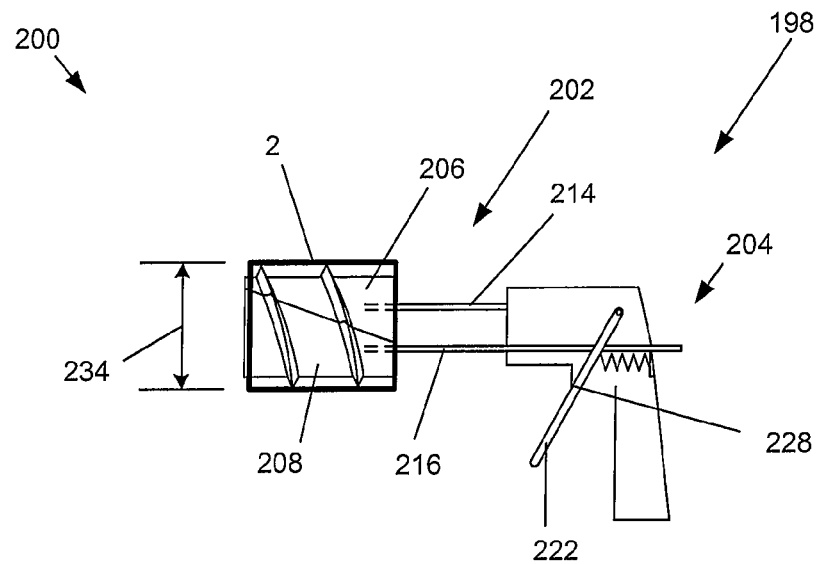
FIGS. 80 and 81 illustrate a variation of a method for using the slidable expansion device.

FIG. 80 illustrates that, when loaded on the slidable expansion device 198, the expandable support device 2 (shown in see-through without details) can have an expandable support device diameter 234.

Figure 81:
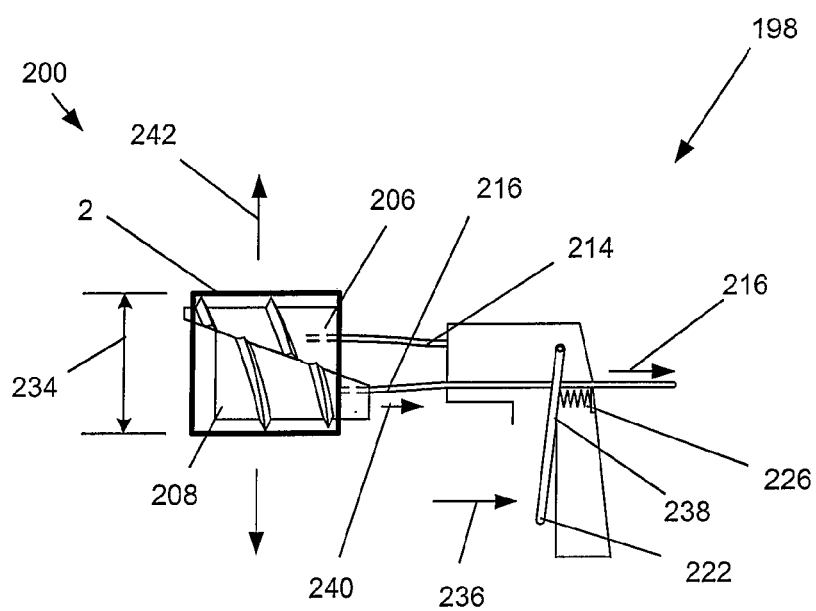

FIG. 81 illustrates that the lever 222 can be forced to retractably rotate, as shown by arrow 236, the second extension arm 216. The movement of the lever 222 can compress the return spring 226. The rotation of the lever 222 can be limited by physical interference at the second stop 238. The translation of the second extension arm 216 can, in turn, translate, as shown by arrow 240 the second slidable element 208. As the second slidable element 208 translates along the interface 210, the second slidable element 208 can shift downward (with respect to the page) and the first slidable element 206 can shift upward, thereby causing expansion, as shown by arrows 242, of the expansion component 200 and the expandable support device 2. The expandable support device diameter 234 can be larger after expansion than before expansion. The first extension arm 214 and/or the second extension arm 216 can resiliently and/or deformably flex during expansion of the expansion component 200.

Figure 82:
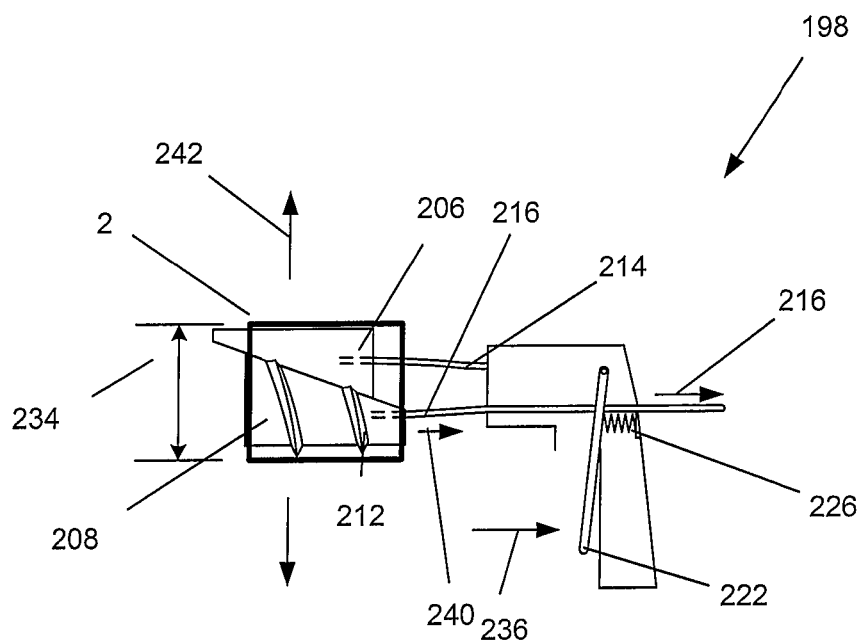
FIG. 82 illustrates a variation of a method for using the slidable expansion device.

FIG. 82 illustrates that the first and/or second slidable element 206 and/or 208 can have no external engagement thread 212. The first and/or second slidable element 206 and/or 208 can be coated or lubricated with a low-friction material, such as TEFLON® (i.e., PTFE) from E. I. Du Pont de Nemours and Company, Wilmington, Del.

Figure 83:
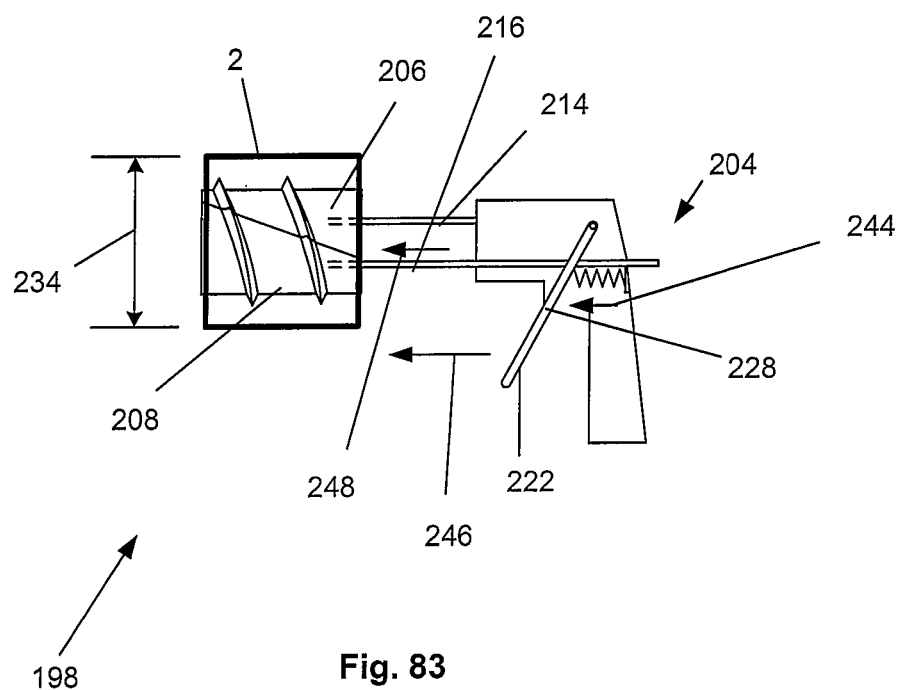
FIG. 83 illustrates a variation of a method for using the slidable expansion device.

FIG. 83 illustrates that the force can be removed from the lever 222. The return spring 226 can translate, as shown by arrow 244. The lever 222 can be rotated, as shown by arrow 246, by the return spring 226. The first stop 228 can limit the rotation of the lever 222. The second extension arm 216 can translate, as shown by arrow 248, the second slidable element 208. The expansion component 200 can return to a contracted configuration. The expansion component 200 can be removed from the then-expanded expandable support device 2. While the deployment device of FIGS. 78-83, for example, shows a pistol type grip with a compressible handle, it also is contemplated that the device could be actuated by a rotational motion about the longitudinal axis of the deployment component.

Figure 84:
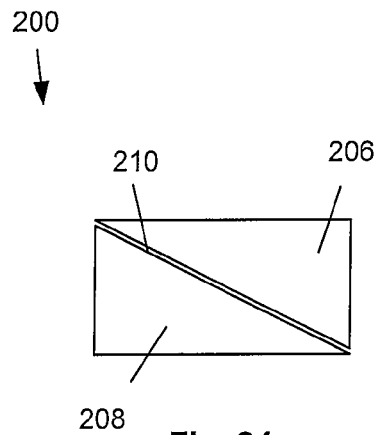
FIGS. 84 and 85 show side and front views, respectively, of a variation of the expansion component.
Figure 85:
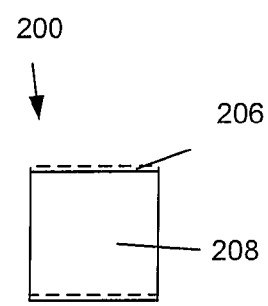

FIGS. 84 and 85 illustrate that the expansion component 200 can have a substantially triangular, or wedge-shaped first and second slidable elements 206 and 208. As discussed above with respect to FIGS. 15 and 16, wedge shaped elements 96 and 98 may be incorporated into the expandable device. Translation of wedges within the device can assist in the deployment of the expandable device and may provide reinforcement for the deployed device. In this regard, it is contemplated that the various wedge, locking pin or buttress configurations disclosed herein could aid in deployment and provide rigid support for the expandable device. By way of example, wedge configurations as shown in FIGS. 84-99, which may include interlocking directional teeth or a tongue and groove interface as described with regard to the buttress of FIGS. 133-135, may be included as part of the expandable device. These features can provide expansion force to the device and added support and rigidity to the device in addition to struts 10, 12. The combined effect of the wedges with the struts provides the desirable combination of controlled expansion of the device with balanced counterforces within the device (the wedges opposing the struts and vice versa) so that the device may be deployed to the desired location and degree of expansion, the counterforce of the interlocking wedges and the struts establishing a uniform structure not prone to release or collapse.

Figure 86:
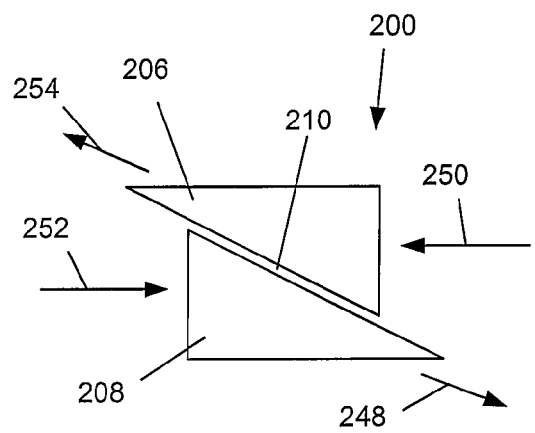
FIGS. 86 and 87 show side and front views, respectively, of a variation of a method for using the variation of the expansion component of FIGS. 84 and 85.
Figure 87:
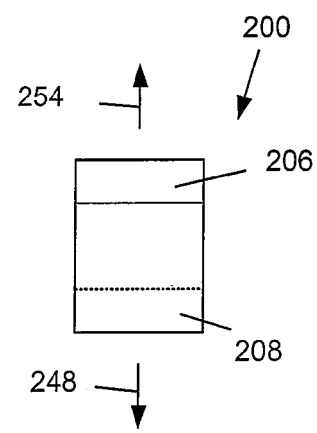

FIGS. 86 and 87 illustrate that a first slidable element force, shown by arrow 250, can be applied to the first slidable element 206 in substantially the opposite direction as a second slidable element force, shown by arrow 252, can be applied to the second slidable element 208. The first slidable element 206 and the second slidable element 208 can translate, as shown by arrows 254 and 248, in opposite directions with respect to each other parallel to the interface 210 to cause expansion.

Figure 88:
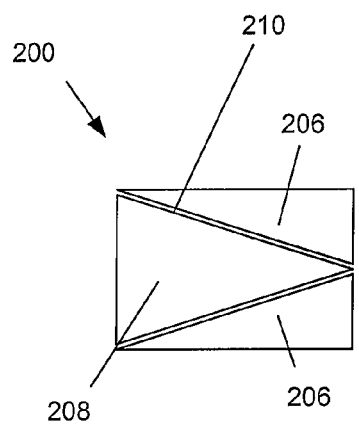
FIGS. 88 and 89 show side and front views, respectively, of a variation of the expansion component.
Figure 89:
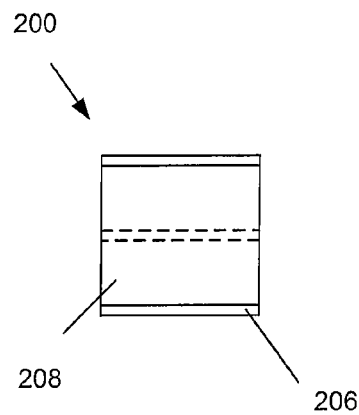

FIGS. 88 and 89 illustrate that the expansion component 200 can have substantially triangular or wedge-shaped first and second slidable elements 206 and 208. The expansion component 200 can have multiple first slidable elements 206 and multiple interfaces 210.

Figure 90:
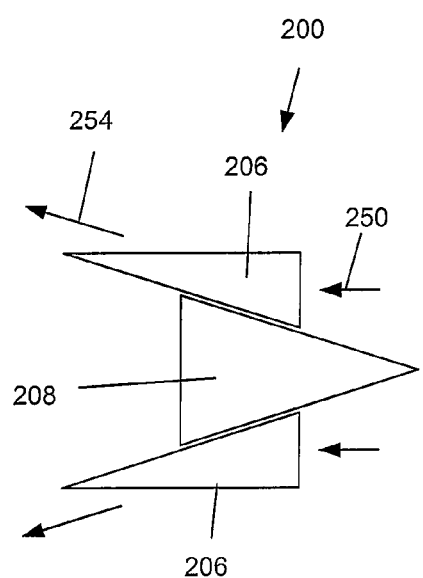
FIGS. 90 and 91 show side and front views, respectively, of a variation of a method for using the variation of the expansion component of FIGS. 88 and 89.
Figure 91:
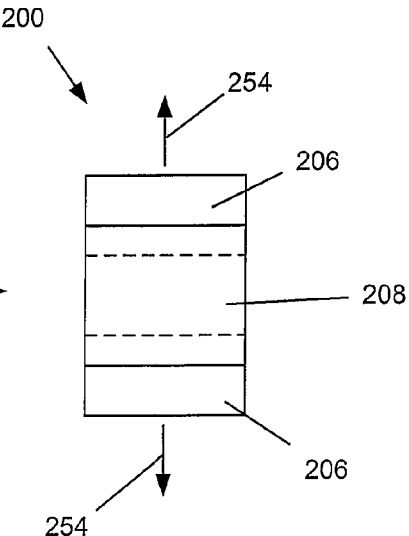

FIGS. 90 and 91 illustrate that a first slidable element force, shown by arrow 250, can be applied to the first slidable elements 206 in substantially the opposite direction as a second slidable element force, shown by arrow 252, can be applied to the second slidable element 208. The first slidable elements 206 and the second slidable element 208 can translate, as shown by arrows 254 and 248.

FIGS. 92 and 93 illustrate that the expansion component 200 can have a first slidable element 206 that can be flexibly resilient or deformably and can have a conical port therein. The second slidable element 208 can be substantially conical and can be positioned in the conical port of the first slidable element 206.

FIGS. 94 and 95 illustrate that a first slidable element force, shown by arrow 250, can be applied to the first slidable element 206 in substantially the opposite direction as a second slidable element force, shown by arrow 252 can be applied to the second slidable element 208. The first slidable element 206 can translate, as shown by arrows 254. The first slidable element 206 can resiliently or deformably expand radially outward.

FIGS. 96 and 97 illustrate that the expansion component 200 can have multiple first slidable elements 206 that can be flexibly resilient or deformably and can have a conical port therein. The first slidable elements 206 can be segmented or separated by element separations 148. The element separations 256 can be thinned and very low resistant or completely severed areas or lines (as shown). The second slidable element 208 can be substantially conical and can be positioned in the conical port of the first slidable element 206.

FIGS. 98 and 99 illustrate that first slidable element forces, shown by arrow 250, can be applied to the first slidable elements 206 in substantially the opposite direction as a second slidable element force, shown by arrow 252, can be applied to the second slidable element 208. The first slidable elements 206 can translate, as shown by arrows 254. The first slidable elements 206 can resiliently or deformably expand radially outward. The first slidable elements 206 can be attached by a filament or thin strip of material (not shown), or can be distinct and unattached to each other.

Figure 100:
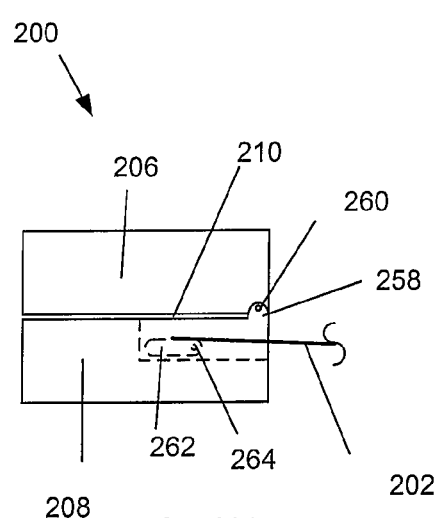
FIGS. 100 and 101 show side and front views, respectively, of a variation of the expansion component.
Figure 101:
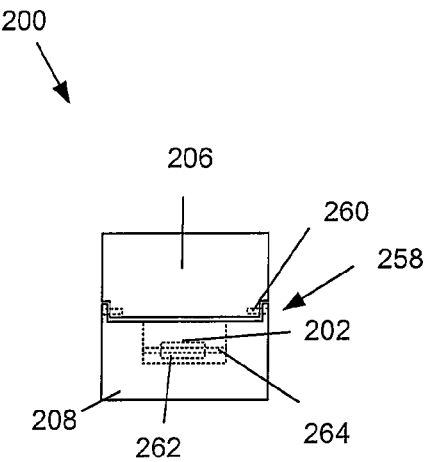

FIGS. 100 and 101 illustrate that the expansion component 200 can have a first slidable element 206 that can be rotatably attached to a second slidable element 208 via a hinge 150. The hinge 258 can rotate about a hinge pin 260 that can pass through the first slidable element 206 and the second slidable element 208. The second slidable element 208 can have a cam 262. A camshaft 264 can rotatably attach the cam 262 to the second slidable element 208. The cam 262 can be attached to all or part of the deployment extension 202. The cam 262 can be located in a depression or cavity in the second slidable element 208.

Figure 102:
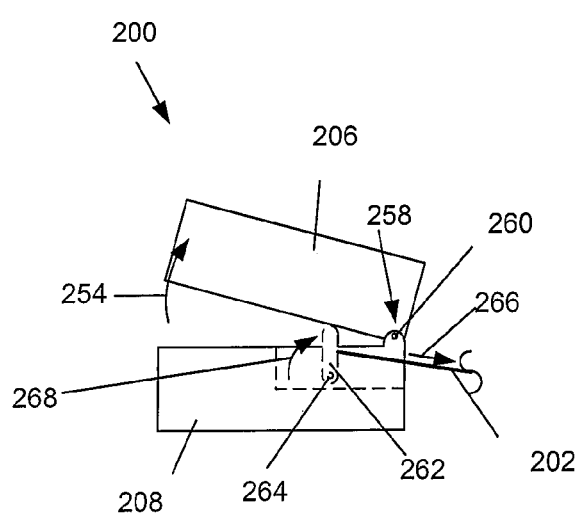
FIGS. 102 and 103 show side and front views, respectively, of a variation of a method for using the variation of the expansion component of FIGS. 100 and 101.
Figure 103:
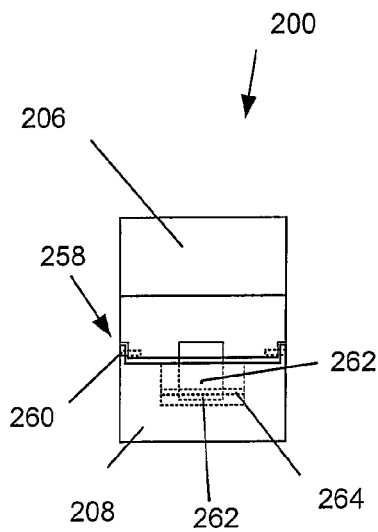

FIGS. 102 and 103 illustrate that the deployment extension 202 can be translated, as shown by arrow 266. This translation can rotate, as shown by arrow 268, the cam 262. The cam 262 can slide along the first slidable element 206 and can cause the first slidable element 206 to rotate, as shown by arrow 254, about the hinge pin 260.

Figure 104:
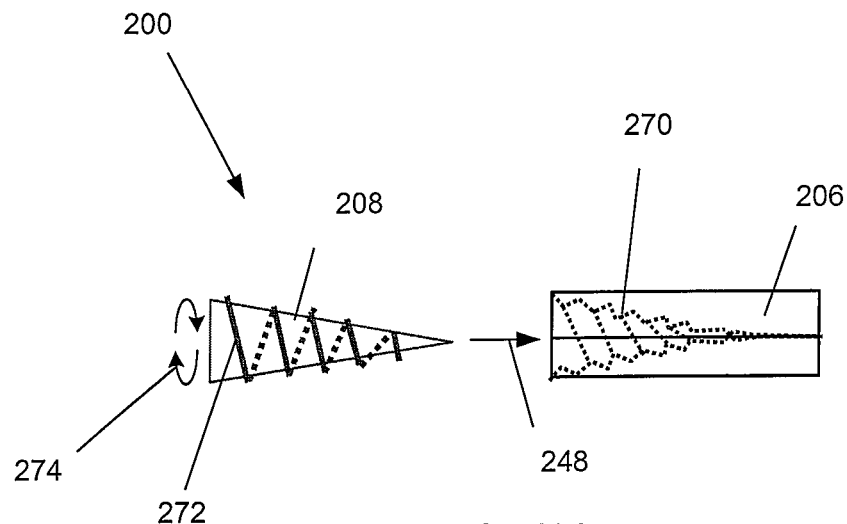
FIGS. 104 and 105 illustrate a variation of the expansion component and a variation of a method for using the expansion component.

FIG. 104 illustrates that the first slidable element 206 can have a slidable element port 270. The slidable element port 270 can be shaped (e.g., grooved or threaded) to receive the second slidable element 208. The second slidable element 208 can be conical. The second slidable element 208 can have a slidable element thread 272. The slidable element port 270 can be threaded. The second slidable element 208 can be translated, as shown by arrow 248 and rotated, as shown by arrow 274, as the second slidable element 208 approaches the slidable element port 270.

Figure 105:
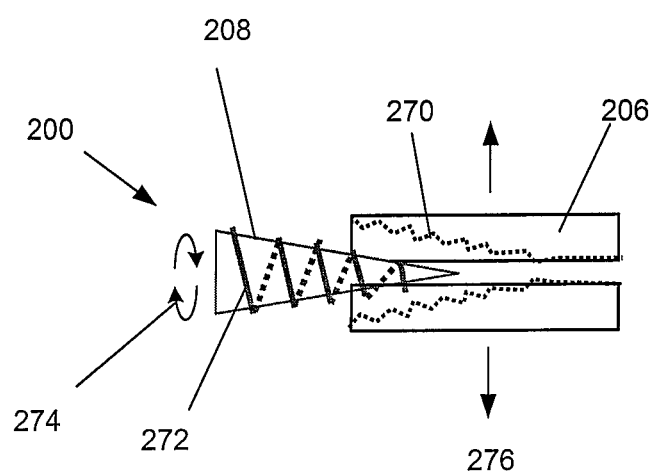

FIG. 105 illustrates that the second slidable element 208 can enter the slidable element port 270. The first slidable element 206 can expand, as shown by arrows 276, as the slidable element port 270 receives the second slidable element 208. The slidable element thread 272 can engage the slidable element port 270. The second slidable element 208 can be rotated, as shown by arrows 274, as the second slidable element 208 enters the first slidable element 206.

Figure 106:
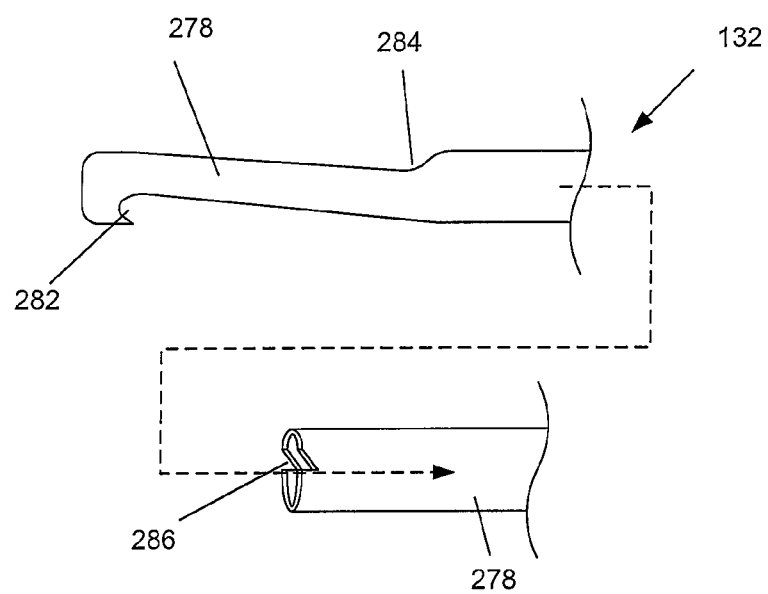
FIGS. 106 and 107 illustrate a variation of a deployment tool.

FIG. 106 illustrates an alternative deployment tool 132 can having a shaft 278 and a sleeve 280. The shaft 278 can be slidably received, as shown by arrow, by the sleeve 280. The shaft 278 can have a first catch 282. The shaft 278 can have a relief 284 section or an additional catch on a side opposite the first catch 282. The sleeve 280 can have a second catch 286.

Figure 107:
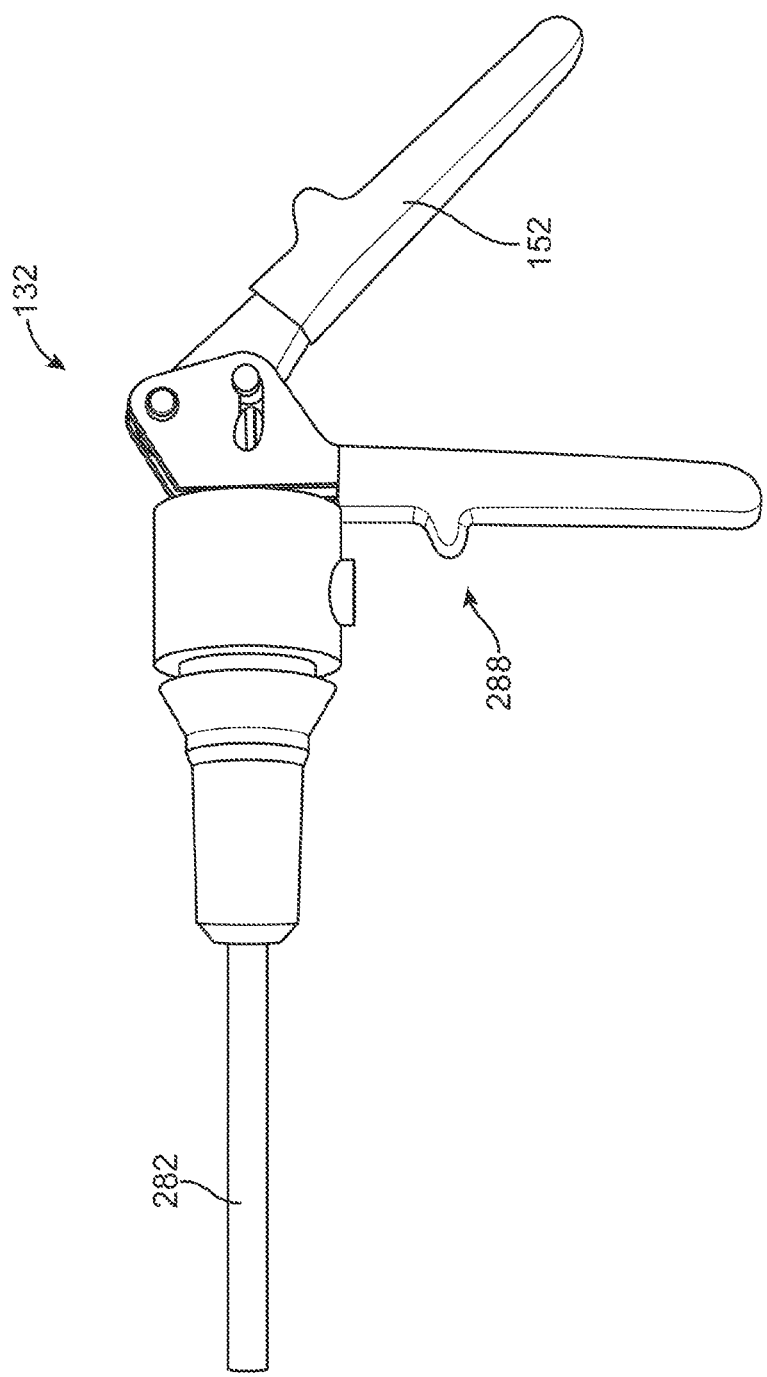

FIG. 107 illustrates that the deployment tool 132 can have an actuator 288, such as an ergonomic lever handle 152. The handle 152 can be attached to the sleeve 280. When the shaft 278 is received in the sleeve 280, the actuator 288 can be attached to the shaft 278. Applying a force to the actuator 288 can cause the shaft 278 to slide or translate in the sleeve 280.

Figure 108:
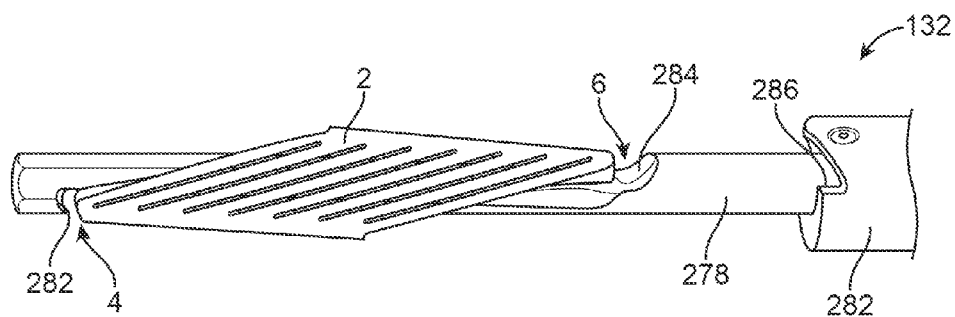
FIGS. 108 through 110 illustrate a variation of a method of expanding the expandable support device using the deployment tool of FIGS. 106 and 107.

FIG. 108 illustrates that the expandable support device 2, for example in a contracted configuration, can be loaded on the shaft 278. The first end 4 of the expandable support device 2 can be received by and/or interference fit in the first catch 282. The second end 6 of the expandable support device 2 can be received by and/or interference fit in the relief 284. The first and/or second end 6 of the expandable support device 2 can be beveled. The beveled ends can be shaped to fit the first catch 282 and/or relief 284.

Figure 109:
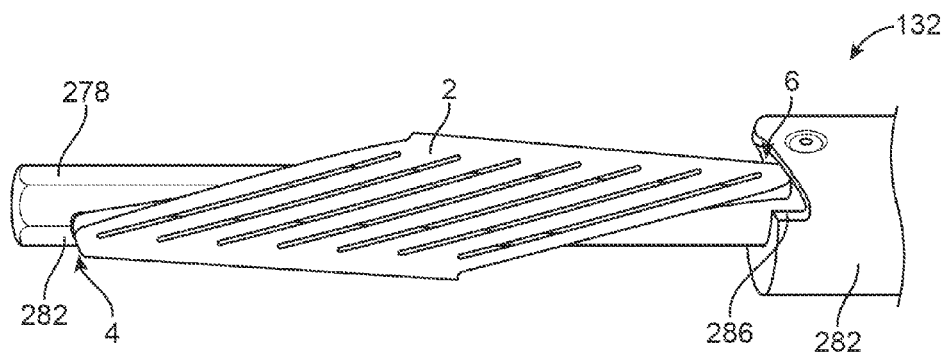

FIG. 109 illustrates that the shaft 278 can slide, as shown by arrow, relative to the sleeve 282. The second end 6 of the expandable support device 2 can be received by and/or engage the second catch 286. The second end 6 can interference fit the second catch 286.

Figure 110:
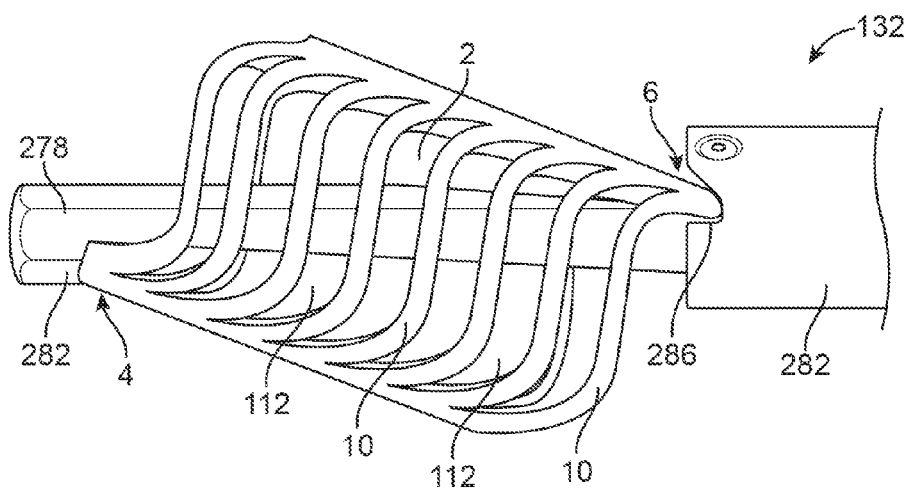

FIG. 110 illustrates that the shaft 278 can be forcibly slid into the sleeve 282 by squeezing the lever handle (see FIG. 107). The expandable support device 2 can be squeezed between the first catch 282 and the second catch 286. The expandable support device 2 can be resiliently and/or deformably forced into an expanded configuration. The expandable support device 2 can be released from the deployment tool 132, for example, by releasing the shaft 278 from the handle and sliding the shaft 278 distally through the sleeve 282.

Figure 111:
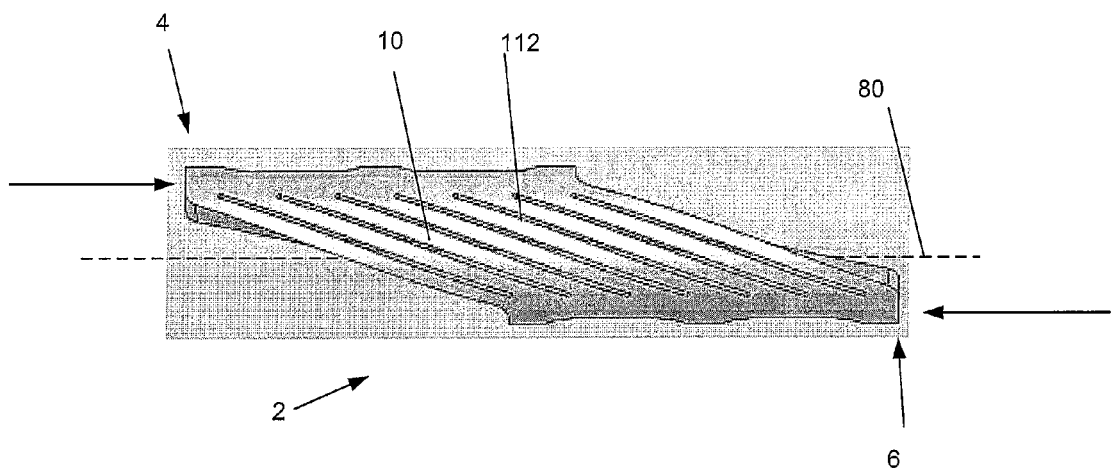
FIGS. 111 and 112 are schematic illustrations of the forces acting on the expandable support device as illustrated in FIGS. 108-110.
Figure 112:
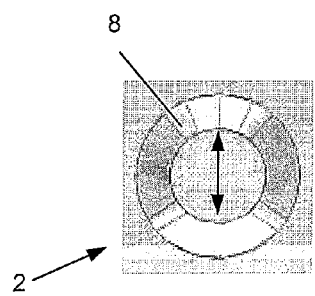

FIG. 111 illustrates that the expandable support device 2 can be expanded by applying force, as shown by arrows, on the first end 4 and the second end 6, and by directing the force toward the expandable support device 2. FIG. 112 illustrates that the expandable support device 2 can be expanded by applying force, as shown by arrows, radially outward against the wall 8.

Figure 113:
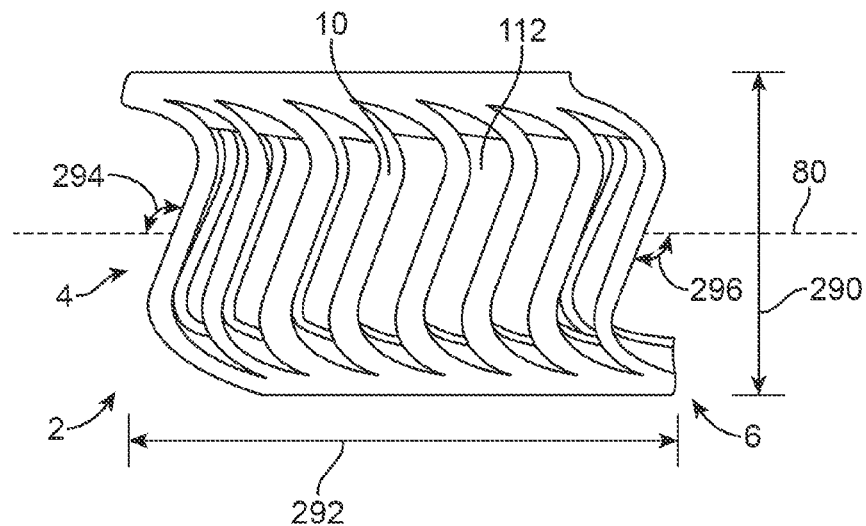
FIGS. 113 and 114 illustrate a variation of the expandable support device in an expanded configuration.
Figure 114:
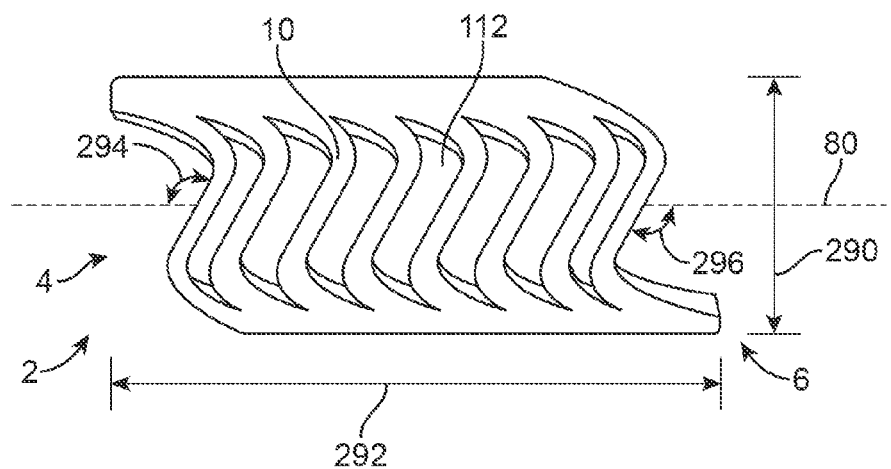

FIGS. 113 and 114 illustrate various variations of the expandable support device 2 in an expanded configuration. The wall openings 112 can expand when the expandable support device 2 is in an expanded configuration.

The expandable support device 2 can have an expanded height 290 and an expanded length 292. The expanded height 290 can be from about 0.3 cm (0.1 in.) to about 5 cm (2 in.), for example about 2 cm (0.6 in.). The expanded length 292 can be from about 0.1 cm (0.05 in) to about 3.8 cm (1.5 in.), for example about 3 cm (1 in.). The expandable support device 2 can have first 294 and second 296 expanded intersection angles. The first expanded intersecting angle 294 can be substantially equal to the second expanded intersecting angle 296. The expanded intersecting angles can be from about 45° to about 135°, for example about 110°, also for example about 90 °.

Figure 115:
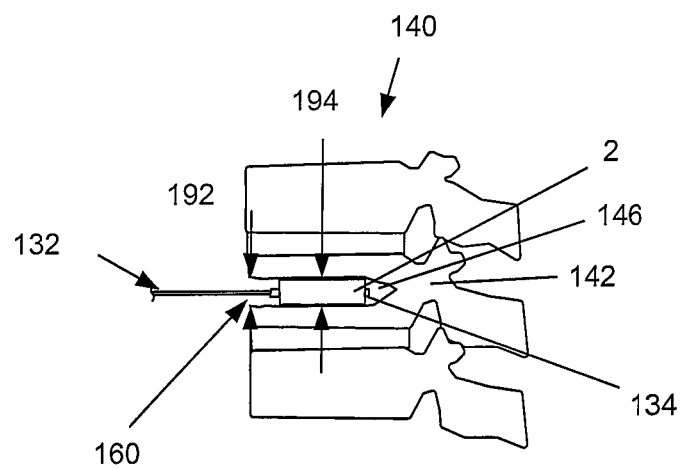
FIGS. 115 and 116 illustrate a variation of a method for deploying the expandable support device into the damage site in the vertebra.

FIG. 115 illustrates that the fluid pressure can be released from the balloon 134, and the balloon 134 can return to a pre-deployment configuration, leaving the expandable support element substantially fixed to the vertebra 142 at the damage site 146.

The access port 160 can have an access port diameter 192. The access port diameter 192 can be from about 1.5 mm (0.060 in.) to about 40 mm (2 in.), for example about 8 mm (0.3 in.). The access port diameter 192 can be a result of the size of the access tool 148. After the expandable support device 2 is deployed, the damage site 146 can have a deployed diameter 194. The deployed diameter 194 can be from about 1.5 mm (0.060 in.) to about 120 mm (4.7 in.), for example about 20 mm (0.8 in.). The deployed diameter 194 can be greater than, equal to, or less than the access port diameter 192.

Figure 116:
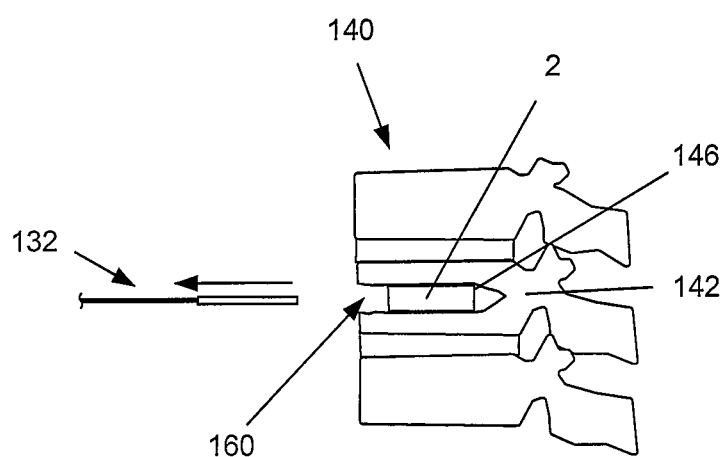

FIG. 116 illustrates that the deployment tool 132 can be removed, as shown by arrow, from the vertebra 142 after the expandable support device 2 is deployed.

Figure 117:
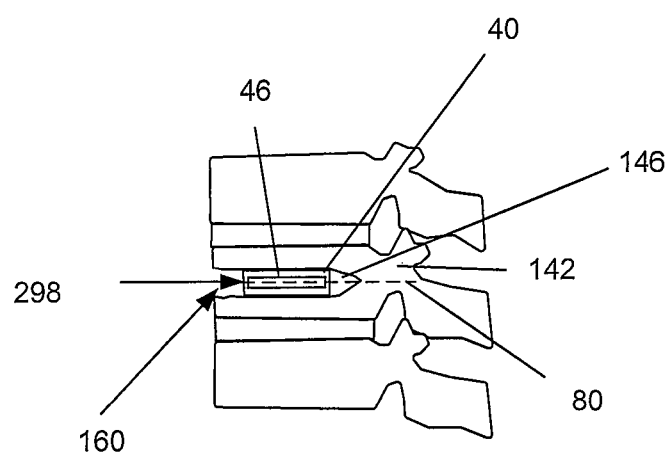
FIG. 117 illustrates a variation of a method for deploying a second expandable support device or locking pin in the damage site in the vertebra.

FIG. 117 illustrate that a second expandable support device 46 and/or locking pin 196 can be inserted, as shown by arrow 298, into the first deployed expandable support device 2, for example, after the first expandable support device 40 is deployed in the vertebra 142. The second expandable support device 46 and/or locking pin 196 can prevent the first expandable support device 40 from collapsing after the first expandable support device 40 is deployed in the vertebra 142. The second expandable support device 46 and/or locking pin 196 can form an interference fit with the expandable support device 2.

Figure 118:
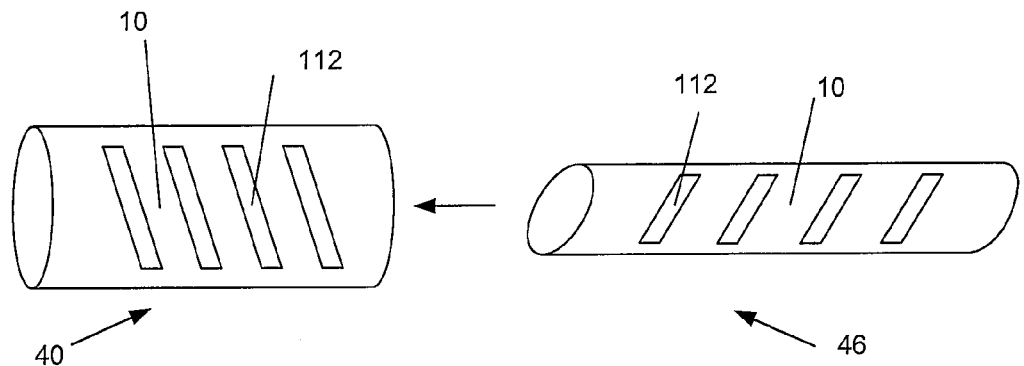
FIGS. 118 through 120 illustrate a method for deploying a second expandable support device in the vertebra.

FIG. 118 illustrates that the second expandable support device 46 can be translated, as shown by arrow, into the first expandable support device 40. The first expandable support device 40 can be in an expanded, contracted, or other configuration. The second expandable support device 46 can be in an expanded, contracted, or other configuration. The struts 10 and/or wall openings 112 of the first expandable support device 40 can be angled in a substantially opposite direction to the struts 10 and/or wall openings 112 of the second expandable support device 46.

Figure 119:
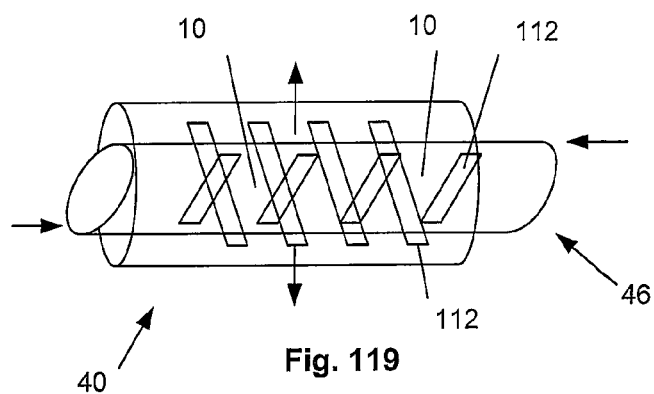

FIG. 119 illustrates that after the second expandable support device 46 is inside the first expandable support device 40, the second expandable support device 46 can be subject to any or all of the expansion forces, as shown by arrows.

Figure 120:
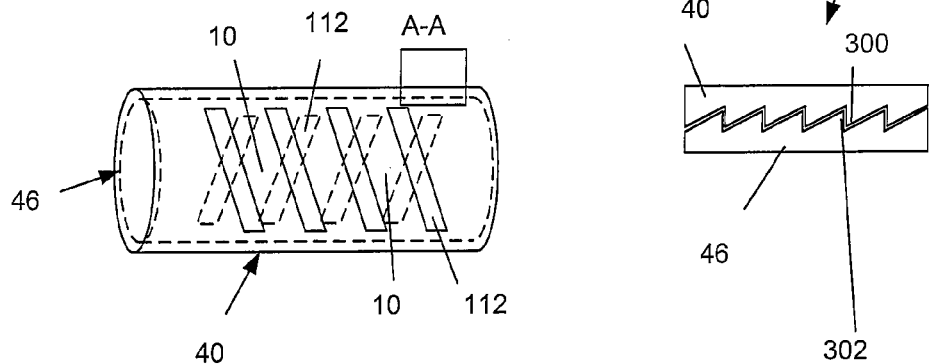

FIG. 120 illustrates that the second expandable support device 46 can be in an expanded configuration in the first expandable support device 40. The second expandable support device 46 can be translated into the first expandable support device 40 and expanded, as shown in FIGS. 118 and 119. The second expandable support device 46 can be in an expanded configuration and screwed or otherwise attached into the first expandable support device 40.

Figure 121:
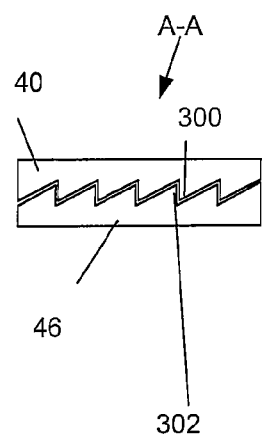
FIG. 121 is a close-up view of a variation of section A-A of FIG. 120.

FIG. 121 illustrates that the first expandable support device 40 can be rotatably attached to, or have an interference fit with, the second expandable support device 46. The first expandable support device 40 can have first teeth 300, for example on the inside surface of the wall 8. The second expandable support device 46 can have second teeth 302, for example on the outside surface of the wall 8. The first teeth 300 can engage the second teeth 302.

Figure 122:
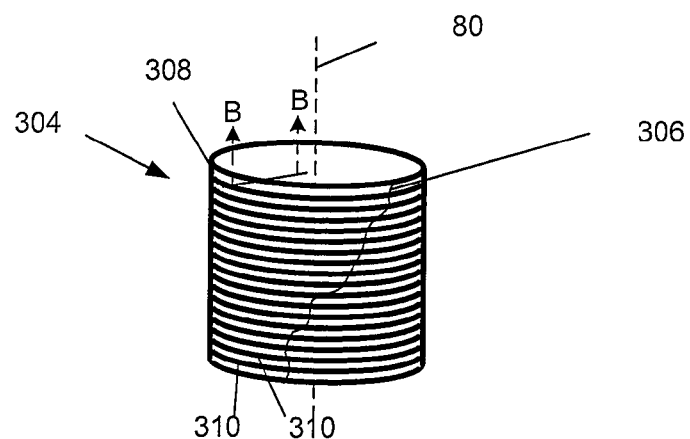
FIG. 122 illustrates a variation of a buttress.

FIG. 122 illustrates a buttress 304. The buttress 304 can have a longitudinal axis 80. The buttress 304 can have a tensioner 306. A first end 4 of the tensioner 306 can be fixedly or removably attached a first end 4 of the buttress 304. A second end 6 of the tensioner 306 can be fixedly or removably attached a second end 6 of the buttress 304. The tensioner 306 can be in a relaxed configuration when the buttress 304 is in a relaxed configuration. The tensioner 306 can create a tensile force between the first end 4 of the buttress 304 and the second end 6 of the buttress 304 when the buttress 1304 is in a stressed configuration. The tensioner 306 can be, for example, a resilient wire, a coil, spring, an elastic member, or combinations thereof.

Figure 123:
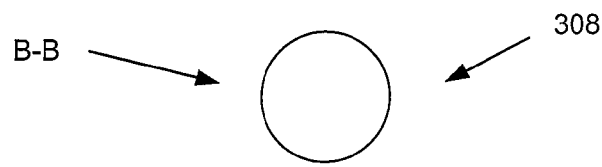
FIGS. 123 through 125 illustrate variations of section B-B of the buttress of FIG. 122.
Figure 124:
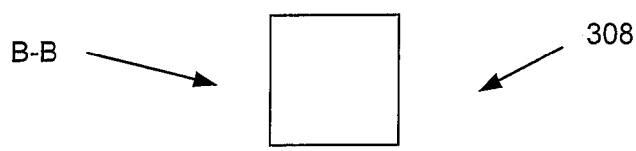
Figure 125:

The buttress 304 can have a coil 308. The coil 308 can have turns 310 of a wire, ribbon, or other coiled element. FIGS. 123 through 125 illustrate that the coil 310 can be made from a wire, ribbon, or other coiled element having a circular, square, or oval cross-section, respectively.

The buttress 304 can be a series of connected hoops.

Figure 126:
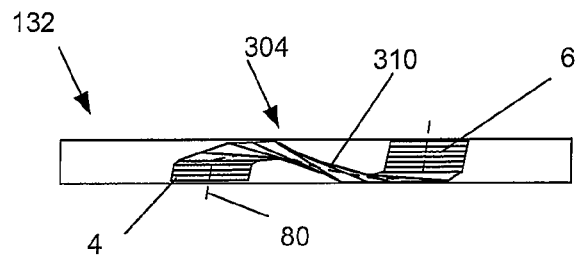
FIGS. 126 through 128 illustrate a variation of a method for deploying a buttress.

FIG. 126 illustrates that the buttress 304 can be loaded into a hollow deployment tool 132 in a smear (i.e., partially shear stressed) configuration at a smear section 310. The buttress 304 in the smear section 310 can have a relaxed first end 4, a stressed smear section 310, and a relaxed second end 6. The longitudinal axis 80 can be not straight (i.e., non-linear) through the smear section 310.

Figure 127:
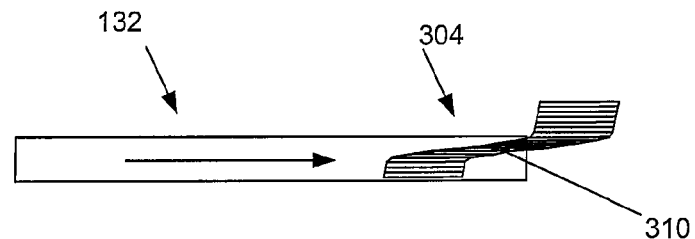

FIG. 127 illustrates that part of the buttress 304 can be forced, as shown by arrow, out of the deployment tool 132. The second end 6 can exit the deployment tool 132 before the remainder of the buttress 304. The smear section 310 can then partially relax. The second end 6 can be positioned to a final location before the remainder of the buttress 304 is deployed from the deployment tool 132.

Figure 128:
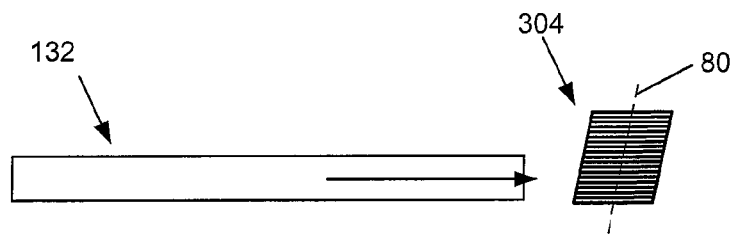

FIG. 128 illustrates that the remainder of the buttress 304 can be forced, as shown by arrow, out of the deployment tool 132. The smear section 310 can substantially relax. The longitudinal axis 80 can return to a substantially relaxed and/or straight (i.e., linear) configuration.

Figure 129:
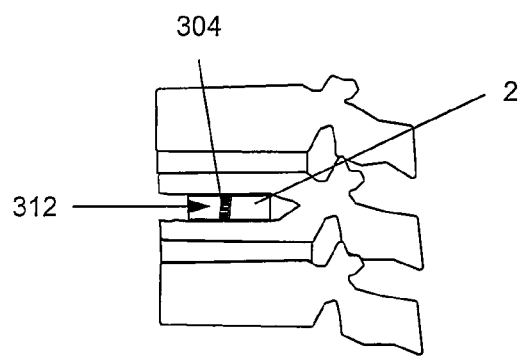
FIG. 129 illustrates a variation of a method for deploying a buttress.

FIG. 129 illustrates that the buttress 304 can be deployed 312 in the expandable support device 2, for example with the longitudinal axis 80 of the buttress 304 or the strongest orientation of the buttress 304 aligned substantially parallel with the primary load bearing direction (e.g., along the axis of the spine) of the expandable support device 2.

Figure 130:
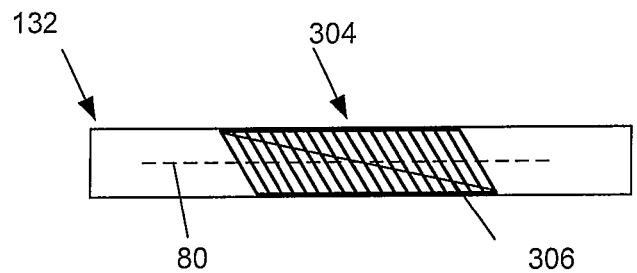
FIGS. 130 through 132 illustrate a variation of a method for deploying a buttress

FIG. 130 illustrates that the buttress 304 can be loaded into the hollow deployment tool 132 with the longitudinal axis 80 of the buttress 1304 substantially parallel with the hollow length of the deployment tool 132. The entire length of the buttress 304 can be under shear stress.

Figure 131:
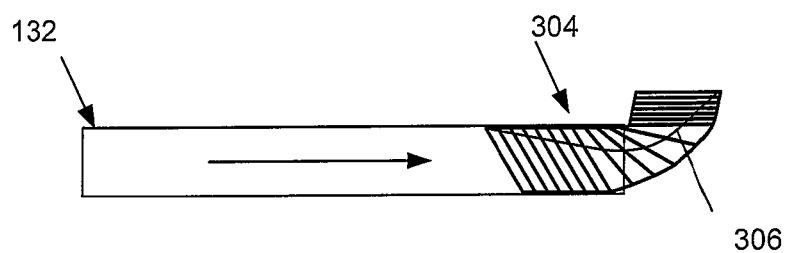

FIG. 131 illustrates that part of the buttress 304 can be forced, as shown by arrow, out of the deployment tool 132.

The second end 6 of the buttress 304 can exit the deployment tool 132 before the remainder of the buttress 304. The tensioner 306 can apply a tensile stress between the ends of the buttress 304, for example, forcing the deployed second end 6 of the buttress 304 to "stand up straight". The second end 6 of the buttress 304 can be positioned to a final location before the remainder of the buttress 304 is deployed from the deployment tool 132.

Figure 132:
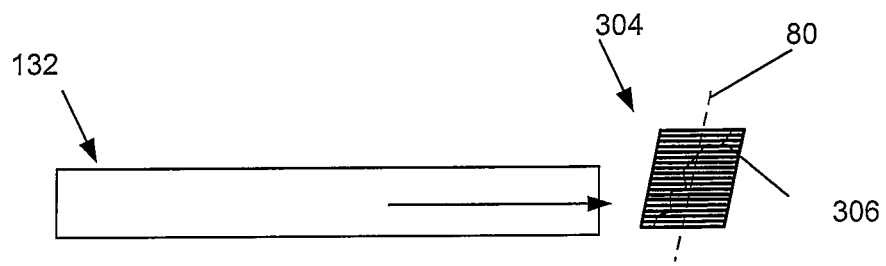

FIG. 132 illustrates that the remainder of the buttress 304 can be forced, as shown by arrow, out of the deployment tool 132. The buttress 304 can substantially relax.

FIG. 133 illustrates that the buttress 304 can have a first wedge 66 and a second wedge 68. The first wedge 66 can contact the second wedge 68 at a directionally locking interface 314. The directionally locking interface 314 can have directional teeth 316.

FIG. 134 illustrates that the first wedge 66 can be slidably attached to the second wedge 68. The first wedge 66 can have a tongue 318. The second wedge 68 can have a groove 320. The tongue 318 can be slidably attached to the groove 320.

A gap 322 can be between the tongue 318 and the groove 320. The gap 322 can be wider than the height of the teeth 316. The gap 322 can be configured to allow the first wedge 66 to be sufficiently distanced from the second wedge 68 so the teeth 316 on the first wedge 66 can be disengaged from the teeth 316 on the second wedge 68.

The buttress 304 in a compact configuration can be placed inside of a fully or partially deployed expandable support device 2. FIG. 135 illustrates that the first wedge 66 can then be translated, as shown by arrows, relative to the second wedge 68 along the directionally locking interface 314. The first wedge 66 can abut a first side of the inside of the deployed expandable support device 2. The second wedge 68 can abut a second side of the inside of the deployed expandable support device 2. The directionally interference fitting teeth 316 can prevent disengagement of the buttress 304. A stop 324 can limit the relative translation of the first wedge 66 and the second wedge 68.

FIGS. 136 through 139 illustrate another form of expandable support device 2 of FIGS. 17 through 20 that can be in a deployed configuration. The first struts 84 can be expanded, as shown by arrows 326. The expandable support device 2 can be passively narrow, as shown by arrows 330. The expandable support device 2 can be deployed in a configuration where the second struts 86 can be placed against the load bearing surfaces of the deployment site.

The expandable support device 2 can have a minimum inner diameter 330 and a maximum inner diameter 332. The minimum inner diameter 330 can be less than the pre-deployed inner diameter. The minimum inner diameter 330 can be from about 0.2 mm (0.01 in.) to about 120 mm (4.7 in.), for example about 2 mm (0.08 in.). The diameters 330 and/or 332 can also be from about 1.5 mm (0.060 in.) to about 40 mm (2 in.), for example about 8 mm (0.3 in.). The maximum inner diameter 332 can be more than the pre-deployed inner diameter. The maximum inner diameter 332 can be from about 1.5 mm (0.060 in.) to about 120 mm (4.7 in.), for example about 18 mm (0.71 in.).

Figure 140:
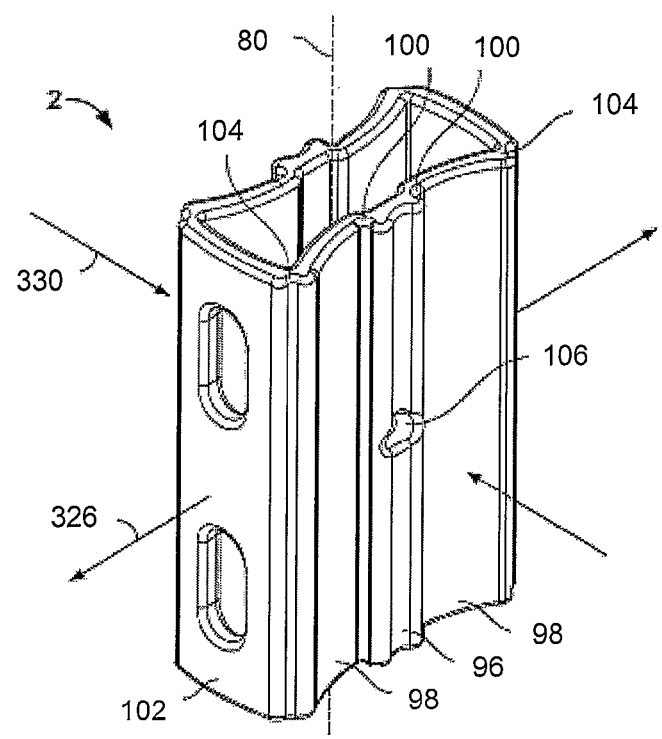
FIGS. 140 through 142 illustrate a method for deploying the expandable support device of FIGS. 31 through 34.
Figure 141:
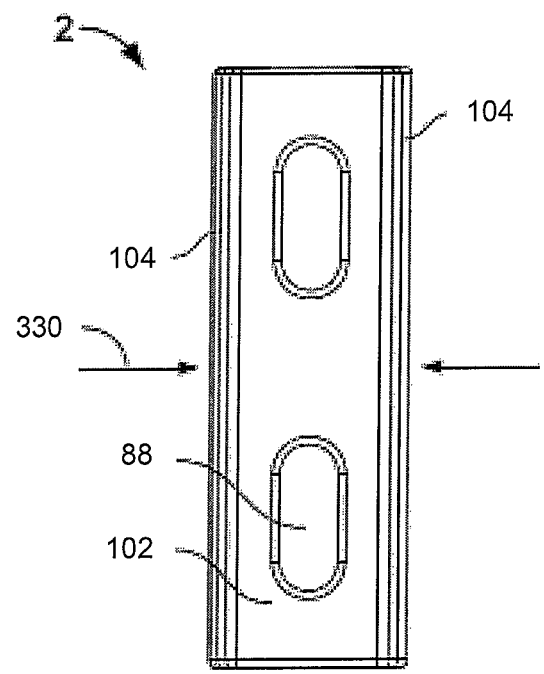
Figure 142:
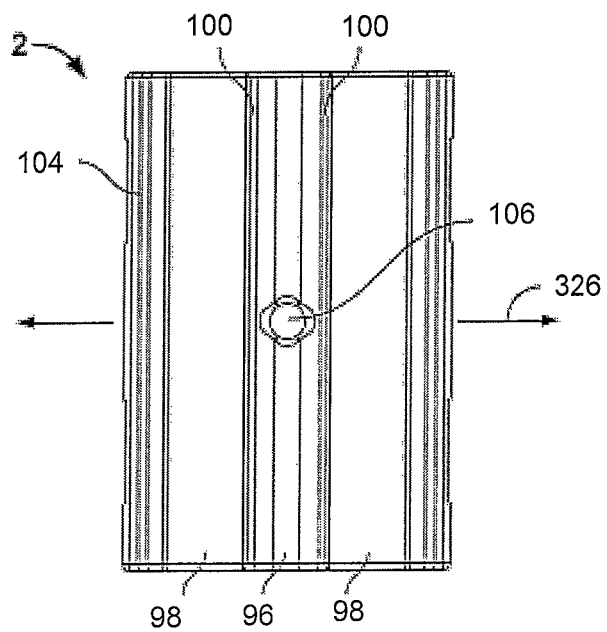

FIGS. 140 through 142 illustrate the expandable support device 2 of FIGS. 31 through 34 that can be in a deployed configuration. A tool (not shown) can releasably attach to the tool engagement port 106. The tool can be used to position the expandable support device 2. The tool can be used to expand the expandable support device 2, for example, by forcing the first panels 96 toward each other.

Figure 143:
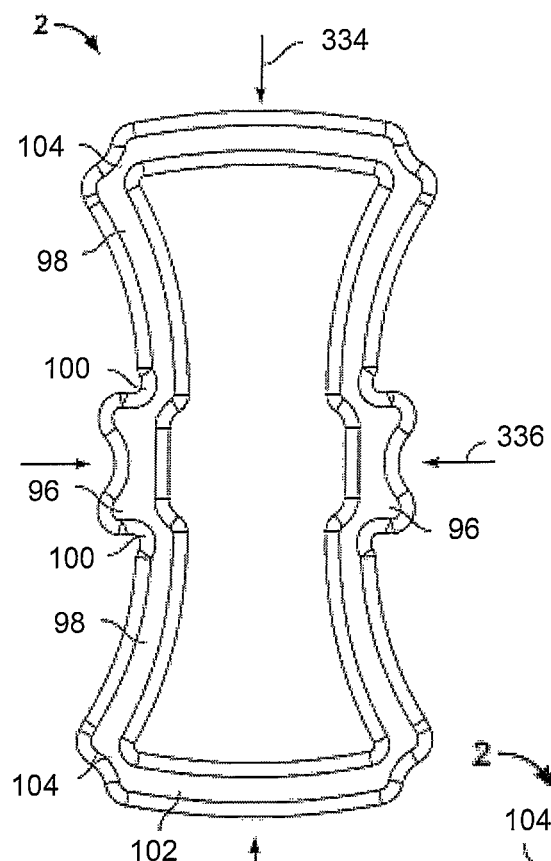
FIG. 143 illustrates the deployed expandable support device of FIGS. 31 through 34 in use.

The second joints 104 can form angles less than about 90°. As shown in FIG. 143, a compressive force, as shown by arrows 334, causes additional inward deflection, as shown by arrows 336, of the first panels 96, and will not substantially compress the expandable support device 2.

Figure 144:
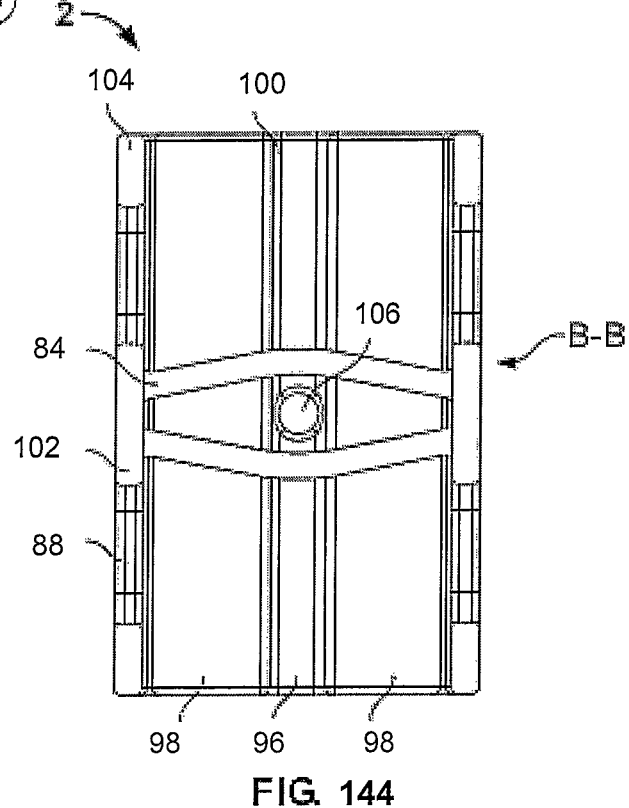
FIGS. 144 and 145 illustrate a method for deploying the expandable support device of FIGS. 35 and 36.
Figure 145:
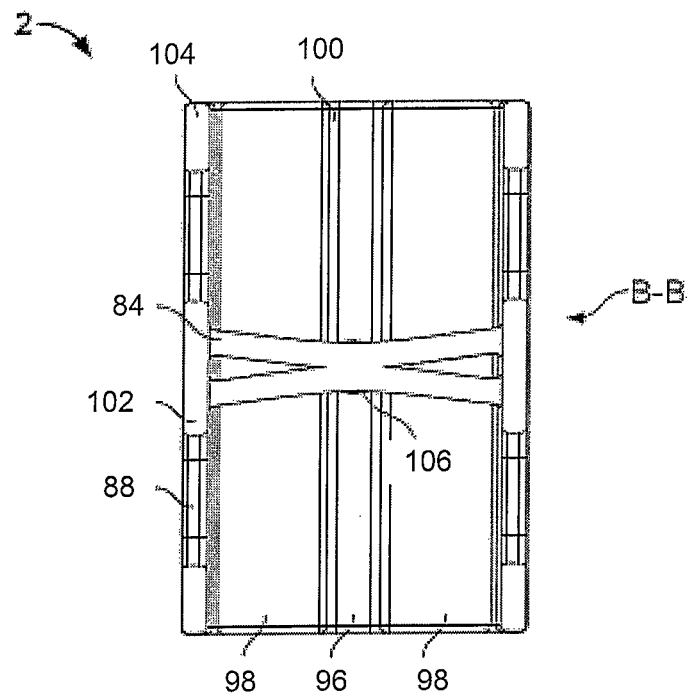

FIG. 144 illustrates a deployed configuration of the expandable support device 2 of FIGS. 35 and 36. The first struts 84 can expand to the size of the expandable support device 2. FIG. 145 illustrates that the first struts 84 can touch each other, for example if the expandable support device 2 is sufficiently expanded. In the case of extreme compressive loads applied to the expandable support device 2, the first struts 84 can buckle into each other, thereby providing additional resistance to compressive loads.

Figure 146:
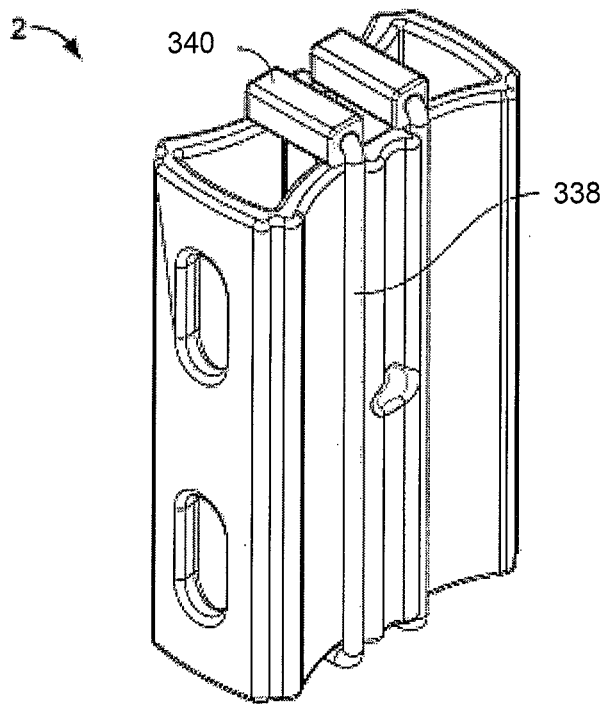
FIG. 146 illustrates a method of using the expandable support device of FIGS. 31 through 34 with the band.

FIG. 146 illustrates the expandable support device 2 that can have one or more bands 130. The bands 338 can be attached to other bands 338 and/or attached to the expandable support device 2 with band connectors 340. The bands 338 can be attached to the expandable support device 2 before, during, or after deployment. The bands 338 can increase the compressive strength of the expandable support device 2.

Figure 147:
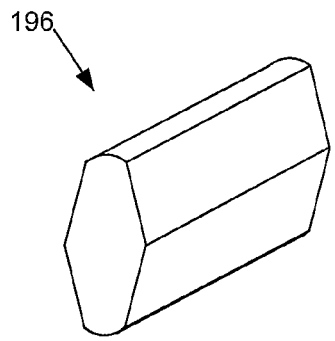
FIG. 147 through 149 illustrate variations of a locking pin.
Figure 148:
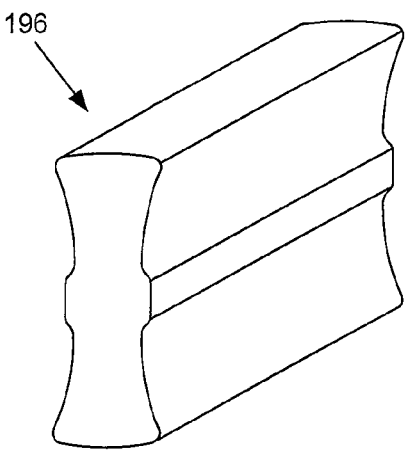
Figure 149:
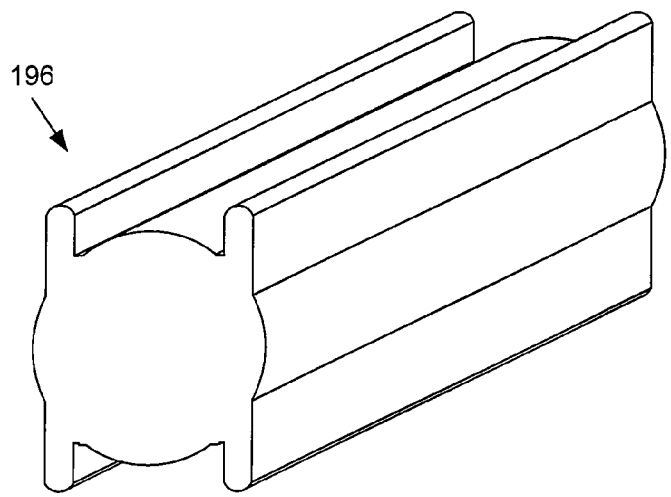

FIG. 147 illustrates a locking pin 196 configured and dimensioned to fit into the longitudinal port 82, for example, of the expanded expandable support device 2 of FIGS. 136 through 139. FIG. 148 illustrates a the locking pin 196 configured and dimensioned to fit into the longitudinal port 82, for example, of the expanded expandable support device 2 of FIGS. 140 through 143. FIG. 149 illustrates a locking pin 196 configured and dimensioned to fit into the longitudinal port 82, for example, of the expanded expandable support device 2 of FIGS. 24 and 25 and/or FIGS. 27 and 28.

Once the expandable support device 2 is deployed, the longitudinal port 82 and the remaining void volume in the damage site 146 can be filled with, for example, biocompatible coils, bone cement, morselized bone, osteogenic powder, beads of bone, polymerizing fluid, paste, a matrix (e.g., containing an osteogenic agent and/or an anti-inflammatory agent, and/or any other agent disclosed supra), Orthofix, cyanoacrylate, or combinations thereof.

The expandable support device 2 can be implanted in the place of all or part of a vertebral disc 144. For example, if the disc 144 has herniated, the expandable support device 2 can be implanted into the hernia in the disc 144 annulus, and/or the expandable support device 2 can be implanted into the disc 144 nucleus.

PCT Application No. PCT/US2005/033965, Publication No. WO 2006/034396, entitled "Balloon and Methods of Making and Using", filed Sep. 21, 2005, and U.S. Provisional Patent Application Ser. No. 60/611,972, filed on Sep. 21, 2004, are herein incorporated by reference in their entireties. PCT Application No. PCT/US2005/034728, Publication No. WO 2006/068,682, entitled "Expandable Support Device and Method of Use", filed Sep. 26, 2005, and U.S. Provisional Patent Application No. 60/612,728, filed on Sep. 24, 2004, are herein incorporated by reference in their entireties.

It is apparent to one skilled in the art that various changes and modifications can be made to this disclosure, and equivalents employed, without departing from the spirit and scope of the invention. Elements shown with any variation are exemplary for the specific variation and can be used on other variations within this disclosure. Any elements described herein as singular can be pluralized (i.e., anything described as "one" can be more than one). Any species element of a genus element can have the characteristics or elements of any other species element of that genus. The above-described configurations, elements or complete assemblies and methods and their elements for carrying out the invention, and variations of aspects of the invention can be combined and modified with each other in any combination.

We claim:

1. A method of performing surgery in a patient comprising:
accessing a bone structure;
forming an opening into the bone structure;
inserting an expandable implant having a body having a length, width and height defining a substantially hollow interior, the implant further including at least one first strut defining one of said height or width, said first strut being substantially deformable under expansion force to alter a dimension of the implant, the first strut having a first, unexpanded configuration and a second expanded configuration, the implant increasing in dimension in the direction of expansion of said first strut; and
expanding the implant to deform the first strut, thereby expanding the implant within the bone structure, wherein the expanding comprises deforming the first strut, and wherein expanding comprises expanding in an inferior-superior direction with respect to the patient;
wherein the implant further comprises sliding wedges.

2. The method of claim 1, wherein expanding the implant comprises sliding the wedges relative to each other.

3. The method of claim 1, wherein expanding the implant comprises exerting a longitudinal compression force on the wedges.

4. The method of claim 1, further comprising filling the interior of the implant with a filler.

5. The method of claim 1, further comprising inserting a locking pin into the implant.

* * * * *